United States Patent
Barbe et al.

(10) Patent No.: US 11,530,213 B2
(45) Date of Patent: *Dec. 20, 2022

(54) NAPHTHYRIDINONE DERIVATIVES AND THEIR USE IN THE TREATMENT OF ARRHYTHMIA

(71) Applicant: NOVARTIS AG, Basel (CH)

(72) Inventors: Guillaume Barbe, Milton, MA (US); Gregory Raymond Bebernitz, Tupper Lake, NY (US); Sicong Geng, Shanghai (CN); Hatice Belgin Gulgeze Efthymiou, Lynn, MA (US); Lv Liao, Shanghai (CN); Fupeng Ma, Melrose, MA (US); Ruowei Mo, New Hope, PA (US); David Thomas Parker, Windham, NH (US); Yunshan Peng, Arlington, MA (US); Stefan Peukert, Arlington, MA (US); Nichola Smith, Burlington, MA (US); Ken Yamada, Brookline, MA (US); Kayo Yasoshima, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/071,311

(22) Filed: Oct. 15, 2020

(65) Prior Publication Data

US 2021/0284635 A1 Sep. 16, 2021

Related U.S. Application Data

(63) Continuation of application No. 16/290,313, filed on Mar. 1, 2019, now Pat. No. 10,844,055, which is a continuation of application No. 15/788,248, filed on Oct. 19, 2017, now Pat. No. 10,266,531.

(60) Provisional application No. 62/410,930, filed on Oct. 21, 2016, provisional application No. 62/413,292, filed on Oct. 26, 2016.

(30) Foreign Application Priority Data

Oct. 21, 2016 (WO) ............... PCT/CN2016/102928

(51) Int. Cl.
| | | |
|---|---|---|
| A61P 9/00 | (2006.01) |
| A61P 9/06 | (2006.01) |
| C07D 471/04 | (2006.01) |
| A61K 31/4375 | (2006.01) |
| A61K 31/496 | (2006.01) |
| A61K 31/5377 | (2006.01) |
| A61K 31/541 | (2006.01) |
| A61K 31/675 | (2006.01) |
| A61K 45/06 | (2006.01) |
| C07F 9/6561 | (2006.01) |

(52) U.S. Cl.
CPC ........ *C07D 471/04* (2013.01); *A61K 31/4375* (2013.01); *A61K 31/496* (2013.01); *A61K 31/5377* (2013.01); *A61K 31/541* (2013.01); *A61K 31/675* (2013.01); *A61K 45/06* (2013.01); *A61P 9/06* (2018.01); *C07F 9/6561* (2013.01); *C07B 2200/13* (2013.01)

(58) Field of Classification Search
CPC .................................... A61P 9/00; A61P 9/06
See application file for complete search history.

(56) References Cited

U.S. PATENT DOCUMENTS

| 4,195,087 A | 3/1980 | Simonovich et al. |
| 4,698,341 A | 10/1987 | Satzinger et al. |

(Continued)

FOREIGN PATENT DOCUMENTS

| EP | 1 783 114 A1 | 5/2007 |
| GB | 1022214 | 3/1966 |

(Continued)

OTHER PUBLICATIONS

CAS Registry No. 184765-72-8, Chemical or Trade Name: 1H-Indole-3-carboxaldehyde, 1-(2,6-dichlorophenyl)-2-ethoxy—(CA Index Name); Entry Date: Jan. 8, 1997.

(Continued)

*Primary Examiner* — Bruck Kifle
(74) *Attorney, Agent, or Firm* — Timothy P. O'Dea

(57) ABSTRACT

The present invention provides a compound of formula (I) or a pharmaceutically acceptable salt thereof;

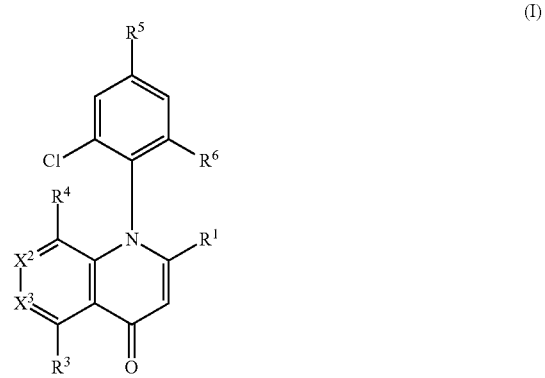

Wherein $R^1$, $R^3$-$R^6$, $X^2$ and $X^3$ are as defined herein, a method for manufacturing the compounds of the invention, and its therapeutic uses. The present invention further provides a combination of pharmacologically active agents and a pharmaceutical composition.

16 Claims, 3 Drawing Sheets

(56) References Cited

U.S. PATENT DOCUMENTS

| | | | |
|---|---|---|---|
| 5,294,620 | A | 3/1994 | Ratcliffe et al. |
| 5,910,498 | A | 6/1999 | Yazaki et al. |
| 6,136,823 | A | 10/2000 | Sakae et al. |
| 6,211,375 | B1 | 4/2001 | Yazaki et al. |
| 9,067,894 | B1 | 6/2015 | Weaver et al. |
| 10,266,551 | B2 | 4/2019 | Li et al. |
| 10,844,055 | B2 | 11/2020 | Barbe et al. |
| 2006/0074075 | A1 | 4/2006 | Hadida-Ruah et al. |
| 2007/0244135 | A1 | 10/2007 | Hoelzemann et al. |
| 2008/0146560 | A1 | 6/2008 | Hoelzemann et al. |
| 2016/0326165 | A1 | 11/2016 | Matsuyama et al. |

FOREIGN PATENT DOCUMENTS

| | | |
|---|---|---|
| JP | 57176956 A | 10/1982 |
| JP | 57176957 A | 10/1982 |
| JP | 57176958 A | 10/1982 |
| JP | 57176959 A | 10/1982 |
| JP | 2003040866 A | 2/2003 |
| WO | 1999/064400 A1 | 12/1999 |
| WO | 2000/007595 A1 | 2/2000 |
| WO | 2003/027113 A1 | 4/2003 |
| WO | 2003/063781 A2 | 8/2003 |
| WO | 2003/101988 A2 | 12/2003 |
| WO | 2005/026164 A1 | 3/2005 |
| WO | 2005/030217 A1 | 4/2005 |
| WO | 2007/002563 A1 | 1/2007 |
| WO | 2007/062399 A2 | 5/2007 |
| WO | 2009/104819 A1 | 8/2009 |
| WO | 2010/012745 A2 | 2/2010 |
| WO | 2011018611 A1 | 2/2011 |
| WO | 2011/042474 A1 | 4/2011 |
| WO | 2012/026765 A1 | 3/2012 |
| WO | 2012159959 A1 | 11/2012 |
| WO | 2013/007676 A1 | 1/2013 |
| WO | 2013152063 A1 | 10/2013 |
| WO | 2014/152317 A2 | 9/2014 |
| WO | 2014/167084 A1 | 10/2014 |
| WO | 2015019347 A1 | 2/2015 |
| WO | 2015/098693 A1 | 7/2015 |
| WO | 2016027253 A1 | 2/2016 |
| WO | 2016198342 A1 | 12/2016 |

OTHER PUBLICATIONS

CAS Registry No. 184765-53-5, Chemical or Trade Name: 2-Propenoic acid, 2-cyano-3-[1-(2,6-dichlorophenyl)-2-ethoxy-1H-indol-3-yl]-, methyl ester (CA Index Name); Entry Date: Jan. 8, 1997.

CAS Registry No. 184765-48-8, Chemical or Trade Name: 2-Propenoic acid, 2-cyano-3-[1-(2,6-dichlorophenyl)-2-ethoxy-1H-indol-3-yl]-, ethyl ester (CA Index Name); Entry Date: Jan. 8, 1997.

CAS Registry No. 184765-44-4, Chemical or Trade Name: 2-Propenamide, 2-cyano-3-[1-(2,6-dichlorophenyl)-2-ethoxy-1H-indol-3-yl]—(CA Index Name); Entry Date: Jan. 8, 1997.

CAS Registry No. 184765-39-7, Chemical or Trade Name: Propanedinitrile, 2-[[1-(2,6-dichlorophenyl)-2-ethoxy-1H-indol-3-yl]methylene]—(CA Index Name); Entry Date: Jan. 8, 1997.

CAS Registry No. 184765-32-0, Chemical or Trade Name: 1 H-Indole-3-carboxaldehyde, 1-(2,6-dichlorophenyl)-2-ethoxy-, 2-[[1-(2,6-dichlorophenyl)-2-ethoxy-1H-indol-3-yl]methylene]hydrazone (CA Index Name); Entry Date: Jan. 8, 1997.

CAS Registry No. 184765-27-3, Chemical or Trade Name: Benzenemethanamine, N-[[1-(2,6-dichlorophenyl)-2-ethoxy-1H-indol-3-yl]methylene]—(CA Index Name); Entry Date: Jan. 8, 1997.

CAS Registry No. 84977-35-5, Chemcial or Trade Name: 1H-Indole, 1-(2,6-dichlorophenyl)-2,3-bis(methylthio)—(CA Index Name); Entry Date: Nov. 16, 1984.

CAS Registry No. 84952-71-6; Chemical or Trade Name: 1H-Indole, 1-(2,6-dichlorophenyl)-2-(methylthio)—(CA InNdex Name); Entry Date: Nov. 16, 1984.

CAS Registry No. 68756-72-9, Chemical or Trade Name: Methanone, [2-amino-1-(2,6-dichlorophenyl)-1H-indol-3-yl] [4-(1,1-dimethylethyl)phenyl]—(CA Index Name); Entry Date: Nov. 16, 1984.

CAS Registry No. 68756-71-8, Chemical or Trade Name: CN Methanone, [2-amino-1-(2,6-dichlorophenyl)-1H-indol-3-yl](4-bromophenyl)—(CA Index Name); Entry Date: Nov. 16, 1984.

CAS Registry No. 68756-70-7, Chemical or Trade Name: Methanone, [2-amino-1-(2,6-dichlorophenyl)-1H-indol-3-yl] (2-methylphenyl)—(CA Index Name); Entry Date: Nov. 16, 1984.

CAS Registry No. 68756-69-4, Chemical or Trade Name: Methanone, [2-amino-1-(2,6-dichlorophenyl)-1H-indol-3-yl]phenyl—(CA Index Name); Entry Date: Nov. 16, 1984.

CAS Registry No. 1348634-94-5, Chemical or Trade Name: 2,4(1H,3H)-Quinazolinedione, 1-(2,6-dichlorophenyl)-5-(2,4-difluorophenyl)—(CA Index Name); Entry Date: Dec. 4, 2011.

CAS Registry No. 1027219-37-9, Chemical or Trade Name: 2,4(1H,3H)-Quinazolinedione, 1-(2,6-dichlorophenyl)-5-(4-fluoro-2-methylphenyl)—(CA Index Name); Entry Date: Jun. 11, 2008.

CAS Registry No. 368841-73-0, Chemical or Trade Number: 3-Quinolinecarboxylic acid, 7-chloro-1-(2,6-dichlorophenyl)-1,4-dihydro-6-nitro-4-oxo-, ethyl ester (CA Index Name); Entry Date: Nov. 11, 2001.

CAS Registry No. 304878-66-8, Chemical or Trade Number: 3-Quinolinecarboxylic acid, 1-(2,6-dichlorophenyl)-1,4-dihydro-7-(4-methyl-1-piperazinyl)-6-nitro-4-oxo—(CA Index Name); Entry Date: Nov. 29, 2000.

CAS Registry No. 252265-89-7, Chemical or Trade Number: 2,4(1H,3H)-Quinazolinedione, 1-(2,6-dichlorophenyl)-6-[(2,4-difluorophenyl)thio]—(CA Index Name); Entry Date: Jan. 6, 2000.

CAS Registry No. 55083-99-3, Chemical or Trade Number: 2,4(1H,3H)-Quinazolinedione, 1-(2,6-dichlorophenyl)—(CA Index Name); Entry Date: Nov. 16, 1984.

Lewohl, et al., "G-protein-coupled inwardly rectifying potassium channels are targets of alcohol action", Nature Neuroscience, (1999), 2(12):1084-1090.

Luscher, et al., "G-Protein-Coupled Inwardly Rectifying K+ Channels (GIRKs) Mediate Postsynaptic but not Presynaptic Transmitter Actions in Hippocampal neurons", Neuron, (1997) 19:687-695.

Notification Concerning Transmittal of International Preliminary Report on Patentability, dated May 2, 2019 in International Patent Appl. No. PCT/IB2017/056515, International Filing Date: Oct. 19, 2017, 8 pages.

Du, Yunfei et al.: "Synthesis of N-Substituted Indole Derivatives via PIFA-Mediated Intramolecular Cyclization", Organic Letters, (2006), vol. 8, No. 26, pp. 5919-5922.

Graevsksya, I. P. et al.: "Synthesis And Antihypertensive Activity Of Indolin-2-One Dienediamines", Pharmaceutical Chemistry Journal, (Nov. 1998), vol. 32, No. 11, pp. 571-574.

Li, Sai et al.: "Synthesis and Antihumor Activity of Novel 4-(2-Fluorophenoxy)-quinoilne Derivatives Bearing the 4-Oxo-1,4-dihydroquinoline-3-carboxamide Moiety", Archiv. der Pharmazie, (2013), 346(7), pp. 521-533.

Pisa, Ondrej et al.: "Synthesis of 4-Quinolones: N,O-Bis(trimethylsilyl)acetamide-Mediated Cyclization with Cleavage of Aromatic C—O Bond", European Journal of Organic Chemistry, (2016), 13, pp. 2336-2350.

CAS Registry No. 1349753-61-2, Chemical or Trade Name: 3-Quinolinecarboxylic acid, 1-[2-chloro-4-(trifluoromethyl) phenyl]-6,8-difluoro-1,4-dihydro-4-oxo-5,7-di-1-pyrrolidinyl—(CA Index Name); Entry Date: Dec. 6, 2011.

CAS Registry No. 1349490-79-4, Chemical or Trade Name: 3-Quinolinecarboxylic acid, 1-[2-chloro-4-(trifluoromethyl) phenyl]-7-(3,5-dimethyl-4-morpholinyl)-6,8-difluoro-1 ,4-dihydro-4-oxo—(CA Index Name); Entry Date: Dec. 6, 2011.

CAS Registry No. 1028271-30-8, Chemical or Trade Name: 3-Quinolinecarboxylic acid, 1-(2,4-dichlorophenyl)-6,7-difluoro-1,4-dihydro-4-oxo-, ethyl ester (CA Index Name); Entry Date: Jun. 15, 2008.

CAS Registry No. 1026747-59-0, Chemical or Trade Name: 3-Quinolinecarboxylic acid, 1-(2,4-dichlorophenyl)-6,7-difluoro-1,4-dihydro-4-oxo—(CA Index Name); Entry Date: Jun. 9, 2008.

(56) References Cited

OTHER PUBLICATIONS

CAS Registry No. 352213-33-3, Chemical or Trade Name: 3-Quinolinecarboxylic acid, 1-[2-chloro-4-(trifluoromethyl) phenyl]-6,8-difluoro-1,4-dihydro-7-(4-morpholinyl)-4-oxo—(CA Index Name); Entry Date: Aug. 21, 2001.

CAS Registry No. 304878-66-8 , Chemical or Trade Name: 3-Quinolinecarboxylic acid, 1-(2,6-dichlorophenyl)-1,4-dihydro-7-(4-methyl-1-piperazinyl)-6-nitro-4-oxo—(CA Index Name); Entry Date: Nov. 29, 2000.

CAS Registry No. 1909262-83-4, Chemical or Trade Name: 3-Quinolinecarboxylic acid, 1-(2-chloro-3-methylphenyl)-1,4-dihydro-5-methoxy-4-oxo-, ethyl ester (CA Index Name); Entry Date: May 12, 2016.

CAS Registry No. 1494545-21-9, Chemical or Trade Name: 3-Quinolinecarboxylic acid, 1-(2-chlorophenyl)-7-fluoro-1,4-dihydro-4-oxo-, ethyl ester (CA Index Name); Entry Date: Dec. 13, 2013.

CAS Registry No. 1494545-16-2, Chemical or Trade Name: 3-Quinolinecarboxylic acid, 1-(2,4-dichlorophenyl)-1,4-dihydro-4-oxo-,ethyl ester (CA Index Name); Entry Date: Dec. 13, 2013.

CAS Registry No. 1494545-12-8, Chemical or Trade Name: 3-Quinolinecarboxylic acid, 1-(2-chlorophenyl)-1,4-dihydro-4-oxo-, ethylester (CA Index Name); Entry Date: Dec. 13, 2013.

CAS Registry No. 1494544-84-1, Chemical or Trade Name: 3-Quinolinecarboxamide, 1-(2-chlorophenyl)-7-fluoro-N-[3-fluoro-4-[[6-methoxy-7-[3-(4-methyl-1-piperidinyl)propoxy]-4-quinolinyl]oxy]phenyl]-1,4-dihydro-4-oxo—(CA Index Name); Entry Date: Dec. 13, 2013.

CAS Registry No. 1494544-74-9, Chemical or Trade Name: 3-Quinolinecarboxamide, 1-(2-chlorophenyl)-7-fluoro-N-[3-fluoro-4-[[6-methoxy-7-[3-(1-piperidinyl)propoxy]-4-quinolinyl]oxy]phenyl]-1,4-dihydro-4-oxo—(CA Index Name) Entry Date: Dec. 13, 2013.

CAS Registry No. 1494544-71-6, Chemical or Trade Name: 3-Quinolinecarboxamide, 1-(2,4-dichlorophenyl)-N-[3-fluoro-4-[[6-methoxy-7-[3-(1-pyrrolidinyl)propoxy]-4-quinolinyl]oxy]phenyl]-1,4-dihydro-4-oxo—(CA Index Name); Entry Date: Dec. 13, 2013.

CAS Registry No. 1494544-66-9, Chemical or Trade Name: 3-Quinolinecarboxamide, 1-(2-chlorophenyl)-N-[3-fluoro-4-[[6-methoxy-7-[3-(4-morpholinyl)propoxy]-4-quinolinyl]oxy]phenyl]-1,4-dihydro-4-oxo—(CA Index Name) Entry Date: Dec. 13, 2013.

CAS Registry No. 1494544-60-3; Chemical or Trade Name: 3-Quinolinecarboxamide, 1-(2,4-dichlorophenyl)-N-[3-fluoro-4-[[6-methoxy-7-[3-(1-piperidinyl)propoxy]-4-quinolinyl]oxy]phenyl]-1,4-dihydro-4-oxo—(CA Index Name); Entry Date: Dec. 13, 2013.

CAS Registry No. 1494544-50-1, Chemical or Trade Name: 3-Quinolinecarboxylic acid, 1-(2-chlorophenyl)-7-fluoro-1,4-dihydro-4-oxo—(CA Index Name); Entry Date: Dec. 13, 2013.

CAS Registry No. 1494544-43-2, Chemical or Trade Name: 3-Quinolinecarboxylic acid, 1-(2,4-dichlorophenyl)-1,4-dihydro-4-oxo—(CA Index Name); Entry Date: Dec. 13, 2013.

CAS Registry No. 1494544-38-5, Chemical or Trade Name: 3-Quinolinecarboxylic acid, 1-(2-chlorophenyl)-1,4-dihydro-4-oxo—(CA Index Name); Entry Date: Dec. 13, 2013.

CAS Registry No. 1462271-66-4, Chemical or Trade Name: 3-Quinolinecarboxylic acid, 6-[(3-chloro-2-fluorophenyl) methyl]-1-(2-chlorophenyl)-5-fluoro-1,4-dihydro-4-oxo-, methyl ester (CA Index Name); Entry Date: Oct. 22, 2013.

CAS Registry No. 1447672-00-5, Chemical or Trade Name: 3-Quinolinecarboxylic acid, 6-[(3-chloro-2-fluorophenyl) methyl]-1-(2- chlorophenyl)-5-fluoro-1,4-dihydro-4-oxo—(CA Index Name); Entry Date: Aug. 5, 2013.

CAS Registry No. 1418026-38-6, Chemical or Trade Name: Benzamide, N-[[7-chloro-1-(2-chlorophenyl)-1,4-dihydro-4-oxo-3-quinolinyl]methyl]-4-(4-morpholinyl)—(CA Index Name); Entry Date: Feb. 1, 2013.

CAS Registry No. 1418026-21-7, Chemical or Trade Name: 4(1H)-Quinolinone, 3-(bromomethyl)-7-chloro-1-(2-chlorophenyl)—(CA Index Name); Entry Date: Feb. 1, 2013.

CAS Registry No. 1418025-91-8, Chemical or Trade Name: 4(1H)-Quinolinone, 3-(aminomethyl)-7-chloro-1-(2-chlorophenyl)—(CA Index Name); Entry Date: Feb. 1, 2013.

CAS Registry No. 1418025-90-7, Chemical or Trade Name: 4(1H)-Quinolinone, 3-(azidomethyl)-7-chloro-1-(2-chlorophenyl)—(CA Index Name); Entry Date: Feb. 1, 2013.

CAS Registry No. 1418025-89-4, Chemical or Trade Name: 4(1H)-Quinolinone, 7-chloro-1-(2-chlorophenyl)-3-methyl—(CA Index Name); Entry Date: Feb. 1, 2013.

CAS Registry No. 1418024-56-2 , Chemical or Trade Name: 3-Pyridinecarboxamide, N-[[7-chloro-1-(2-chlorophenyl)-1,4-dihydro-4-oxo-3-quinolinyl]methyl]-6-(1H-pyrazol-4-yl)—(CA Index Name); Entry Date: Feb. 1, 2013.

CAS Registry No. 1418024-55-1, Chemical or Trade Name: 3-Pyridinecarboxamide, 6-bromo-N-[[7-chloro-1-(2-chlorophenyl)-1,4-dihydro-4-oxo-3-quinolinyl]methyl]—(CA Index Name); Entry Date: Feb. 1, 2013.

CAS Registry No. 1418024-54-0, Chemical or Trade Name: 3-Pyridinecarboxamide, N-[[7-chloro-1-(2-chlorophenyl)-1,4-dihydro-4-oxo-3-quinolinyl]methyl]-6-(4-morpholinyl)—(CA Index Name); Entry Date: Feb. 1, 2013.

CAS Registry No. 1394165-69-5, Chemical or Trade Name: CN 3-Quinolinecarboxamide, 1-(2-chlorophenyl)-N-[3-fluoro-4-[[6-methoxy-7-[3- (4-methyl-1-piperazinyl)propoxy]-4-quinolinyl]oxy]phenyl]-1,4-dihydro-4-oxo—(CA Index Name); Entry Date: Sep. 13, 2012.

CAS Registry No. 1394165-68-4, Chemical or Trade Name: 3-Quinolinecarboxamide, 1-(2-chlorophenyl)-N-[3-fluoro-4-[[6-methoxy-7-[3-(1-pyrrolidinyl)propoxy]-4-quinolinyl]oxy]phenyl]-1,4-dihydro-4-oxo—(CA Index Name) Entry Date: Sep. 13, 2012.

CAS Registry No. 1394165-67-3, Chemical or Trade Number: 3-Quinolinecarboxamide, 1-(2-chlorophenyl)-N-[3-fluoro-4-[[6-methoxy-7-[3- (4-methyl-1-piperidinyl)propoxy]-4-quinolinyl]oxy]phenyl]-1,4-dihydro-4-oxo—(CA Index Name); Entry Date: Sep. 13, 2012.

CAS Registry No. 1394165-66-2, Chemical or Trade Number: 3-Quinolinecarboxamide, 1-(2-chlorophenyl)-N-[3-fluoro-4-[[6-methoxy-7-[3- (1-piperidinyl)propoxy]-4-quinolinyl]oxy]phenyl]-1,4-dihydro-4-oxo—(CA Index Name); Entry Date: Sep. 13, 2012.

CAS Registry No. 1258792-45-8, Chemical or Trade Number: 4(1H)-Quinolinone, 1-(2,4-dichlorophenyl)-3-phenyl—(CA Index Name); Entry Date: Jan. 7, 2011.

CAS Registry No. 1230467-59-0, Chemical or Trade Number: 3-Quinolinecarboxamide, 1-[2-chloro-4-(phenylmethoxy) phenyl]-7-(2,6- dimethyl-4-pyridinyl)-1,4-dihydro-4-oxo—(CA Index Name); Entry Date: Jul. 11, 2010.

CAS Registry No. 1230467-57-8, Chemical or Trade Number: 3-Quinolinecarboxamide, 1-(2-chloro-4-hydroxyphenyl)-7-(2,6-dimethyl-4-pyridinyl)-1,4-dihydro-4-oxo—(CA Index Name); Entry Date: Jul. 11, 2010.

CAS Registry No. 1230467-55-6, Chemical or Trade Number: 3-Quinolinecarboxamide, 1-(2-chloro-4-hydroxyphenyl)-7-(4-cyanophenyl)-1,4-dihydro-4-oxo—(CA Index Name); Entry Date: Jul. 11, 2010.

CAS Registry No. 1230467-48-7, Chemical or Trade Number: 3-Quinolinecarboxamide, 1-(2-chloro-4-hydroxyphenyl)-7-(3-fluoro-4-pyridinyl)-1,4-dihydro-4-oxo—(CA Index Name); Entry Date: Jul. 11, 2010.

CAS Registry No. 208164-94-7, Chemical or Trade Number: 3-Quinolinecarboxylic acid, 1-(5-amino-2-chloro-4-fluorophenyl)-8-chloro-6-fluoro-1,4-dihydro-7-(methylamino)-4-oxo—(CA Index Name); Entry Date: Jul. 9, 1998.

CAS Registry No. 198014-03-8, Chemical or Trade Number: CN 3-Quinolinecarboxylic acid, 1-(5-amino-2-chloro-4-fluorophenyl)-6,7-difluoro-1,4-dihydro-8-methyl-4-oxo—(CA Index Name); Entry Date: Dec. 3, 1997.

CAS Registry No. 198014-02-7, Chemical or Trade Number: 3-Quinolinecarboxylic acid, 1-[2-chloro-4-fluoro-5-(formylamino)phenyl]-6,7-difluoro-1,4-dihydro-8-methyl-4-oxo-, ethyl ester (CA Index Name); Entry Date: Dec. 3, 1997.

CAS Registry No. 198014-01-6, Chemical or Trade Name:3-Quinolinecarboxylic acid, 1-(2-chloro-4-fluoro-5-nitrophenyl)-6,7-difluoro-1,4-dihydro-8-methyl-4-oxo-, ethyl ester (CA Index Name); Entry Date: Dec. 3, 1997.

(56) References Cited

OTHER PUBLICATIONS

CAS Registry No. 198014-00-5, Chemical or Trade Name: CN 3-Quinolinecarboxylic acid, 1-(2-chloro-4-fluorophenyl)-6,7-difluoro-1,4-dihydro-8-methyl-4-oxo-, ethyl ester (CA Index Name); Entry Date: Dec. 3, 1997.

CAS Registry No. 198013-89-7, Chemical or Trade Name: 3-Quinolinecarboxylic acid, 7-(3-amino-1-azetidinyl)-1-(5-amino-2-chloro-4-fluorophenyl)-6-fluoro-1,4-dihydro-8-methyl-4-oxo— (CA Index Name); Entry Date: Dec. 3, 1997.

CAS Registry No. 190060-70-9, Chemical or Trade Name:3-Quinolinecarboxamide, 1-(2-chloro-4-hydroxyphenyl)-7-(3,5-dimethyl-4-isoxazolyl)-1,4-dihydro-4-oxo—(CA Index Name); Entry Date: Jun. 19, 1997.

CAS Registry No. 190060-65-2, Chemical or Trade Name: 3-Quinolinecarboxamide, 1-(2-chloro-4-hydroxyphenyl)-1,4-dihydro-4-oxo-7-phenyl—(CA Index Name); Entry Date: Jun. 19, 1997.

CAS Registry No. 190060-64-1, Chemical or Trade Name: 3-Quinolinecarboxamide, 1-(2-chloro-4-hydroxyphenyl)-7-(3-chloro-4-pyridazinyl)-1,4-dihydro-4-oxo—(CA Index Name); Entry Date: Jun. 19, 1997.

CAS Registry No. 190060-63-0 , Chemical or Trade Name: 3-Quinolinecarboxamide, 1-(2-chloro-4-hydroxyphenyl)-1,4-dihydro-4-oxo-7-(1H-pyrazol-3-yl)—(CA Index Name); Entry Date: Jun. 19, 1997.

CAS Registry No. 190060-62-9, Chemical or Trade Name: 3-Quinolinecarboxamide, 1-(2-chloro-4-hydroxyphenyl)-1,4-dihydro-4-oxo-7-(4-pyridazinyl)—(CA Index Name); Entry Date: Jun. 19, 1997.

CAS Registry No. 190060-61-8, Chemical or Trade Name: 3-Quinolinecarboxamide, 1-(2-chloro-4-hydroxyphenyl)-7-3-chloro-4-pyridinyl)-1,4-dihydro-4-oxo—(CA Index Name); Entry Date: Jun. 19, 1997.

CAS Registry No. 181627-21-4, Chemical or Trade Name: 3-Quinolinecarboxylic acid, 7-(3-amino-1-azetidinyl)-1-(5-amino-2-chloro-4- fluorophenyl)-8-chloro-6-fluoro-1,4-dihydro-4-oxo— (CA Index Name); Entry Date: Oct. 8, 1996.

CAS Registry No. 181626-98-2, Chemical or Trade Name: 3-Quinolinecarboxylic acid, 7-(3-amino-1-azetidinyl)-1-(5-amino-2-chloro-4-fluorophenyl)-6-fluoro-1,4-dihydro-4-oxo—(CA Index Name); Entry Date: Oct. 8, 1996.

CAS Registry No. 181626-04-0, Chemical or Trade Name: 3-Quinolinecarboxylic acid, 1-(5-amino-2-chloro-4-fluorophenyl)-6-fluoro-1,4-dihydro-4-oxo-7-(1-piperazinyl)—(CA Index Name); Entry Date: Oct. 8, 1996.

CAS Registry No. 181624-89-5, Chemical or Trade Name: 3-Quinolinecarboxylic acid, 1-(2-chloro-4-fluoro-5-nitrophenyl)-6,7-difluoro-1,4-dihydro-4-oxo-, ethyl ester (CA Index Name); Entry Date: Oct. 8, 1996.

CAS Registry No. 180904-37-4, Chemical or Trade Name: 3-Quinolinecarbonitrile, 1-(2,4-dichlorophenyl)-1,4-dihydro-2-(methylthio)-4-oxo—(CA Index Name); Entry Date: Sep. 18, 1996.

CAS Registry No. 179741-62-9, Chemical or Trade Name: 3-Quinolinecarboxylic acid, 8-chloro-1-(2-chloro-4-fluorophenyl)-6,7-difluoro-1,4-dihydro-4-oxo-, ethyl ester (CA Index Name); Entry Date: Aug. 16, 1996.

CAS Registry No. 179741-55-0, Chemical or Trade Name: 3-Quinolinecarboxylic acid, 1-(2-chloro-4-fluorophenyl)-6,7-difluoro-1,4-dihydro-4-oxo-, ethyl ester (CA Index Name); Entry Date: Aug. 16, 1996.

CAS Registry No. 179740-92-2, Chemical or Trade Name: 3-Quinolinecarboxylic acid, 1-(5-amino-2-chloro-4-Tuorophenyl)-7-(3-amino-1-pyrrolidinyl)-8-chloro-6-fluoro-1,4-dihydro-4-oxo-, (S)-(9CI) (CA Index Name); Entry Date: Aug. 16, 1996.

CAS Registry No. 179740-91-1, Chemical or Trade Name: 3-Quinolinecarboxylic acid, 1-(5-amino-2-chloro-4-fluorophenyl)-8-chloro-6,7-difluoro-1,4-dihydro-4-oxo—(CA Index Name); Entry Date: Aug. 16, 1996.

CAS Registry No. 179740-90-0, Chemical or Trade Name: 3-Quinolinecarboxylic acid, 8-chloro-1-(2-chloro-4-fluoro-5-nitrophenyl)-6,7-difluoro-1,4-dihydro-4-oxo-, ethyl ester (CA Index Name); Entry Date: Aug. 16, 1996.

CAS Registry No. 179740-89-7, Chemical or Trade Name: 3-Quinolinecarboxylic acid, 5-amino-7-(3-amino-1-azetidinyl)-1-(5-amino-2-chloro-4-fluorophenyl)-8-chloro-6-fluoro-1,4-dihydro-4-oxo-, methanesulfonate (1:1) (CA Index Name); Entry Date: Aug. 16, 1996.

CAS Registry No. 179740-88-6, Chemical or Trade Name: 3-Quinolinecarboxylic acid, 5-amino-7-(3-amino-1-azetidinyl)-1-(5-amino-2-chloro-4-fluorophenyl)-8-chloro-6-fluoro-1,4-dihydro-4-oxo-, 4-methylbenzenesulfonate (1:1) (CA Index Name); Entry Date: Aug. 16, 1996.

CAS Registry No. 179740-87-5, Chemical or Trade Name: 3-Quinolinecarboxylic acid, 5-amino-7-(3-amino-1-azetidinyl)-1-(5-amino-2-chloro-4-fluorophenyl)-8-chloro-6-fluoro-1,4-dihydro-4-oxo—(CA Index Name); Entry Date Aug. 16, 1996.

CAS Registry No. 179740-83-1, Chemical or Trade Name: 3-Quinolinecarboxylic acid, 5-amino-1-(5-amino-2-chloro-4-fluorophenyl)-7-(3-amino-2-methyl-1-azetidinyl)-8-chloro-6-fluoro-1,4-dihydro-4-oxo-, trans-(9CI) (CA Index Name) Entry Date: Aug. 16, 1996.

CAS Registry No. 179740-82-0, Chemical or Trade Name: 3-Quinolinecarboxylic acid, 5-amino-7-(3-amino-1-azetidinyl)-1-(5-amino-2-chloro-4-fluorophenyl)-6-fluoro-1,4-dihydro-4-oxo—(CA Index Name); Entry Date: Aug. 16, 1996.

CAS Registry No. 179740-15-9, Chemical or Trade Name: 3-Quinolinecarboxylic acid, 1-(5-amino-2-chloro-4-fluorophenyl)-6-fluoro-1,4-dihydro-4-oxo-7-(1-piperidinyl)—(CA Index Name); Entry Date: Aug. 16, 1996.

CAS Registry No. 179739-94-7, Chemical or Trade Name: CN 3-Quinolinecarboxylic acid, 1-(5-amino-2-chloro-4-fluorophenyl)-7-(3-amino-1-pyrrolidinyl)-6-fluoro-1,4-dihydro-4-oxo-, (S)-(9CI) (CA Index Name); Entry Date: Aug. 16, 1996.

CAS Registry No. 179739-55-0, Chemical or Trade Name: 3-Quinolinecarboxylic acid, 1-(5-amino-2-chloro-4-fluorophenyl)-6,7-difluoro-1,4-dihydro-4-oxo—(CA Index Name); Entry Date: Aug. 16, 1996.

CAS Registry No. 179739-54-9, Chemical or Trade Name: 3-Quinolinecarboxylic acid, 1-(5-amino-2-chloro-4-fluorophenyl)-6,7-difluoro-1,4-dihydro-4-oxo-, ethyl ester (CA Index Name); Entry Date: Aug. 16, 1996.

CAS Registry No. 173061-67-1; Chemical or Trade Name: 3-Quinolinecarboxylic acid, 7-chloro-1-(2-chlorophenyl)-1,4-dihydro-6-nitro-4-oxo-, ethyl ester (CA Index Name); Entry Date: Feb. 9, 1996.

CAS Registry No. 164662-51-5; Chemical or Trade Name: 3-Quinolinecarboxylic acid, 1-(2,4-dichlorophenyl)-7-(3,5-dimethyl-1- piperazinyl)-6-fluoro-1,4-dihydro-4-oxo—(CA Index Name); Entry Date: Jul. 12, 1995.

CAS Registry No. 164662-42-4, Chemical or Trade Name: 3-Quinolinecarboxylic acid, 1-(2,4-dichlorophenyl)-6-fluoro-1,4-dihydro-4-oxo-7-(1-piperazinyl)—(CA Index Name); Entry Date: Jul. 12, 1995.

CAS Registry No. 164261-30-7, Chemical or Trade Name: 3-Quinolinecarboxamide, 1-[2-chloro-4-(phenylmethoxy) phenyl]-1,4-dihydro-4-oxo-7-(1H-pyrazol-3-yl)—(CA Index Name); Entry Date: Jun. 30, 1995.

CAS Registry No. 164261-29-4, Chemical or Trade Name: 3-Quinolinecarboxamide, 7-bromo-1-[2-chloro-4-(phenylmethoxy)phenyl]-1,4-dihydro-4-oxo—(CA Index Name); Entry Date: Jun. 30, 1995.

CAS Registry No. 164261-28-3, Chemical or Trade Name: 3-Quinolinecarboxylic acid, 7-bromo-1-[2-chloro-4-(phenylmethoxy)phenyl]-1,4-dihydro-4-oxo-, ethyl ester (CA Index Name); Entry Date: Jun. 30, 1995.

CAS Registry No. 164261-17-0, Chemical or Trade Number: 3-Quinolinecarboxamide, 1-(2-chloro-4-hydroxyphenyl)-1,4-dihydro-4-oxo-7-(4-pyridinyl)—(CA Index Name); Entry Date: Jun. 30, 1995.

CAS Registry No. 164261-10-3, Chemical or Trade Number: 3-Quinolinecarboxamide, 1-(2-chloro-4-hydroxyphenyl)-7-(3,5-dimethyl-4-pyridinyl)-1,4-dihydro-4-oxo—(CA Index Name); Entry Date: Jun. 30, 1995.

(56) References Cited

OTHER PUBLICATIONS

CAS Registry No. 164261-09-0; Chemical or Trade Name: 3-Quinolinecarboxamide, 1-(2-chloro-4-hydroxyphenyl)-7-(2-fluoro-4-pyridinyl)-1,4-dihydro-4-oxo—(CA Index Name); Entry Date: Jun. 30, 1995.

CAS Registry No. 164261-08-9; Chemical or Trade Name: 3-Quinolinecarboxamide, 1-(2-chloro-4-hydroxyphenyl)-1,4-dihydro-4-oxo-7-(2-pyridinyl)—(CA Index Name); Entry Date: Jun. 30, 1995.

CAS Registry No. 164261-07-8; Chemical or Trade Name: 3-Quinolinecarboxamide, 1-(2-chloro-4-hydroxyphenyl)-1,4-dihydro-4-oxo-7-(3-pyridinyl)—(CA Index Name); Entry Date: Jun. 30, 1995.

CAS Registry No. 164261-06-7, Chemical or Trade Name: 3-Quinolinecarboxamide, 1-(2-chloro-4-hydroxyphenyl)-1,4-dihydro-4-oxo-7-(3-pyridazinyl)—(CA Index Name); Entry Date: Jun. 30, 1995.

CAS Registry No. 164261-05-6, Chemical or Trade Name: 3-Quinolinecarboxamide, 1-(2-chloro-4-hydroxyphenyl)-7-(2-chloro-4-pyridinyl)-1,4-dihydro-4-oxo—(CA Index Name); Entry Date: Jun. 30, 1995.

CAS Registry No. 164261-04-5, Chemical or Trade Name: 3-Quinolinecarboxamide, 1-(2-chloro-4-hydroxyphenyl)-7-(3-furanyl)-1,4-dihydro-4-oxo—(CA Index Name); Entry Date: Jun. 30, 1995.

CAS Registry No. 164261-03-4, Chemical or Trade Name: 3-Quinolinecarboxamide, 1-(2-chloro-4-hydroxyphenyl)-1,4-dihydro-4-oxo-7-(1H-pyrazol-1-yl)—(CA Index Name); Entry Date: Jun. 30, 1995.

CAS Registry No. 1026305-54-3, Chemical or Trade Name: 1H-Imidazole-4-methanol, 1-(2,6-dichlorophenyl)-2-[5-[3-(ethylsulfonyl)phenyl]-2-thienyl]-alpha, alpha-difluoro—(CA Index Name); Entry Date: Jun. 8, 2008.

CAS Registry No. 918349-84-5, Chemical or Trade Name: 1H-Imidazole-4-carboxylic acid, 1-(2,6-dichlorophenyl)-2-[5-[3-(methylsulfonyl)phenyl]-2-thienyl]-, ethyl ester (CA Index Name); Entry Date: Jan. 24, 2007.

CAS Registry No. 918349-83-4, Chemical or Trade Name: 1H-Imidazole-4-carboxylic acid, 2-(5-bromo-2-thienyl)-1-(2,6-dichlorophenyl)-, ethyl ester (CA Index Name); Entry Date: Jan. 24, 2007.

CAS Registry No. 918345-06-9, Chemical or Trade Name: 1H-Imidazole-4-methanol, 1-(2,6-dichlorophenyl)-2-[5-[3-(ethylsulfonyl)phenyl]-2-thienyl]-alpha, alpha-dimethyl—(CA Index Name); Entry Date: Jan. 24, 2007.

CAS Registry No. 918345-05-8, Chemical or Trade Name: 1H-Imidazole-4-methanol, 1-(2,6-dichlorophenyl)-alpha, alpha-dimethyl-2-[5-[3-(methylsulfonyl)phenyl]-2-thienyl]—(CA Index Name); Entry Date: Jan. 24, 2007.

CAS Registry No. 1056607-13-6, Chemical or Trade Name: 1H-Indole-3-methanol, 1-(2,6-dichlorophenyl)-alpha-methyl-alpha-(trifluoromethyl)—(CA Index Name); Entry Date: Oct. 3, 2008.

CAS Registry No. 922184-58-5, Chemical or Trade Name: 1H-Indole-3-carbonitrile, 1-(2,6-dichlorophenyl)-6-methoxy-2-methyl—(CA Index Name); Entry Date: Feb. 20, 2007.

CAS Registry No. 864071-51-2, Chemical or Trade Name: 1H-Indol-2-ol, 1-(2,6-dichlorophenyl)—(CA Index Name); Entry Date: Sep. 28, 2005.

CAS Registry No. 582320-01-2, Chemical or Trade Name: 2-Propenoic acid, 3-[1-(2,6-dichlorophenyl)-1H-indol-3-yl]-, methyl ester (CA Index Name); Entry Date: Sep. 10, 2003.

CAS Registry No. 221349-95-7, Chemical or Trade Name: Propanedinitrile, [[1-(2,6-dichlorophenyl)-2-hydroxy-1H-indol-3-yl]methylene]-, compd. with N,N-diethylethanamine (1:1) (CA Index Name); Entry Date: Apr. 20, 1999.

CAS Registry No. 221349-94-6, Chemical or Trade Name: Propanedinitrile, 2-[[1-(2,6-dichlorophenyl)-2-hydroxy-1H-indol-3yl]methylene]—(CA Index Name); Entry Date: Apr. 20, 1999.

NAPHTHYRIDINONE DERIVATIVES AND THEIR USE IN THE TREATMENT OF ARRHYTHMIA

RELATED APPLICATIONS

This application is a continuation of U.S. application Ser. No. 16/290,313 filed Mar. 1, 2019, which is a continuation of U.S. application Ser. No. 15/788,248 filed Oct. 19, 2017, which claims priority to and the benefit of under 35 U.S.C. § 119 of Chinese patent application No. PCT/CN2016/102928 filed on Oct. 21, 2016; U.S. Provisional Application No. 62/410,930, filed Oct. 21, 2016; and U.S. Provisional Application No. 62/413,292, filed on Oct. 26, 2016; the contents of which are incorporated herein by reference in their entireties.

FIELD OF THE INVENTION

The invention provides naphthyridinone compounds, the use thereof for inhibiting GIRK 1/4 channel and methods of treating diseases using same.

BACKGROUND OF THE INVENTION

A normal cardiac cycle begins in the sino-atrial node, which produces an excitatory electrical stimulus that propagates in an orderly fashion throughout the atrial and ventricular myocardium to induce a contraction (systole). At the cellular level, the excitatory electrical impulse triggers the cardiac action potential. This is characterized by an initial, rapid membrane depolarization followed by a plateau phase and subsequent repolarization to return to resting membrane potential. The cardiac action potential governs signal propagation throughout the heart. For example, the rate of initial cellular depolarization determines the velocity at which excitatory stimuli propagate. The duration of the repolarization phase determines the action potential duration (APD) and the refractory period, or time in which a cardiomyocyte cannot respond to another electrical stimulus.

Abnormalities in the cardiac action potential are associated with arrhythmia. For example, excessive reduction of action potential duration and the associated refractory period can provide a substrate for so-called re-entrant tachyarrhythmia. In this condition, instead of propagating normally, a cardiac impulse feeds back upon itself via excitable tissue to form a re-entrant circuit (Waldo and Wit, 1993. Mechanism of cardiac arrhythmias. Lancet 341, 1189-1193). Existing class III anti-arrhythmic drugs are thought to work by lengthening the APD and associated effective refractory period (ERP), thereby minimizing the risk of re-excitation and subsequent formation of fibrillatory re-entry circuits (Singh B. N. and Vaughan Williams, E. M., 1970. A third class of anti-arrhythmic action. Effects on atrial and ventricular intracellular potentials, and other pharmacological actions on cardiac muscle, of MJ 1999 and AH3474. British Journal of pharmacology 39, 675-687).

Certain class III anti-arrhythmic drugs (e.g. sotalol) are used in the treatment of atrial fibrillation (AF). AF is the most common form of sustained cardiac arrhythmia in humans and is characterized by fibrillatory contractions that compromise atrial function. AF is associated with adverse cardiovascular events. In particular, the presence of AF is an independent risk factor for thromboembolic stroke, heart failure and all-cause mortality (Estes et al., (2008). Journal of the American College of Cardiology 51, 865-884) (Fang et al., 2008. Comparison of risk stratification schemes to predict thromboembolism in people with nonvalvular atrial fibrillation. Journal of the American College of Cardiology 51, 810-815). AF can also reduce quality of life in some patients by inducing palpitations and reducing exercise tolerance (Thrall et al., 2006. Quality of life in patients with atrial fibrillation: a systematic review. The American journal of medicine 119, 448.e441-419). The goal of anti-arrhythmic therapy for AF is to avoid these adverse effects and outcomes.

A drawback of existing Class III anti-arrhythmic drugs is that they act to prolong effective refractory period in both atria and ventricles. Excessive prolongation in ventricular tissue lengthens QTc interval and can be pro-arrhythmic, and certain drugs with this mechanism of action (e.g. dofetilide) are known to induce potentially life-threatening ventricular arrhythmias such as Torsades de Pointes (Redfern et al., 2003. Relationships between preclinical cardiac electrophysiology, clinical QT interval prolongation and torsade de pointes for a broad range of drugs: evidence for a provisional safety margin in drug development. Cardiovascular research 58, 32-45). There is thus a need for a novel anti-arrhythmic therapy for AF that targets atrial, and not ventricular, tissue selectively.

The configuration and duration of the cardiac action potential is controlled at the cellular level by the action of multiple different transmembrane ion channels. For example, the initial depolarization phase is mediated by influx of sodium ions via the cardiac-specific $Na_v1.5$ channel. Potassium channels are responsible for the latter phase of repolarization, and thus help regulate the overall duration of the action potential. Indeed, class III anti-arrhythmic drugs that target potassium channels (e.g. dofetilide) prolong both action potential duration and effective refractory period. There are several different varieties of transmembrane potassium channel (Schmitt et al., 2014. Cardiac potassium channel subtypes: new roles in repolarization and arrhythmia. Physiological reviews 94, 609-653; Tamargo et al., 2004. Pharmacology of cardiac potassium channels. Cardiovascular research 62, 9-33), including:

Voltage-gated channels (Kv1-9)
Calcium-activated channels (KCa1-2)
Tandem pore domain channels (e.g. TASK)
Inwardly rectifying channels (Kir1-6)

While most cardiac potassium channels contribute to repolarization in both atrial and ventricular tissues in humans, two—$K_v1.5$ and GIRK1/4 G-protein regulated inwardly rectifying potassium channel 1/4)—are thought to be expressed solely in atria (Gaborit et al., 2007. Regional and tissue specific transcript signatures of ion channel genes in the non-diseased human heart. The Journal of physiology 582, 675-693). This atrial-specific pattern of expression makes these particularly attractive targets for novel anti-arrhythmic therapies for AF, as they should not have the adverse ventricular effects of existing Class III drugs such as dofetilide.

Mammals express four different GIRK channels (GIRK 1, 2, 3 and 4; encoded by KCNJ3, KCNJ6, KCNJ9 and KCNJ5, respectively). These transmembrane spanning proteins are arranged as tetramers (either homo or heterotetramers) to form a functional potassium channel (Krapivinsky et al., 1995. The G-protein-gated atrial K+ channel IKACh is a heteromultimer of two inwardly rectifying K(+)-channel proteins. Nature 374, 135-141). These channels are ligand-gated (i.e. regulated by binding of ligands to Gi-protein coupled receptors present in the same cell membrane). For example, the GIRK1/4 channel is a heterotetramer (two subunits each of GIRK1 and GIRK4) expressed strongly in sino-atrial and atrioventricular nodes as well as the atrial myocardium (Wickman et al., 1999. Structure, G protein activation, and functional relevance of the cardiac G protein-gated K+ channel, IKACh. Annals of the New York Academy of Sciences 868, 386-398). One function of this channel is to mediate autonomic regulation of heart rate. Acetylcholine released upon parasympathetic stimulation of cardiac vagal efferent neurons binds to Gi-coupled M2 muscarinic receptors in heart. This liberates Gβγ subunits, which in turn open GIRK1/4 channels to permit efflux of potassium from cardiomyocytes and so promote membrane repolarization. In the spontaneously depolarizing pacemaking cells of the sino-atrial node, the magnitude of this repolarization dictates the timing between depolarizations, and hence heart rate. Because it is regulated by acetylcholine, the current mediated by GIRK1/4 channels is called $I_{KAch}$ (Wickman et al., 1999).

Several lines of evidence point toward GIRK1/4 as a desirable anti-arrhythmia target for AF. In animals, vagal nerve stimulation promotes acetylcholine release from vagal afferents and an increase in $I_{KAch}$. This in turn shortens atrial (but not ventricular) action potential duration and effective refractory period and can induce AF via a re-entry mechanism (Hashimoto et al., 2006. Tertiapin, a selective IKACh blocker, terminates atrial fibrillation with selective atrial effective refractory period prolongation. Pharmacological research: the official journal of the Italian Pharmacological Society 54, 136-141). In atrial tissues from humans with persistent AF as well as from animals subjected to atrial rapid pacing (an accepted model for promoting electrical remodeling and susceptibility to AF), $I_{KAch}$ has been shown to be dysregulated. Specifically, the channel tends to be constitutively open, even in the absence of acetylcholine (Cha et al., 2006. Kir3-based inward rectifier potassium current: potential role in atrial tachycardia remodeling effects on atrial repolarization and arrhythmias. Circulation 113, 1730-1737; Voigt et al., 2014. Constitutive activity of the acetylcholine-activated potassium current IK,ACh in cardiomyocytes. Advances in pharmacology (San Diego, Calif.) 70, 393-409). In these studies, it is observed in patients and animals that atrial APD/ERP is short. Thus, the development of GIRK1/4 blockers would be beneficial in the treatment of cardiac arrhythmias such as atrial fibrillation.

SUMMARY OF THE INVENTION

There remains a need for new treatments and therapies for arrhythmia. The invention provides compounds, pharmaceutically acceptable salts thereof, pharmaceutical compositions thereof and combinations thereof, which compounds are GIRK1/4 channel blockers. The invention further provides methods of treating, preventing, or ameliorating cardiac arrhythmia, atrial fibrillation, primary hyperaldosteronism, hypertension and/or sick sinus syndrome, comprising administering to a subject in need thereof an effective amount of a GIRK1/4 channel blocker.

Various embodiments of the invention are described herein.

Within certain aspects, provided herein is a compound of Formula I:

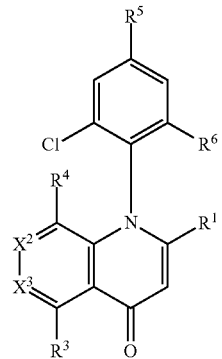

I wherein:
$X^2$ is $CR^2$ or N;
$X^3$ is CH or N;
$R^1$ is $C_{1-4}$alkyl, —$CH_2CN$, —CN, $C_{1-4}$alkoxy$C_{1-4}$alkyl, halo-$C_{1-4}$alkyl, —CH=N—OH, —CH=N—O—$C_{1-4}$alkyl, —CH=N—O-(hydroxy$C_{1-4}$alkyl), hydroxy-$C_{1-4}$alkyl, —$CH_2OP(O)(OH)_2$ or $C_{3-5}$cycloalkyl; $R^3$ is —$OR^a$, —$NHR^b$, —$C(O)NH_2$; —C(O)[hydroxy$C_{1-4}$alkyl], heterocyclyl optionally substituted with one or more substituents independently selected from OH and hydroxy$C_{1-4}$alkyl; 5- or 6-membered ring heteroaryl optionally substituted with one or more $C_{1-4}$alkyl; or $R^3$ is $C_{1-4}$alkyl substituted with one or more substituents independently selected from —C(O)[hydroxy$C_{1-4}$alkyl] and —$OR^c$;
$R^a$ is —$C_{1-6}$alkyl substituted with one or more substituents independently selected from —$OR^c$, —$SO_2C_{1-4}$alkyl, —$NHS(O)_2C_{1-4}$alkyl and heterocyclyl which is further optionally substituted with one or more substituent independently selected from $C_{1-4}$alkyl or hydroxy$C_{1-4}$alkyl; or
$R^a$ is H, —$[CH_2—CH_2—O]_n$—H, —$[CH_2—CH_2—O]_m$—$CH_3$ or heteroaryl optionally substituted with one or more $C_{1-4}$alkyl; wherein n is 2-6 and m is 1-6;
$R^b$ is —$C_{1-6}$alkyl substituted with one or more substituents independently selected from —$OR^c$, —C(O)NH—$C_{1-4}$alkyl, —C(O)NH-(hydroxy$C_{1-4}$alkyl), hydroxy$C_{1-4}$alkyl, 5- or 6-membered heteroaryl, heterocyclyl, —$SO_2C_{1-4}$alkyl and —$NHS(O)_2C_{1-4}$alkyl; or $R^b$ is —$S(O)_2$heteroaryl; or $R^b$ is 4- to 7-membered heterocyclyl optionally substituted with one or more hydroxy groups; or
$R^b$ is H, —$OR^c$; —$[CH_2—CH_2—O]_n$—H, —$[CH_2—CH_2—O]_m CH_3$ or heteroaryl optionally substituted with one or more $C_{1-4}$alkyl; wherein n and m are as defined before;
$R^c$ is H or hydroxy$C_{1-4}$alkyl;
$R^2$ is H, $C_{1-4}$alkoxy, halo-$C_{1-4}$alkoxy, halo, $C_{1-4}$alkyl, —S—$C_{1-4}$alkyl or —NH—$C_{1-4}$alkyl;
$R^4$ is H, halo, halo-$C_{1-4}$alkyl, $C_{1-4}$alkyl, $C_{3-5}$cycloalkyl;
$R^5$ is H, halo, CN, $C_{1-4}$alkoxy, hydroxy-$C_{1-4}$alkoxy, $C_{1-4}$alkoxy-$C_{1-4}$alkoxy, —CH=NH—O(hydroxy$C_{1-4}$alkyl); or
$R^5$ is $C_{2-6}$alkynyl optionally substituted with OH or $NR^gR^h$ wherein $R^g$ is and $R^h$ are independently H or $C_{1-4}$alkyl; or $R^g$ and $R^h$ form together with the nitrogen to which they are attached a 4- to 7-membered heterocyclyl optionally containing an additional heteroatom selected from O, S or N, wherein the heteroatom can be in its oxidized form; and wherein said heterocyclyl is optionally substituted with $C_{1-4}$alkyl;
$R^6$ is halo, $C_{1-4}$ alkyl or CN; or a pharmaceutically acceptable salt thereof.

In another embodiment, the invention provides a pharmaceutical composition comprising a therapeutically effective amount of a compound according to the definition of formula (I), or a pharmaceutically acceptable salt thereof, or subformulae II or III thereof and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae II or III thereof and one or more therapeutically active agent.

DETAILED DESCRIPTION

Figure 1:
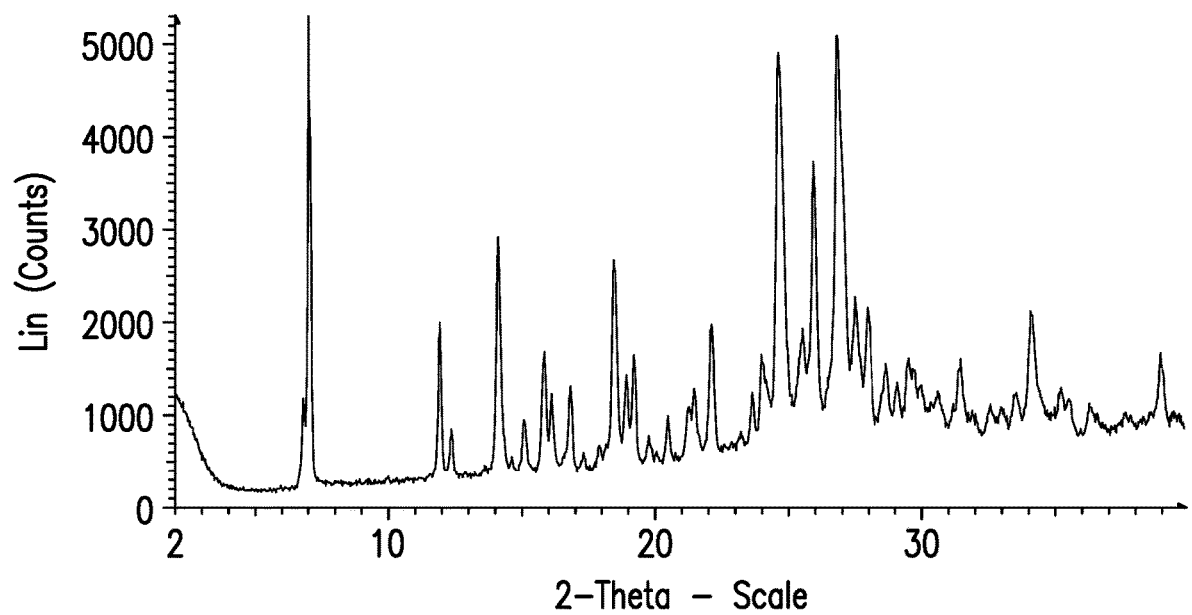
FIG. 1. illustrates the x-ray powder diffraction patterns of Example 1 hydrate form B.

In embodiment 1, the invention therefore provides a compound of the formula (I):

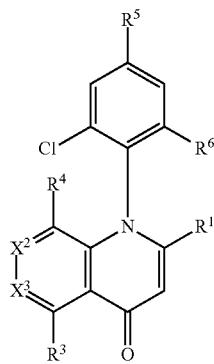

wherein:
$X^2$ is $CR^2$ or N;
$X^3$ is CH or N;
$R^1$ is $C_{1-4}$alkyl, —$CH_2CN$, —CN, $C_{1-4}$alkoxy$C_{1-4}$alkyl, halo-$C_{1-4}$alkyl, —CH=N—OH, —CH=N—O—$C_{1-4}$alkyl, —CH=N—O-(hydroxy$C_{1-4}$alkyl), hydroxy-$C_{1-4}$alkyl, —$CH_2OP(O)(OH)_2$ or $C_{3-5}$cycloalkyl;
$R^3$ is —$OR^a$, —$NHR^b$, —$C(O)NH_2$; —C(O)[hydroxy$C_{1-4}$ alkyl], heterocyclyl optionally substituted with one or more substituents independently selected from OH and hydroxy$C_{1-4}$alkyl; 5- or 6-membered ring heteroaryl optionally substituted with one or more $C_{1-4}$alkyl; or $R^3$ is $C_{1-4}$alkyl substituted with one or more substituents independently selected from —C(O)[hydroxy$C_{1-4}$alkyl] and —$OR^c$;
$R^a$ is —$C_{1-6}$alkyl substituted with one or more substituents independently selected from —$OR^c$, —$SO_2C_{1-4}$alkyl, —$NHS(O)_2C_{1-4}$alkyl and heterocyclyl which is further optionally substituted with one or more substituent independently selected from $C_{1-4}$alkyl or hydroxy$C_{1-4}$alkyl; or $R^a$ is H, —[$CH_2$—$CH_2$—O]$_n$—H, —[$CH_2$—$CH_2$—O]$_m$—$CH_3$ or heteroaryl optionally substituted with one or more $C_{1-4}$alkyl; wherein n is 2-6 and m is 1-6;
$R^b$ is —$C_{1-6}$alkyl substituted with one or more substituents independently selected from —$OR^c$, —C(O)NH—$C_{1-4}$alkyl, —C(O)NH-(hydroxy$C_{1-4}$alkyl), hydroxy$C_{1-4}$alkyl, 5- or 6-membered heteroaryl, heterocyclyl, —$SO_2C_{1-4}$alkyl and —$NHS(O)_2C_{1-4}$alkyl; or $R^b$ is —$S(O)_2$heteroaryl; or
$R^b$ is 4- to 7-membered heterocyclyl optionally substituted with one or more hydroxy groups; or
$R^b$ is H, —$OR^c$; —[$CH_2$—$CH_2$—O]$_n$—H, —[$CH_2$—$CH_2$—O]$_m$—$CH_3$ or heteroaryl optionally substituted with one or more $C_{1-4}$alkyl; wherein n and m are as defined before;
$R^c$ is H or hydroxy$C_{1-4}$alkyl;
$R^2$ is H, $C_{1-4}$alkoxy, halo-$C_{1-4}$alkoxy, halo, $C_{1-4}$alkyl, —S—$C_{1-4}$alkyl or —NH—$C_{1-4}$alkyl;
$R^4$ is H, halo, halo-$C_{1-4}$alkyl, $C_{1-4}$alkyl, $C_{3-5}$cycloalkyl;
$R^5$ is H, halo, CN, $C_{1-4}$alkoxy, hydroxy-$C_{1-4}$alkoxy, $C_{1-4}$alkoxy-$C_{1-4}$alkoxy, —CH=NH—O(hydroxy$C_{1-4}$alkyl); or
$R^5$ is $C_{2-6}$alkynyl optionally substituted with OH or $NR^gR^h$ wherein $R^g$ is and $R^h$ are independently H or $C_{1-4}$alkyl; or $R^g$ and $R^h$ form together with the nitrogen to which they are attached a 4- to 7-membered heterocyclyl optionally containing an additional heteroatom selected from O, S or N, wherein the heteroatom can be in its oxidized form; and wherein said heterocyclyl is optionally substituted with $C_{1-4}$alkyl;
$R^6$ is halo, $C_{1-4}$ alkyl or CN; or a pharmaceutically acceptable salt thereof.

Unless specified otherwise, the term "compounds of the present invention" or "compounds of the invention" refers to compounds of formula (I) and subformulae II or III thereof, and salts thereof, as well as all stereoisomers (including diastereoisomers and enantiomers), rotamers, tautomers and isotopically labeled compounds (including deuterium substitutions), as well as inherently formed moieties.

For purposes of interpreting this specification, the following definitions will apply unless specified otherwise and whenever appropriate, terms used in the singular will also include the plural and vice versa.

It must be noted that as used herein and in the appended claims, the singular forms "a", "an" and "the" include plural referents unless the context clearly dictates otherwise. Thus, for example, reference to "the compound" includes reference to one or more compounds; and so forth.

The term "alkyl" refers to a fully saturated branched or unbranched (or straight chain or linear) hydrocarbon moiety, comprising 1 to 6 carbon atoms. Preferably the alkyl comprises 1 to 4 carbon atoms. $C_{1-4}$alkyl refers to an alkyl chain comprising 1 to 4 carbons. $C_{1-6}$alkyl refers to an alkyl chain comprising 1 to 6 carbons.

As used herein, the term "haloalkyl" (i.e. halo-$C_{1-4}$alkyl) refers to an alkyl (i.e. $C_{1-4}$alkyl) as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "halo-$C_{1-4}$alkyl" refers to a hydrocarbon having one to four carbon atoms and being substituted by one or more halo groups.

As used herein, the term "hydroxyalkyl" (i.e. hydroxy-$C_{1-4}$alkyl) refers to an alkyl (i.e. $C_{1-4}$alkyl) as defined herein, that is substituted by one or more hydroxy groups as defined herein.

As used herein, the term "alkoxyalkyl" (i.e. $C_{1-4}$alkoxy$C_{1-4}$alkyl) refers to an alkyl (i.e. $C_{1-4}$alkyl) defined herein, that is substituted by one or more alkoxy groups (i.e. $C_{1-4}$alkoxy) as defined herein.

As used herein, the term "alkoxy" (i.e. refers to the radical alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-8, more preferably about 1-4 carbons.

As used herein, the term "haloalkoxy" (i.e. halo-$C_{1-4}$alkoxy) refers to an alkoxy as defined herein, that is substituted by one or more halo groups as defined herein.

As used herein, the term "$C_{3-5}$cycloalkyl" refers to saturated or unsaturated but non-aromatic monocyclic hydrocarbon groups of 3-5 carbon atoms. Exemplary monocyclic hydrocarbon groups include cyclopropyl, cyclobutyl, cyclopentyl, or cyclopentenyl.

The term heteroaryl includes monocyclic heteroaryl, containing from 5 or 6 ring members selected from carbon atoms and 1 to 4 heteroatoms, and each heteroatoms is independently selected from O, N or S wherein S and N may be oxidized to various oxidation states. The heteroaryl radical may be bonded via a carbon atom or a heteroatom (e.g. via N). Typical monocyclic heteroaryl groups include thienyl, furyl, pyrrolyl, imidazolyl, pyrazolyl, thiazolyl, isothiazolyl, oxa-2,3-diazolyl, oxa-2,4-diazolyl, oxa-2,5-diazolyl, oxa-3,4-diazolyl, thia-2,3-diazolyl, thia-2,4-diazolyl, thia-2,5-diazolyl, thia-3,4-diazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

As used herein, and unless otherwise specified, the term "heterocyclyl" refers to an optionally substituted, saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. The heterocyclyl radical may be bonded via a carbon atom or a heteroatom (e.g. N). In one embodiment, heterocyclyl moiety represents a saturated monocyclic ring containing from 4-7 ring atoms and optionally containing a further heteroatom, selected from O, S or N. The heterocyclic group can be attached at a heteroatom or a carbon atom. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

Various (enumerated) embodiments of the invention are described herein. It will be recognized that features specified in each embodiment may be combined with other specified features to provide further embodiments of the present invention.

In embodiment 2, the invention pertains to a compound according to embodiment 2, having formula II:

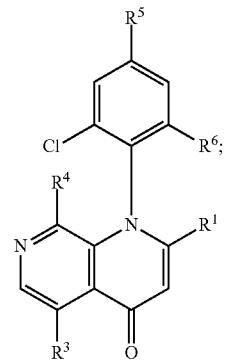

or a pharmaceutically acceptable salt thereof wherein $R^1$ and $R^3$-$R^6$ are as defined in embodiment 1.

In embodiment 3, the invention pertains to a compound according to embodiment 1 having formula III:

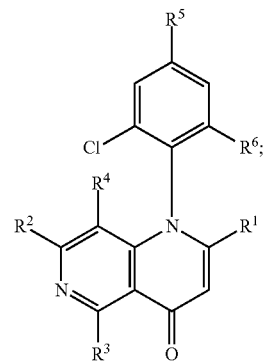

or a pharmaceutically acceptable salt thereof, wherein $R^1$-$R^6$ are as defined in embodiment 1.

In embodiment 4, the invention pertains to a compound according to any one of embodiments 1 to 3 wherein $R^1$ is $CH_3$, cyclopropyl —$CH_2OH$ or CH=NH—OH; or a pharmaceutically acceptable salt thereof.

In embodiment 4A, the invention pertains to a compound according to embodiment 4, wherein is $CH_3$ or —$CH_2OH$; or a pharmaceutically acceptable salt thereof. In embodiment 4B, the invention pertains to a compound according to embodiment 4, wherein $R^1$ is —$CH_2OH$; or a pharmaceutically acceptable salt thereof.

In embodiment 5, the invention pertains to a compound according to any one of embodiments 1, 3, 4, 4A and 4B wherein $R^2$ is H or —NH—$CH_3$; or a pharmaceutically acceptable salt thereof.

In embodiment 5A, the invention pertains to a compound according to embodiment 5 wherein $R^2$ is H; or a pharmaceutically acceptable salt thereof.

In embodiment 6, the invention pertains to a compound according to any one of embodiments 1-5, 4A, 4B and 5A wherein $R^4$ is H or halo; or a pharmaceutically acceptable salt thereof.

In embodiment 6A, the invention pertains to a compound according to embodiment 6 wherein $R^4$ is Cl; or a pharmaceutically acceptable salt thereof.

In embodiment 7, the invention pertains to a compound according to any one of embodiments 1-6, 4A, 4B, 5A and 6A wherein $R^5$ is H, F, CN, $C_{2-4}$alkynyl substituted with OH or thiomorpholine; or a pharmaceutically acceptable salt thereof.

In embodiment 7A, the invention pertains to a compound according to embodiment 7 wherein $R^5$ is H, F or CN; or a pharmaceutically acceptable salt thereof.

In embodiment 8, the invention pertains to a compound according to any one of embodiments 1-7, 4A, 4B, 5A, 6A and 7A wherein $R^6$ is Cl or CN; or a pharmaceutically acceptable salt thereof.

In embodiment 8A, the invention pertains to a compound according to embodiment 7 wherein $R^6$ is Cl; or a pharmaceutically acceptable salt thereof.

In embodiment 9, the invention pertains to a compound according to any one of embodiments 1-8, 4A, 4B, 5A, 6A, 7A and 8A wherein $R^3$ is hydroxyC$_{1-6}$alkyl, hydroxyC$_{1-6}$alkoxy, —O—(CH$_2$CH$_2$—O)$_n$H, —O—(CH$_2$CH$_2$—O)$_m$CH$_3$, —NH—(CH$_2$CH$_2$O)$_n$H, —NH—(CH$_2$CH$_2$—O)$_m$CH$_3$, azetidine substituted with hydroxyl, pyrrolidine substituted with one or more substitutents independently selected from hydroxyl and hydroxyC$_{1-4}$alkyl; or piperazine substituted with hydroxyC$_{1-4}$alkyl; or a pharmaceutically acceptable salt thereof.

In embodiment 10, the invention pertains to a compound according to any one of embodiments 1-8, 4A, 4B, 5A, 6A, 7A and 8A wherein $R^3$ is selected from the following groups:

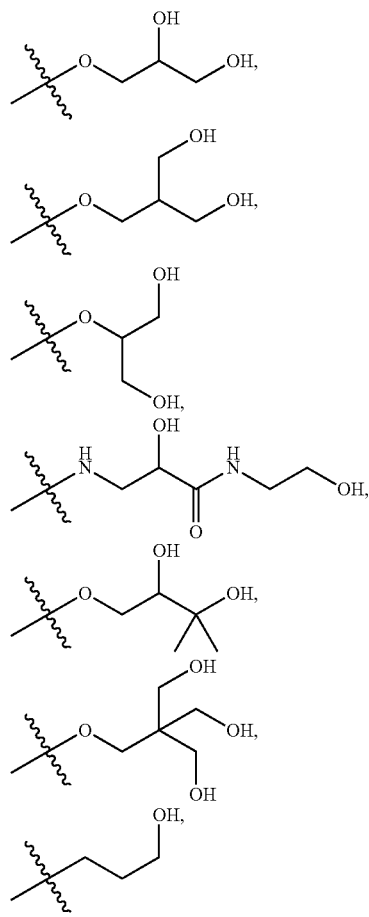

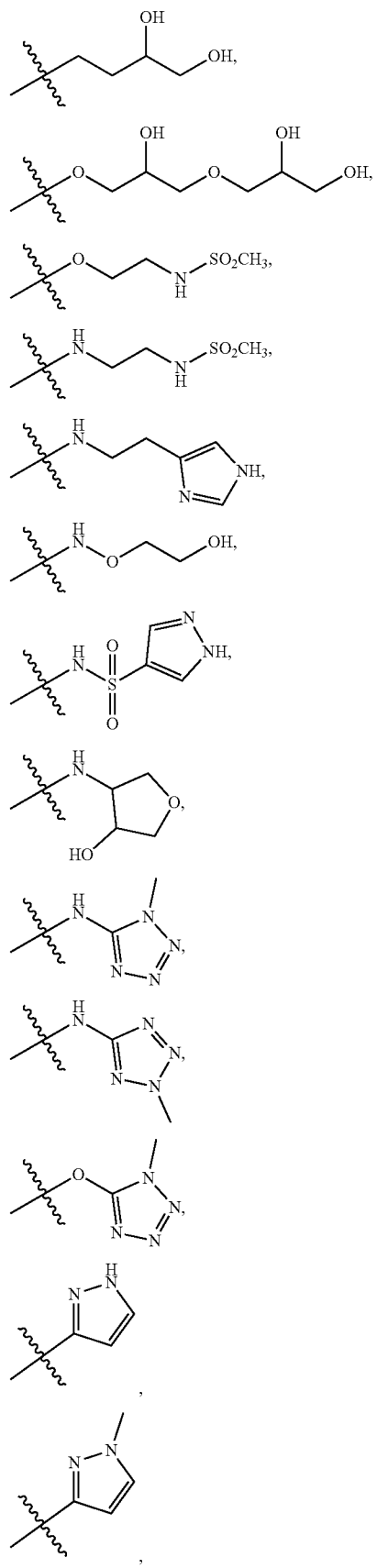

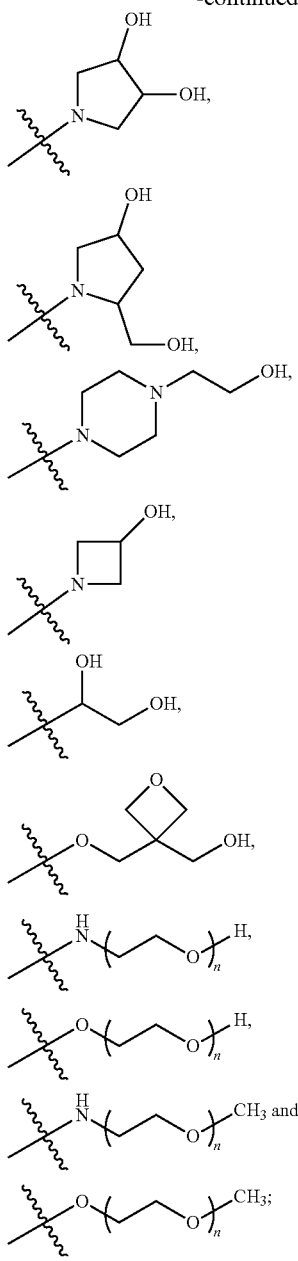
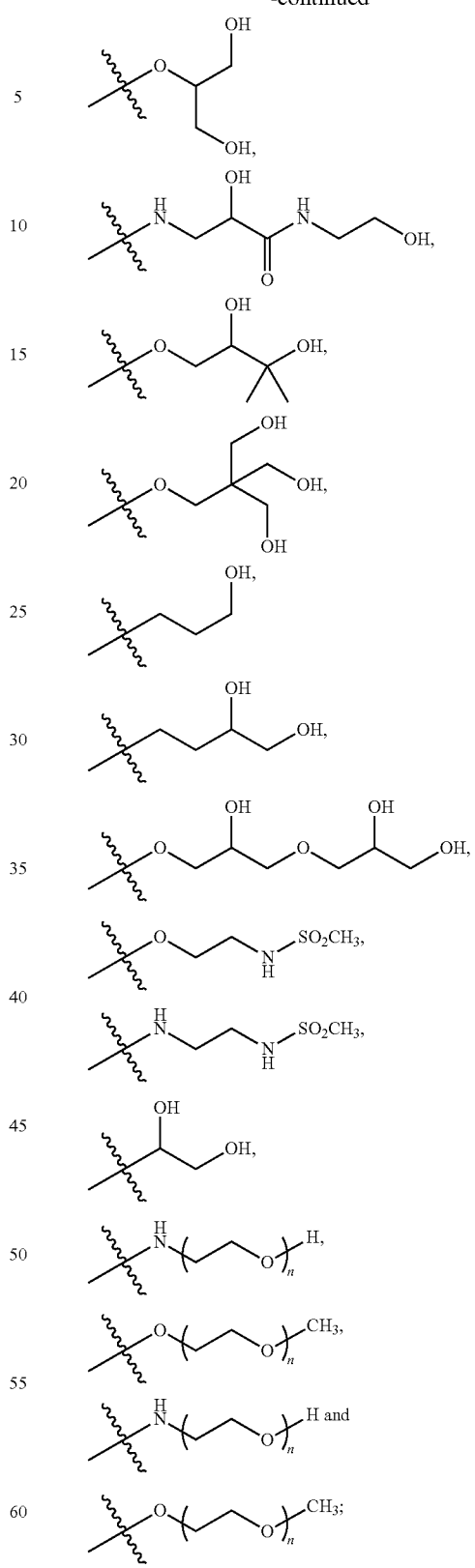
or a pharmaceutically acceptable salt thereof.
In embodiment 10A, the invention pertains to a compound according to embodiment 10 wherein $R^3$ is selected from the following groups:
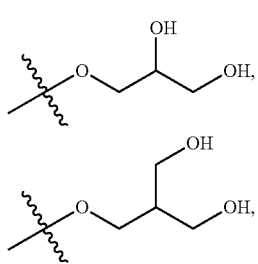
or a pharmaceutically acceptable salt thereof.
In embodiment 11, the invention pertains to a compound according to embodiment 10 wherein $R^3$ is selected from:

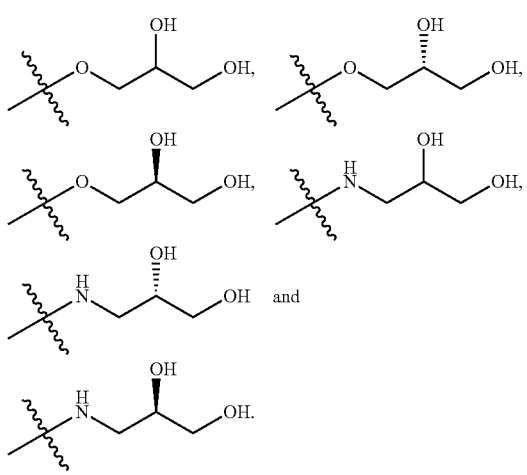

In embodiment 12, the invention pertains to a compound of Formula III wherein $R^1$ is $CH_3$ or $CH_2OH$, $R^2$ is H, $R^3$ is —$OR^a$ or —$NHR^b$, $R^4$ is Cl, $R^5$ is H or F and $R^6$ is Cl; or a pharmaceutically acceptable salt thereof.

In embodiment 13, the invention pertains to a compound selected from the group consisting of specific compounds described in the examples 1 to 93 below; or a pharmaceutically acceptable salt thereof.

In embodiment 13A, the invention pertains to a compound selected from the group consisting of:
8-Chloro-1-(2,6-dichlorophenyl)-2-(hydroxymethyl)-5-((3-(hydroxymethyl)oxetan-3-yl)methoxy)-1,6-naphthyridin-4(1H)-one;
N-(2-((8-Chloro-1-(2,6-dichlorophenyl)-2-(hydroxymethyl)-4-oxo-1,4-dihydro-1,6-naphthyridin-5-yl)oxy)ethyl)methanesulfonamide;
8-Chloro-1-(2,6-dichlorophenyl)-5-(3-hydroxy-2-(hydroxymethyl)propoxy)-2-(hydroxymethyl)-1,6-naphthyridin-4(1H)-one;
8-Chloro-1-(2,6-dichlorophenyl)-2-(hydroxymethyl)-5-((2-(methylsulfonyl)ethyl)amino)-1,6-naphthyridin-4(1H)-one;
8-Chloro-1-(2,6-dichlorophenyl)-5-(2,3-dihydroxypropoxy)-4-oxo-1,4-dihydro-1,6-naphthyridine-2-carbonitrile;
8-Chloro-1-(2,6-dichlorophenyl)-5-(2,3-dihydroxy-3-methylbutoxy)-2-methyl-1,6-naphthyridin-4(1H)-one;
8-Chloro-1-(2,6-dichlorophenyl)-5-(2,3-dihydroxpropyl)-2-(hydroxymethyl)-1,6-naphthyridin-4(1H)-one;
8-Chloro-1-(2,6-dichlorophenyl)-5-(1,2-dihydroxyethyl)-2-(hydroxymethyl)-1,6-naphthyridin-4(1H)-one; and
8-Chloro-1-(2,6-dichlorophenyl)-5-(3,4-dihydroxybutyl)-2-(hydroxymethyl)-1,6-naphthyridin-4(1H)-one; or a pharmaceutically acceptable salt thereof.

In embodiment 13B, the invention pertains to a compound selected from the group consisting of:
(R)-8-Chloro-1-(2,6-dichlorophenyl)-5-(2,3-dihydroxy-3-methylbutoxy)-2-methyl-1,6-naphthyridin-4(1H)-one;
(S)-8-Chloro-1-(2,6-dichlorophenyl)-5-(2,3-dihydroxy-3-methylbutoxy)-2-methyl-1,6-naphthyridin-4(1H)-one; and
8-Chloro-1-(2,6-dichlorophenyl)-5-(2,3-dihydroxy-3-methylbutoxy)-2-methyl-1,6-naphthyridin-4(1H)-one; or a pharmaceutically acceptable salt thereof.

In embodiment 13C, the invention pertains to a compound selected from the group consisting of:
(S)-8-Chloro-1-(2,6-dichlorophenyl)-5-(2,3-dihydroxypropoxy)-2-(hydroxymethyl)-1,6-naphthyridin-4(1H)-one;
(R)-8-chloro-1-(2,6-dichlorophenyl)-5-(2,3-dihydroxypropoxy)-2-(hydroxymethyl)-1,6-naphthyridin-4(1H)-one;
8-chloro-1-(2,6-dichlorophenyl)-5-(2,3-dihydroxypropoxy)-2-(hydroxymethyl)-1,6-naphthyridin-4(1H)-one; or a pharmaceutically acceptable salt thereof.

In embodiment 13D, the invention pertains to a compound selected from the group consisting of:
(R)-8-Chloro-1-(2,6-dichlorophenyl)-5-(3,4-dihydroxybutyl)-2-(hydroxymethyl)-1,6-naphthyridin-4(1H)-one;
(S)-8-Chloro-1-(2,6-dichlorophenyl)-5-(3,4-dihydroxybutyl)-2-(hydroxymethyl)-1,6-naphthyridin-4(1H)-one; and
8-Chloro-1-(2,6-dichlorophenyl)-5-(3,4-dihydroxybutyl)-2-(hydroxymethyl)-1,6-naphthyridin-4(1H)-one; or a pharmaceutically acceptable salt thereof.

In embodiment 13E, the invention pertains to a compound selected from the group consisting of:
(R)-8-Chloro-1-(2,6-dichlorophenyl)-5-(2,3-dihydroxypropyl)-2-(hydroxymethyl)-1,6-naphthyridin-4(1H)-one;
(S)-8-Chloro-1-(2,6-dichlorophenyl)-5-(2,3-dihydroxpropyl)-2-(hydroxymethyl)-1,6-naphthyridin-4(1H)-one; and
8-Chloro-1-(2,6-dichlorophenyl)-5-(2,3-dihydroxypropyl)-2-(hydroxymethyl)-1,6-naphthyridin-4(1H)-one; or a pharmaceutically acceptable salt thereof.

In embodiment 13F, the invention pertains to a compound selected from the group consisting of:
(R)-8-Chloro-1-(2,6-dichlorophenyl)-5-(1,2-dihydroxyethyl)-2-(hydroxymethyl)-1,6-naphthyridin-4(1H)-one;
(S)-8-Chloro-1-(2,6-dichlorophenyl)-5-(1,2-dihydroxyethyl)-2-(hydroxymethyl)-1,6-naphthyridin-4(1H)-one; and
8-Chloro-1-(2,6-dichlorophenyl)-5-(1,2-dihydroxyethyl)-2-(hydroxymethyl)-1,6-naphthyridin-4(1H)-one; or a pharmaceutically acceptable salt thereof.

In embodiment 14, the invention is a hydrate crystalline form B of Example 1.

In embodiment 15, the invention is a hydrate crystalline form B of Example 1 characterized by a x-ray powder diffraction pattern comprising four or more 2θ values (CuKα λ=1.5418 Å) selected from the group consisting of 14.294±0.2°, 18.666±0.2°, 22.353±0.2°, 24.878±0.2°, 26.163±0.2°, 27.106±0.2°, 27.744±0.2° and 28.228±0.2° measured at a temperature of about 22° C. and an x-ray wavelength, λ, of 1.5418 Å.

In embodiment 16, the invention is a hydrate crystalline form B of Example 1 characterized by a x-ray powder diffraction pattern comprising five or more 2θ values (CuKα λ=1.5418 Å) selected from the group consisting of 14.294±0.2°, 18.666±0.2°, 22.353±0.2°, 24.878±0.2°, 26.163±0.2°, 27.106±0.2°, 27.744±0.2° and 28.228±0.2° measured at a temperature of about 22° C. and an x-ray wavelength, 2, of 1.5418 Å.

In embodiment 17, the invention is a hydrate crystalline form B of Example 1 having an X-ray diffraction spectrum substantially the same as the X-ray powder diffraction spectrum shown in FIG. 1.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Occasionally, the variability could be higher than 0.2° depending on apparatus calibration differences.

Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Figure 2:
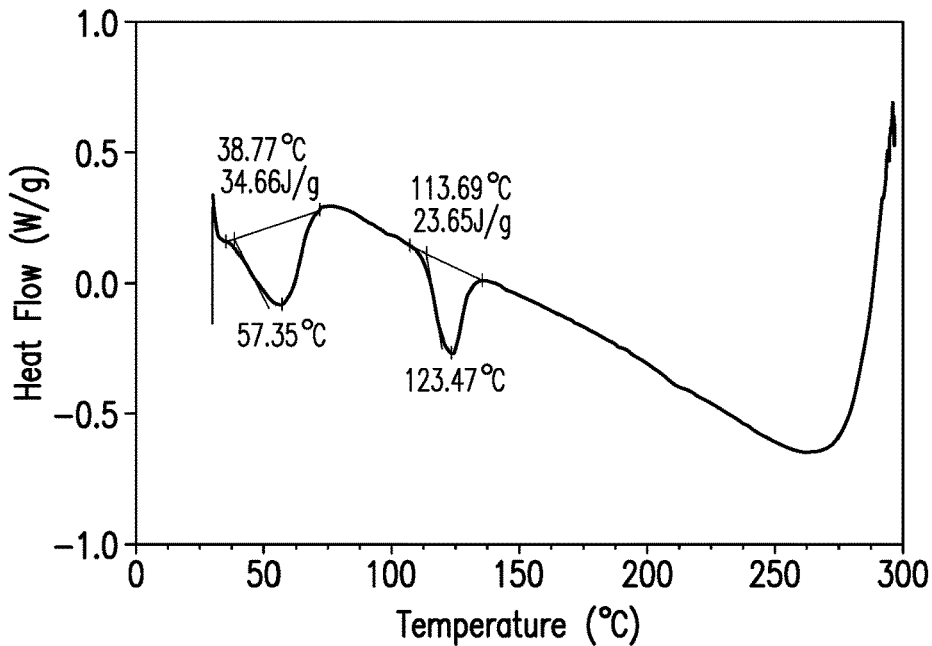
FIG. 2. illustrates the differential scanning calorimetry (DSC) of example 1 hydrate form B with pinhole sample pan FIG. 3. illustrates the differential scanning calorimetry (DSC) of example 1 hydrate form B with hermetic sample pan FIG. 4. Illustrates thermogravimetric analysis (TGA) of Example 1 hydrate form B.
Figure 3:
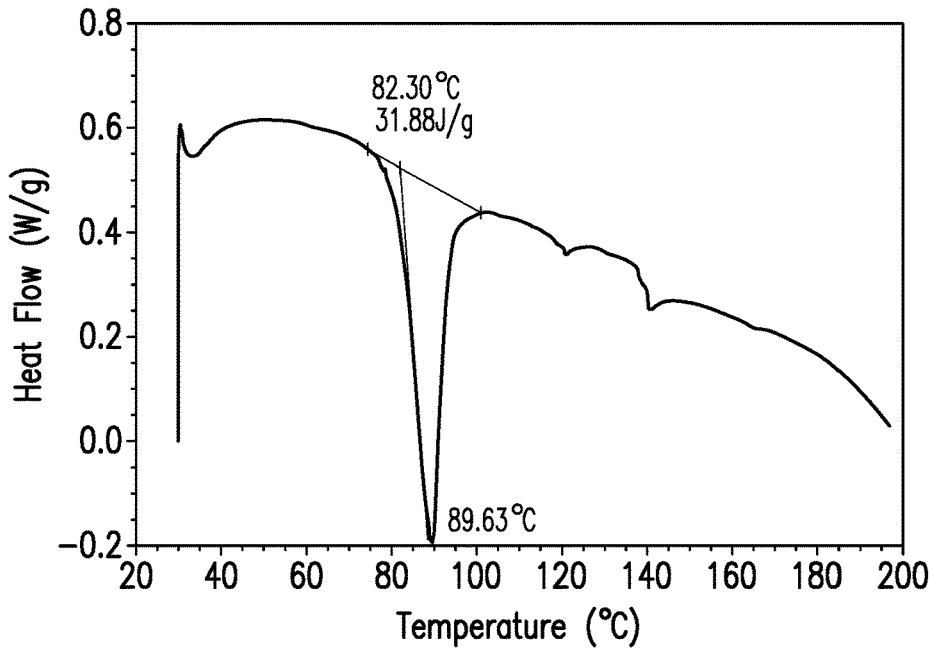

In embodiment 18, the invention is a hydrate crystalline form B of Example 1 having a differential scanning calorimetry (DSC) thermogram substantially the same as that shown in shown in FIG. 2 (with pinhole sample pan) and FIG. 3 (with hermetic sample pan).

Figure 4:
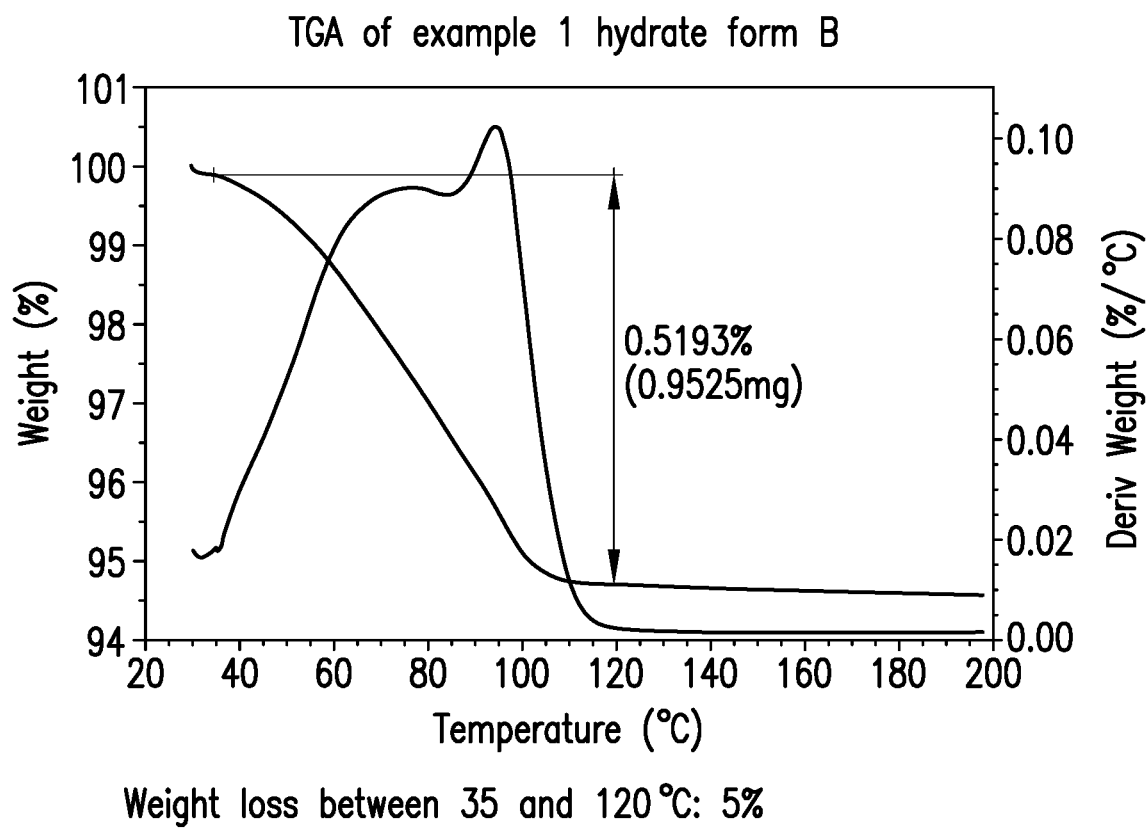

In embodiment 19, the invention is a hydrate crystalline form B of Example 1 having a thermo gravimetric analysis (TGA) diagram substantially the same as that shown in shown in FIG. 4.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number.

Isotopes that can be incorporated into compounds of the invention include, for example, isotopes of hydrogen.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the formula (I), (II) or (III). The concentration of deuterium may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively.

Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by GIRK1/4 channel, or (ii) associated with GIRK1/4 channel activity, or (iii) characterized by activity (normal or abnormal) of GIRK1/4 channel; or (2) reduce or inhibit the activity of GIRK1/4 channel; or (3) reduce or inhibit the expression of GIRK1/4 channel. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of GIRK1/4 channel; or at least partially reducing or inhibiting the expression of GIRK1/4 channel.

As used herein, the term "subject" refers to humans, male or female. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid.

In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols). For example, solubility can be increased by esterification of a hydroxy group with phosphoric acid.

Exemplary prodrugs are, e.g., O-acyl or O-phosphate derivatives of alcohols or phenols, wherein acyl has a meaning as defined herein. Suitable acids for formation of the O-acyl prodrugs are e.g. substituted or unsubstituted alkyl-, cycloalkyl- or benzyl-carboxylic acids. Amines have been masked as arylcarbonyloxymethyl substituted derivatives which are cleaved by esterases in vivo releasing the free drug and formaldehyde (Bundgaard, J. Med. Chem. 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers, vicinal diols have been masked as cyclic acetals or ketals. Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

In one embodiment, the compound of Formula (I), (II) or (III) is in a hydrate form.

Typically, the compounds of formula (I), (II) or (III) can be prepared according to the Schemes B, C D provided infra. The required intermediates J are prepared as described below in Scheme A.

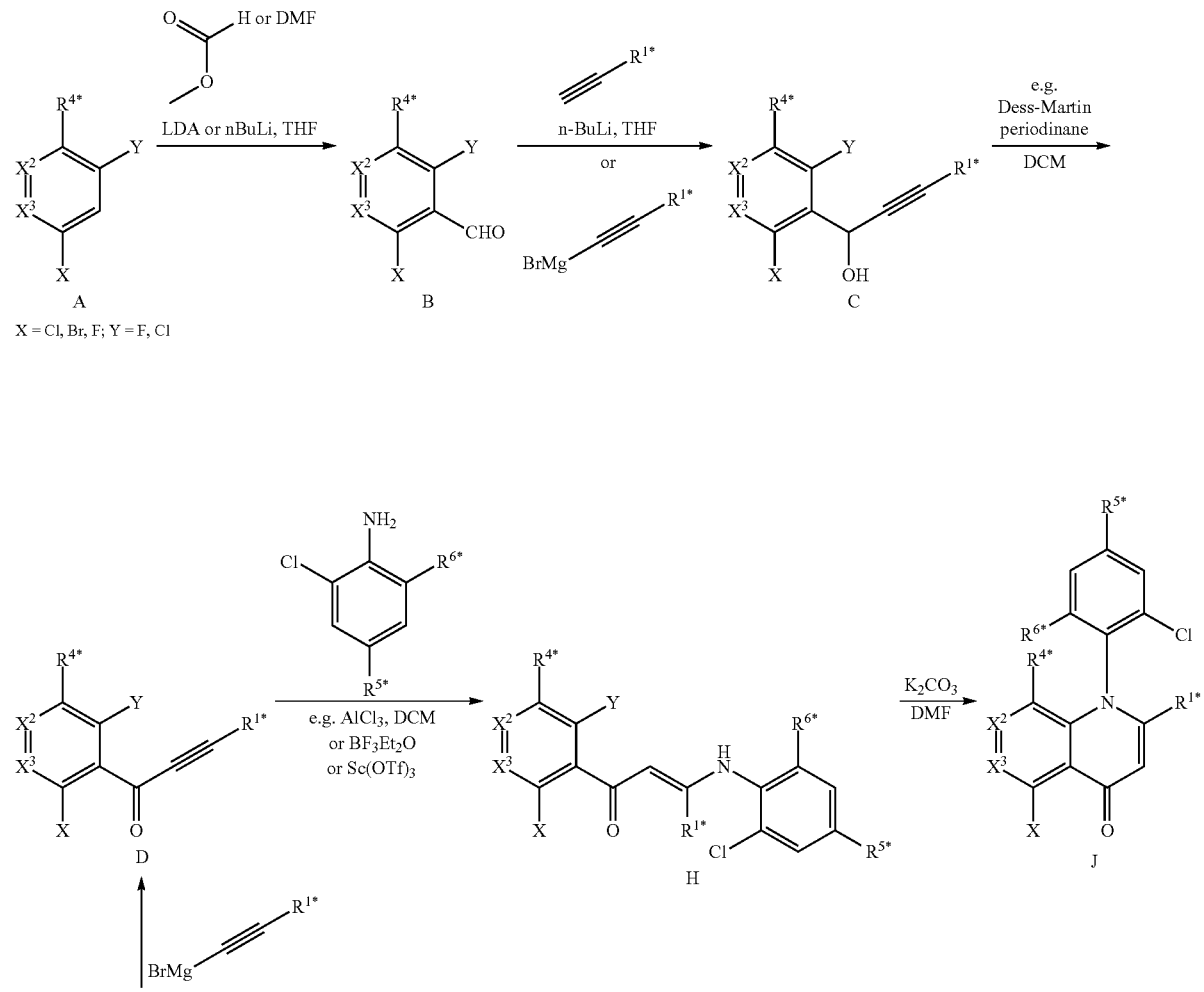

-continued

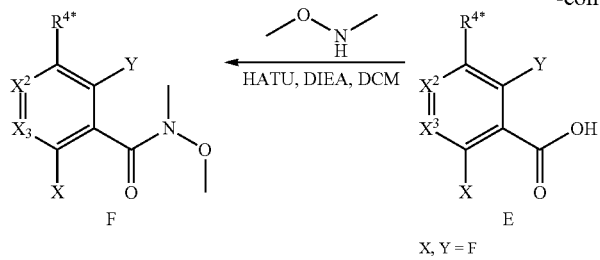

X, Y = F

In scheme A the aromatic starting material A is deprotonated by a strong base (e.g. LDA or n-BuLi) and reacted with e.g. alkyl formate or DMF to yield the aromatic aldehyde. The aldehyde B can be reacted with a deprotonated alkyne (e.g a Grignard reagent or a lithiated species) to furnish the benzyl alcohols C which are oxidized to the ketone under appropriate oxidizing conditions such as the Dess-Martin periodinane reagent. Alternatively, ketones D can be prepared from the aromatic acids E which are coupled with an amine to form amides F which are substrate for the reaction with appropriate Grignard reagents. Reaction of an aniline under Lewis-catalysis (e.g. $AlCl_3$, $BF_3 \cdot Et_2O$, $Sc(OTf)_3$) provides intermediates H which can be cyclized to the annelated 4-pyridones under basic conditions (e.g. potassium carbonate).

$X^2$, $X^3$ are as defined in the Summary of the Invention and $R^{1*}$, $R^{4*}$, $R^{5*}$ and $R^{6*}$ include the definitions for $R^1$, $R^4$, $R^5$ and $R^6$ as defined in the Summary of the Invention but can be also substituents which can be transformed into $R^1$, $R^4$, $R^5$ and $R^6$.

Scheme B describes the synthesis of compound of Formula I, in particular compounds of Formula (I) wherein $R^1$ is $CH_2OH$, $CHF_2$, CHO, CN, $CH_3$, $R^3$ is —$OR^a$ or —$NHR^b$ and/or $R^2$ is $C_{1-4}$alkoxy, halo$C_{1-4}$alkoxy and —NH—$C_{1-4}$alkyl.

Scheme B

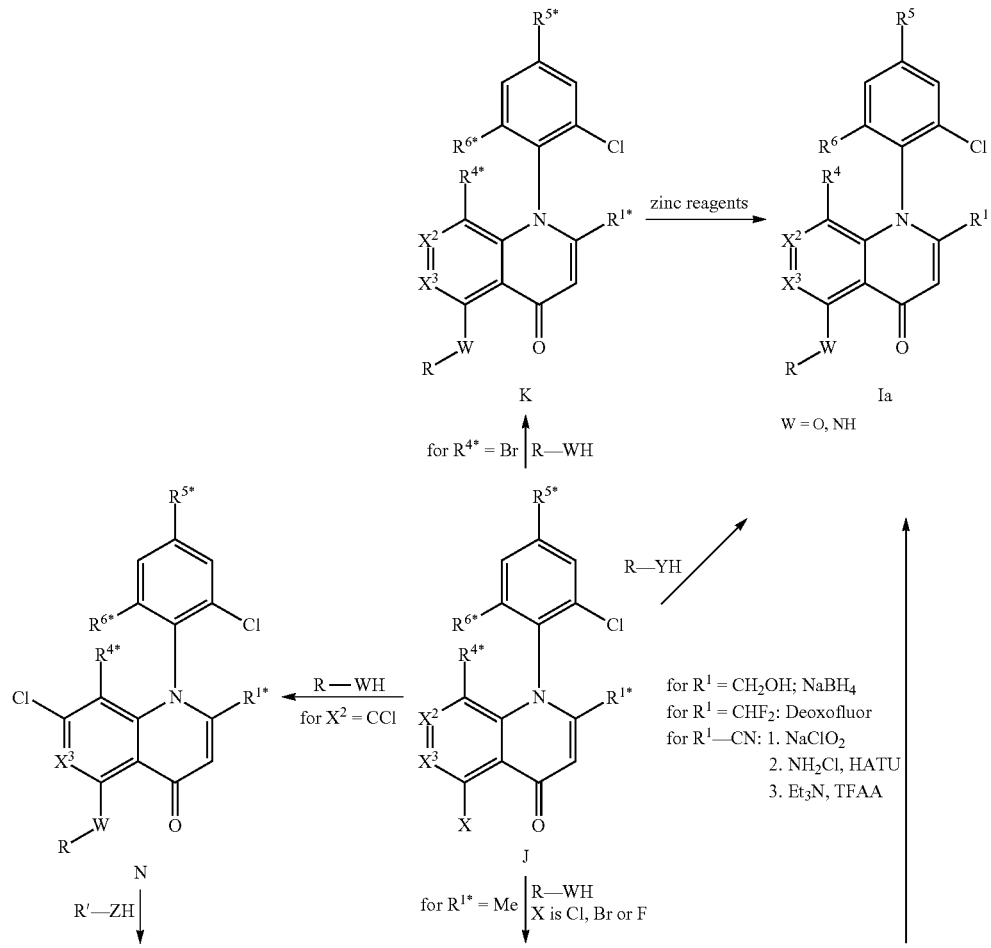

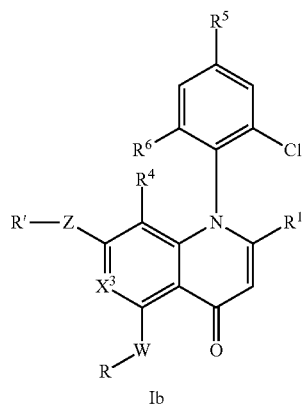

Ib

W = O, NH
Z = O, NH, CH$_2$

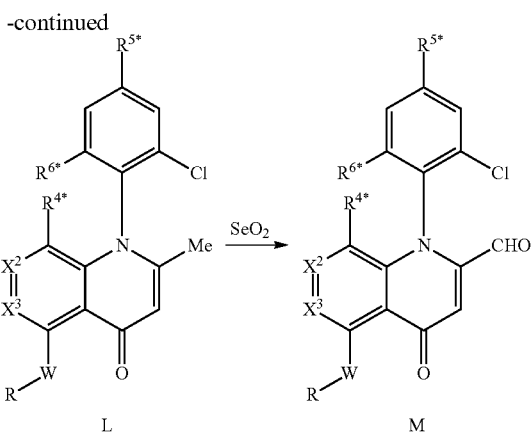

R' is chosen so that R'Z is part of R$^2$ as defined in Formula I
R is chosen so that RW is part of R$^3$ as defined in Formula I Examples of the general formula Ia and Ib can be prepared as described in Scheme B. Intermediates J can be converted directly to compounds Ia by nucleophilic aromatic substitution with amines and alcohols and—if necessary—subsequent protecting group manipulations. For intermediates K the substituent R$_4$ can be introduced e.g by reaction with zinc reagents or Suzuki coupling with boronic acids. For intermediates L the methyl group can be oxidized with selenium dioxide to the aldehyde which can be converted to a primary alcohol be e.g. NaBH$_4$ reduction. The aldehyde functionality can also be transformed into a difluoromethyl group by fluorination with a suitable fluorination agent. Further, the aldehyde group can be transformed into a nitrile by a sequence of reactions involving oxidation to the acid, formation of the amide and dehydration. For intermediates N with X$^2$=CCl a second nucleophilic aromatic substitution with alcohols, amines, Grignard or zinc reagents can lead to compounds of the general formula Ib. Scheme C describes the introduction of various R$^3$ groups different from the ones described in Scheme B.

Scheme C

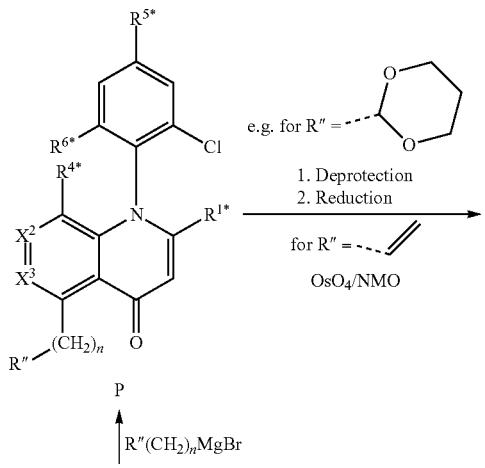

-continued

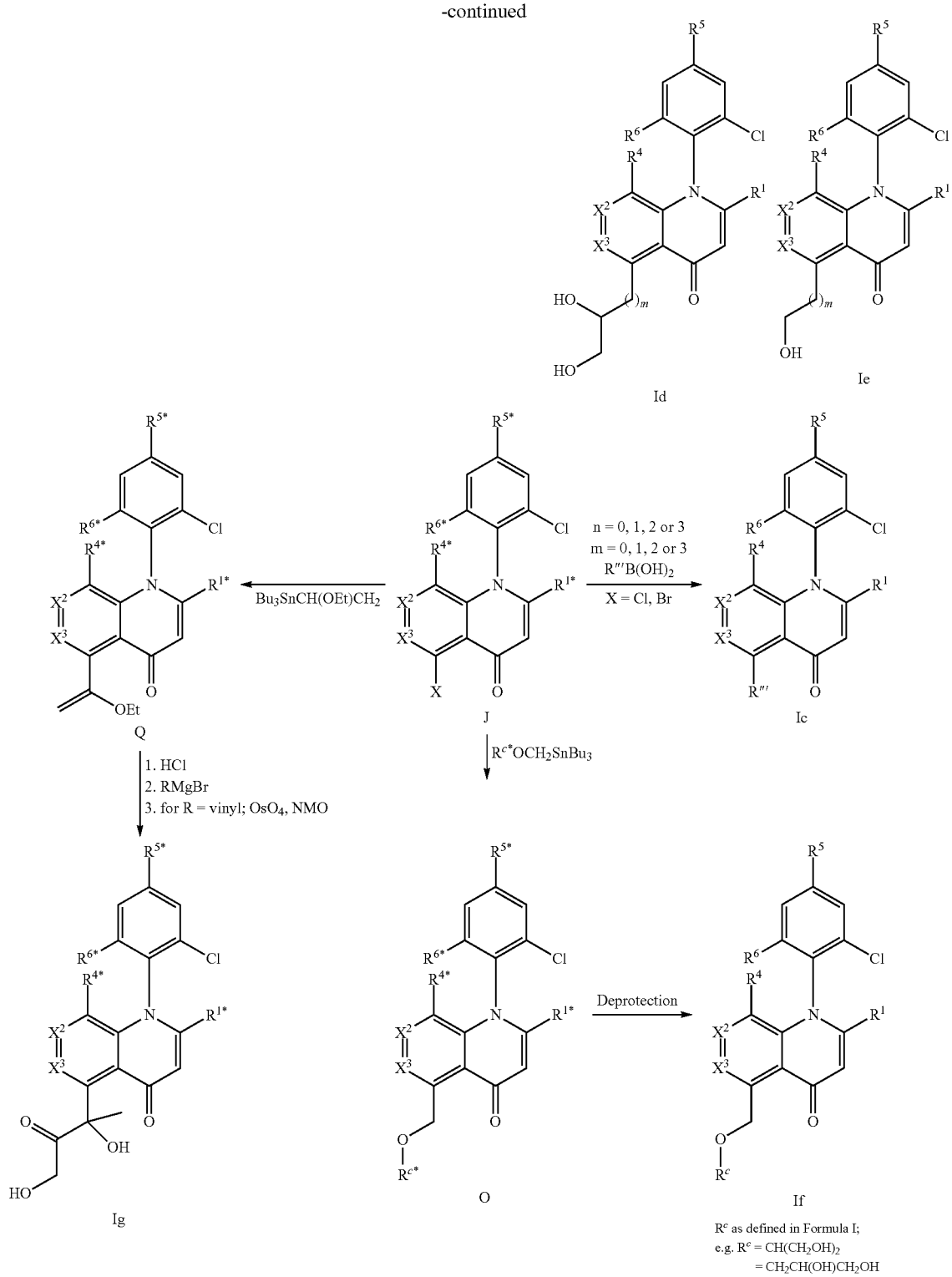

According to Scheme C, intermediates J can be coupled via Pd-catalyzed Suzuki coupling with boronic acids to examples of the general formula Ic where R is connected to the ring system via a C—C bond. Alternatively, intermediates J can also react with Grignard reagents to compounds P which can be transformed to examples of the formula Id and Ie by the conditions indicated in the scheme. Reaction of intermediates J with stannanes provides e.g. intermediates O and Q which can be transformed via a set of conditions to further examples of the general formula If and Ig.

Scheme D describes the synthesis of compound of Formula I wherein $R^5$ is $C_{2-6}$alkynyl.

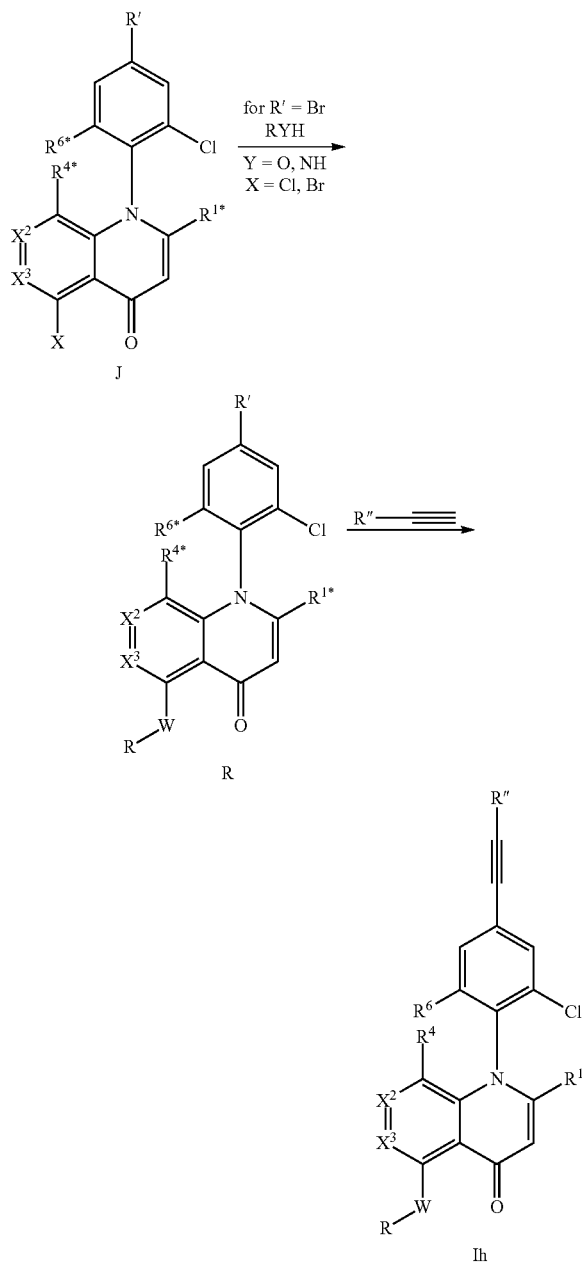

Scheme D

R is chosen so that RW is part of of $R^3$ as defined ain Formula I
R″ is chosen so that —CC—R″ is part of $R^5$ as defined in Formula I Intermediates J can be transformed to compounds R by nucleophilic aromatic substitution. Reaction with terminal alkynes via Pd/Cu-catalysis (Sonogashira coupling) and—if necessary-subsequent protecting group manipulations yields examples of the general formula Ih.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Method of the Invention

The compounds of any one of formulae I to III in free form or in pharmaceutically acceptable salt form, exhibit valuable pharmacological properties, e.g. GIRK1/4 channel modulating properties, e.g. as indicated in vitro and in vivo tests as provided in the next sections, and are therefore indicated for therapy or for use as research chemicals, e.g. as tool compounds.

As previously described, GIRK1/4 has been identified as a desirable anti-arrhythmia target for atrial fibrillation.

Additionally, GIRK1/4 blockers has been described as potentially useful in Sinoatrial/atrioventricular node dysfunction: GIRK1/4 channels mediate repolarization of the spontaneously depolarizing cells of the sinoatrial (SAN) and atrioventricular (AVN) nodes. Acetylcholine released from vagal nerve efferents binds to M2 muscarinic receptors present in these tissues, which in turn act upon GIRK1/4 channels to open them and permit potassium ion efflux from the cell. This repolarization (or hyperpolarization depending on the magnitude of efflux) determines the timing between spontaneous depolarizations, and hence heart rate and AV nodal conduction rate. Blockade of GIRK1/4 channels is expected to oppose the negative chronotropic effects of acetylcholine, and this has been observed with the selective peptide GIRK1/4 blocker tertiapin (Drici et al., 2000. The bee venom peptide tertiapin underlines the role of I(KACh) in acetylcholine-induced atrioventricular blocks. British journal of pharmacology 131, 569-577). In human diseases of pacemaking (e.g. sick sinus syndrome) the sinoatrial or atrioventricular nodes are dysfunctional, which can induce a variety of arrhythmias including bradycardia and asystoles. GIRK1/4 blockade may be expected to ameliorate such arrhythmias. For example, in a recent study, genetic deletion of GIRK4 was shown to rescue the failure of cardiac impulse generation and conduction induced by heart-specific silencing of the so-called "funny current", which mediates spontaneous depolarization in sinoatrial and atrioventricular tissue (Mesirca et al., 2014. Cardiac arrhythmia induced by genetic silencing of 'funny' (f) channels is rescued by GIRK4 inactivation. Nature communications 5, 4664).

Furthermore, GIRK1/4 blockers has been described as potentially useful in primary hyperaldosteronism: Somatic and germline gain-of-function mutations in KCNJ5 (encoding GIRK4) have recently been implicated in primary aldosteronism, a condition that induces hypertension. These mutations alter the selectivity filter of the GIRK4 channel and permit sodium ion influx into certain adrenal cells. The resulting cellular depolarization permits calcium influx, which in turn enhances aldosterone production and secretion, and may also induce cellular proliferation to produce an aldosterone-secreting adenoma (Scholl and Lifton, 2013. New insights into aldosterone-producing adenomas and hereditary aldosteronism: mutations in the K+ channel KCNJ5. Current opinion in nephrology and hypertension 22, 141-147). It is therefore possible that a selective GIRK4 blocker may prevent sodium ion influx, and its attendent promotion of aldosterone secretion in these patients.

Therefore, the compounds of the invention may be useful in the treatment of an indication selected from cardiac arrhythmia, atrial fibrillation, primary hyperaldosteronism, hypertension and sick sinus syndrome.

Thus, as a further embodiment, the present invention provides the use of a compound of any one of formulae (I) to (III) in therapy. In a further embodiment, the therapy is selected from a disease which may be treated by inhibition of GIRK1/4 channel. In another embodiment, the disease is selected from cardiac arrhythmia, atrial fibrillation, primary hyperaldosteronism, hypertension and sick sinus syndrome, suitably atrial fibrillation.

Thus, as a further embodiment, the present invention provides a compound of any one of formulae (I) to (III) for use in therapy. In a further embodiment, the therapy is selected from a disease which may be treated by inhibition of GIRK1/4 channel. In another embodiment, the disease is selected from cardiac arrhythmia, atrial fibrillation, primary hyperaldosteronism, hypertension and sick sinus syndrome, suitably atrial fibrillation.

In another embodiment, the invention provides a method of treating a disease which is treated by inhibition of GIRK1/4 channel, comprising administration of a therapeutically acceptable amount of a compound of any of formulae (I) to (III). In a further embodiment, the disease is selected from cardiac arrhythmia, atrial fibrillation, primary hyperaldosteronism, hypertension and sick sinus syndrome, suitably atrial fibrillation.

Thus, as a further embodiment, the present invention provides the use of a compound of any one of formulae (I) to (III) for the manufacture of a medicament. In a further embodiment, the medicament is for treatment of a disease which may be treated by inhibition of GIRK1/4 channel. In another embodiment, the disease is selected from cardiac arrhythmia, atrial fibrillation, primary hyperaldosteronism, hypertension and sick sinus syndrome, suitably atrial fibrillation.

In one embodiment of the present invention, there is provided (S)-8-Chloro-1-(2,6-dichlorophenyl)-5-(2,3-dihydroxypropoxy)-2-(hydroxymethyl)-1,6-naphthyridin-4 (1H)-one; or a pharmaceutically acceptable salt thereof, for use in the treatment of cardiac arrhythmia, atrial fibrillation, primary hyperaldosteronism, hypertension and/or sick sinus syndrome, suitably atrial fibrillation.

In yet another embodiment of the present invention, there is provided (R)-8-Chloro-1-(2,6-dichlorophenyl)-5-(2,3-dihydroxypropoxy)-2-(hydroxymethyl)-1,6-naphthyridin-4 (1H)-one, or a pharmaceutically acceptable salt thereof, for use in the treatment of cardiac arrhythmia, atrial fibrillation, primary hyperaldosteronism, hypertension and/or sick sinus syndrome, suitably atrial fibrillation.

In yet another embodiment of the present invention, there is provided 8-Chloro-1-(2,6-dichlorophenyl)-5-(2,3-dihydroxypropoxy)-2-(hydroxymethyl)-1,6-naphthyridin-4 (1H)-one, or a pharmaceutically acceptable salt thereof, for use in the treatment of cardiac arrhythmia, atrial fibrillation, primary hyperaldosteronism, hypertension and/or sick sinus syndrome, suitably atrial fibrillation.

In yet another embodiment of the present invention, there is provided (R)-8-Chloro-1-(2,6-dichlorophenyl)-5-(3,4-dihydroxybutyl)-2-(hydroxymethyl)-1,6-naphthyridin-4(1H)-one, or a pharmaceutically acceptable salt thereof, for use in the treatment of cardiac arrhythmia, atrial fibrillation, primary hyperaldosteronism, hypertension and/or sick sinus syndrome, suitably atrial fibrillation.

In yet another embodiment of the present invention, there is provided (S)-8-Chloro-1-(2,6-dichlorophenyl)-5-(3,4-dihydroxybutyl)-2-(hydroxymethyl)-1,6-naphthyridin-4(1H)-one, or a pharmaceutically acceptable salt thereof, for use in the treatment of cardiac arrhythmia, atrial fibrillation, primary hyperaldosteronism, hypertension and/or sick sinus syndrome, suitably atrial fibrillation.

In yet another embodiment of the present invention, there is provided 8-Chloro-1-(2,6-dichlorophenyl)-5-(3,4-dihydroxybutyl)-2-(hydroxymethyl)-1,6-naphthyridin-4(1H)-one, or a pharmaceutically acceptable salt thereof, for use in the treatment of cardiac arrhythmia, atrial fibrillation, primary hyperaldosteronism, hypertension and/or sick sinus syndrome, suitably atrial fibrillation.

In yet another embodiment, the invention pertains to a compound according to any one of previous embodiments 1-13F, or a pharmaceutically acceptable salt thereof, for use in the treatment cardiac arrhythmia, atrial fibrillation, primary hyperaldosteronism, hypertension and/or sick sinus syndrome.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys, minipigs or isolated organs, tissues and preparations thereof. The compounds of the present invention can be applied in vitro in the form of solutions, e.g., aqueous solutions, and in vivo either enterally, parenterally, intravenously, e.g., as a suspension, emulsion or in aqueous solution. The dosage in vitro may range between about $10^{-2}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro method.
1. Buffers:
   a. External buffer: 10 mM NaCl, 50 mM Na Gluconate, 80 mM K Gluconate, 1.8 mM $CaCl_2$, 1 mM $MgCl_2$, 10 mM HEPES, 10 mM Glucose, pH 7.4; osmolality 300-310 Osm/L.
   b. Internal buffer: 30 mM KCl, 100 mM K Gluconate, 1 mM $MgCl_2$, 10 mM HEPES, 1 mM EGTA, 10 mM NaCl, pH 7.2; osmolality 284-292 Osm/L.
2. Compounds:
   a. Prepare seven-fold compound dilution series (10 mM to 20 uM) in 100% DMSO, in 384-well polypropylene plates.
   b. Propafenone (Sigma Aldrich, catalog number P4670) is used as a positive control and DMSO for neutral control
   c. Resuspend 1 ul of compounds in DMSO into 65.7 ul external buffer in 384-well polypropylene plate and load into Plate 1 section of Molecular Devices Quattro
3. Quattro setup:
   a. Load 384-well Population Patch Plate (Molecular Devices #9000-0902) into Quattro
   b. Fill Quattro F-soak trough with 20% DMSO and 50% EtOH
   c. Fill Quattro buffer trough with external buffer
   d. Attach internal buffer flask to Quattro internal buffer tubing
   e. Attach PBS (Phosphate Buffered Saline, minus $Ca^{++}$ and $Mg^{++}$, pH7.4) bottle to F-head & E-head wash on Quattro
4. Antibiotic:
   a. Resuspend 5.6 mg amphotericin B (Sigma Aldrich, catalog number A2411) in 175 ul DMSO
   b. Add the resulting solution to 50 ml internal buffer, mix and attach to antibiotic tubing port on Quattro
5. Cells:
   a. Use GIRK 1/4 HEK293 stable cells (obtained from ChanTest, 14656 Neo Parkway, Cleveland, Ohio 44128) grown to ~80% confluency in the following cell culture medium: DMEM containing 10% (v/v) Fetal Bovine Serum, Penicillin/Streptomycin (at "1×" concentration from a 100× stock), 0.5 mg/ml G418 and 0.1 mg/ml Zeocin.
   b. Wash cells with PBS (minus $Ca^{++}$ and $Mg^{++}$), Detach cells using Detachin (Genlantis, 11011 Torreyana, San Diego, Calif. 92121), and resuspend in external buffer (5 ml final volume at 2.0-2.1×$10^6$ cells/ml)
   c. Load into cell trough of Quattro
6. Assay Protocol:
Quattro is controlled using IonWorks v2 software to perform the following steps:
   a. Add 3.5 ul cells plus 3.5 ul external buffer to wells of Quattro Patch Plate
   b. Circulate amphotericin B and internal buffer onto cells c. Apply the following voltage protocol: Pulse 1: 15 mV for 300 milliseconds (ms), followed by Pulse 2: −120 mV for 400 ms, then Pulse 3: −15 mV for 400 ms, and finally Pulse 4: −120 mV to 40 mV over 500 ms (this is a voltage ramp).
d. Measure magnitude of inward potassium current at time point between 1200-1220 ms from start of Pulse 1 (i.e. during the voltage ramp phase).
e. Add 3.5 ul of diluted compounds (or DMSO) to wells and repeat steps c-d (final compound concentrations are 50 uM to 0.1 uM, for potent compounds 0.5 uM to 0.01 uM and each concentration is tested in quadruplicate—i.e. in 4 separate wells).
f. The difference between current magnitude pre vs. post-compound gives a measure of GIRK1/4 inhibition.

7. Data analysis:

$IC_{50}$ values are calculated by plotting the percentage of current inhibition (normalized to the DMSO-only control) as a function of compound concentration using standard data analysis software.

Using the test assay No. 1 (as described in this application) compounds of the invention exhibit inhibitory efficacy in accordance to Table 1, provided infra.

TABLE 1

Inhibitory Activity of Compounds

| Ex. | GIRK1/4 $IC_{50}$ (μM) |
|---|---|
| 1 | 0.1044 |
| 2 | 0.159 |
| 3 | 0.131 |
| 4 | 0.141 |
| 5 | 0.235 |
| 6 | 0.099 |
| 7 | 0.431 |
| 8 | 0.351 |
| 9 | 0.257 |
| 10 | 0.120 |
| 11 | 0.073 |
| 12 | 0.036 |
| 13 | 0.071 |
| 14 | 0.052 |
| 15 | 0.025 |
| 16 | 0.176 |
| 17 | 0.060 |
| 18 | 1.855 |
| 19 | 0.098 |
| 20 | 0.173 |
| 21 | 0.154 |
| 22 | 0.148 |
| 23 | 0.344 |
| 24 | 0.253 |
| 25 | 0.146 |
| 26 | 0.031 |
| 27 | 0.150 |
| 28 | 0.039 |
| 29 | 0.505 |
| 30 | 0.025 |
| 31 | 0.1 |
| 32 | 0.033 |
| 33 | 0.1 |
| 34 | 0.240 |
| 35 | 0.035 |
| 36 | 0.009 |
| 37 | 0.006 |
| 38 | 0.008 |
| 39 | 0.015 |
| 40 | 0.013 |
| 41 | 0.028 |
| 42 | 0.015 |
| 43 | 0.026 |
| 44 | 0.056 |
| 45 | 0.149 |
| 46 | 0.128 |
| 47 | 0.059 |
| 48 | 0.009 |
| 49 | 0.042 |
| 50 | 0.011 |
| 51 | 0.041 |
| 52 | 0.073 |
| 53 | 0.028 |
| 54 | 0.029 |
| 55 | 0.054 |
| 56 | 0.197 |
| 57 | 0.032 |
| 58 | 0.017 |
| 59 | 0.014 |
| 60 | 0.261 |
| 61 | 0.068 |
| 62 | 0.013 |
| 63 | 0.016 |
| 64 | 0.97 |
| 65 | 0.39 |
| 66 | 0.034 |
| 67 | 0.168 |
| 68 | 0.234 |
| 69 | 0.115 |
| 70 | 3.052 |
| 71 | 0.176 |
| 72 | 0.28 |
| 73 | 0.329 |
| 74 | 0.069 |
| 75 | 0.214 |
| 76 | 0.355 |
| 77 | 0.366 |
| 78 | 0.352 |
| 79 | 0.299 |
| 80 | 0.365 |
| 81 | 0.023 |
| 82 | 0.147 |
| 83 | 0.278 |
| 84 | 0.116 |
| 85 | 0.019 |
| 86 | 0.037 |
| 87 | 2.265 |
| 88 | 1.227 |
| 89 | 0.024 |
| 90 | 0.327 |
| 91 | 0.04 |
| 92 | 0.047 |
| 93 | 0.046 |

Combination of the Invention

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of any one of formulae (I) to (III) and at least one other therapeutic agent as a combined preparation for simultaneous, separate or sequential use in therapy. In one embodiment, the therapy is the treatment of a disease or condition responsive to the inhibition of GIRK1/4 channel. Products provided as a combined preparation include a composition comprising the compound of any one of formulae (I) to (III) and the other therapeutic agent(s) together in the same pharmaceutical composition, or the compound of any one of formulae (I) to (III) and the other therapeutic agent(s) in separate form, e.g. in the form of a kit.

In one embodiment, the invention provides a pharmaceutical composition comprising a compound of any one of formulae (I) to (III) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of any one of formulae (I) to (III) In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any one of formulae (I) to (III) for treating a disease or condition responsive to the inhibition of GIRK1/4 channel, wherein the medicament is prepared for administration with another therapeutic agent. The invention also provides the use of another therapeutic agent for treating a disease or condition responsive to the inhibition of GIRK1/4 channel, wherein the medicament is administered with a compound of any one of formulae (I) to (III).

The invention also provides a compound of any one of formulae (I) to (III) for use in a method of treating a disease or condition responsive to the inhibition of GIRK1/4 channel, wherein the compound of formula (I), (II) or (III) is prepared for administration with another therapeutic agent. The invention also provides another therapeutic agent for use in a method of treating a disease or condition responsive to the inhibition of GIRK1/4 channel, wherein the other therapeutic agent is prepared for administration with a compound of any one of formulae (I) to (III). The invention also provides a compound of any one of formulae (I) to (III) for use in a method of treating a disease or condition responsive to the inhibition of GIRK1/4 channel, wherein the compound of formula (I) is administered with another therapeutic agent. The invention also provides another therapeutic agent for use in a method of treating a disease or condition responsive to the inhibition of GIRK1/4 channel, wherein the other therapeutic agent is administered with a compound of any one of formulae (I) to (III).

The invention also provides the use of a compound of any one of formulae (I) to (III) for treating a disease or condition responsive to the inhibition of GIRK1/4 channel, wherein the patient has previously (e.g. within 24 hours) been treated with another therapeutic agent. The invention also provides the use of another therapeutic agent for treating a disease or condition responsive to the inhibition of GIRK1/4 channel, wherein the patient has previously (e.g. within 24 hours) been treated with a compound of formula (I), (II) or (III).

In one embodiment, the other therapeutic agent is selected from:

any other antiarrhythmic agent, such as Class I agents (e.g. quinidine, lidocaine, and propafenone), Class II agents (e.g. propranolol), Class III agents (e.g. sotalol, dofetilide, amiodarone, dronedarone, budiodarone, azimilide and ibutilide), Class IV agents (e.g. diltiazem and verapamil), "Class V agents" (e.g. adenosine), cardiac glycosides (e.g. digitalis and ouabain) and other drugs affecting atrial refractoriness (e.g. $I_{Na,Late}$ blockers such as described in WO2013112932); haemostasis modulators, including antithrombotics such as activators of fibrinolysis; thrombin inhibitors; factor VIIa inhibitors; anticoagulants, such as vitamin K antagonists (e.g. warfarin), heparin and low molecular weight analogues thereof (e.g. dalteparin), factor Xa inhibitors (e.g. rivaroxaban and apixaban), and direct thrombin inhibitors (e.g. argatroban); antiplatelet agents, such as cyclooxygenase inhibitors (e.g. aspirin and NSAIDs), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole); anti-dyslipidemia agents, such as HMG-CoA reductase inhibitors (statins) and other cholesterol-lowering agents; PPARa agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants; and omega-3 fatty acids; antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin II receptor antagonists (e.g. losartan); aldosterone receptor antagonists (e.g. eplerenone); centrally acting adrenergic drugs, such as central alpha agonists (e.g. clonidine); and diuretic agents (e.g. furosemide); anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CBI) receptor antagonists (e.g. rimonabant); insulin and insulin analogues; insulin secretagogues, including sulphonylureas (e.g. glipizide) and prandial glucose regulators (sometimes called "short-acting secretagogues"), such as meglitinides (e.g. repaglinide and nateglinide); agents that improve incretin action, for example dipeptidyl peptidase IV (DPP-4) inhibitors (e.g. vildagliptin, sitagliptin, LAF237, MK-431), and glucagon-like peptide-I (GLP-1) agonists (e.g. exenatide); insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity; agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators; agents designed to reduce/slow the absorption of glucose from the intestine, such as alpha-glucosidase inhibitors (e.g. miglitol and acarbose); agents which antagonise the actions of or reduce secretion of glucagon, such as amylin analogues (e.g. pramlintide); agents that prevent the reabsorption of glucose by the kidney, such as sodium-dependent glucose transporter 2 (SGLT-2) inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The term "diuretic" includes thiazide derivatives (e.g., chlorothiazide, hydrochlorothiazide, methylclothiazide, and chlorothalidon).

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal. The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia*, 28, 1985, 704-707 and in U.S. Pat. No. 5,705,483. The term "GLP-1 agonists" includes variants and analogs of GLP-1(7-36)$NH_2$ which are disclosed in particular in U.S. Pat. Nos. 5,120,712, 5,118,666, 5,512,549, WO 91/11457 and by C. Orskov et al in *J. Biol. Chem.* 264 (1989) 12826. Further examples include GLP-1(7-37), in which compound the carboxyterminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-GLP-1(7-37), acetyl $LYS^9$-GLP-1(7-37), $LYS^{18}$-GLP-1(7-37) and, in particular, GLP-1(7-37)OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al. in Diabetologia 1999, 42, 45-50.

An aldosterone synthase inhibitor or a pharmaceutically acceptable salt thereof is understood to be an active ingredient that has the property to inhibit the production of aldosterone. Aldosterone synthase (CYP1162) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities. The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

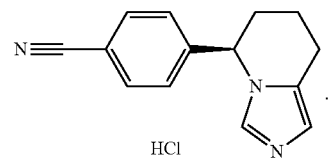 [SMILES: N#Cc1ccc([C@H]2CCCc3cncn32)cc1 ; Cl]

or, if appropriable, a pharmaceutically acceptable salt thereof.

A preferred steroidal aldosterone antagonist is eplerenone (cf. EP 122232 A) of the formula

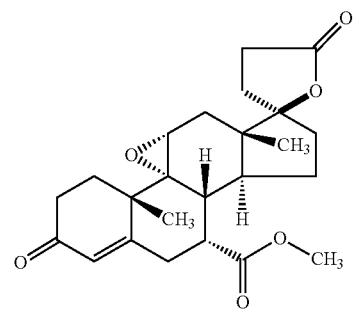

or Spironolactone; or, in each case, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett;* 6:1951-1954 (1996), respectively. Furthermore, the CETP inhibitors also include those disclosed in WO2000/017165, WO2005/095409 and WO2005/097806.

In another embodiment, the other therapeutic agent is selected from:

any other antiarrhythmic agent, such as Class I agents (e.g. quinidine, lidocaine, and propafenone), Class II agents (e.g. propranolol), Class III agents (e.g. sotalol, dofetilide, amiodarone, dronedarone, budiodarone, azimilide and ibutilide), Class IV agents (e.g. diltiazem and verapamil), "Class V agents" (e.g. adenosine), cardiac glycosides (e.g. digitalis and ouabain) and other drugs affecting atrial refractoriness (e.g. $I_{Na,Late}$ blockers such as described in WO2013112932).

EXEMPLIFICATION OF THE INVENTION

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The compounds in the examples below have been found to have $IC_{50}$ values in the range of about 0.01 nM to about 50,000 nM for GIRK1/4, more preferably 1 nM to 10,000 nM.

LIST OF ABBREVIATIONS

ACN acetonitrile
aq. aqueous
BOC tert-butyloxycarbonyl
br broad
bs broad singlet
° C. degrees celsius
conc. concentrated
δ NMR chemical shift in ppm downfield from tetramethylsilane
d doublet
DCE 1,2-dichloroethane
DCM dichloromethane
DEA diethylamine
DIPEA N,N-diisopropylethylamine
DMA dimethylacetamide
DMAP 4-(dimethylamino)pyridine
DME dimethoxyethane
DMEM Dulbecco's Modified Eagle Medium
DMF N,N-dimethylformamide
DMSO dimethylsulfoxide
DPPF 1,1'-bis(diphenylphosphino)ferrocene
Et ethyl
EtOAc ethyl acetate
g gram
h(r) hour
HEPES (4-(2-hydroxyethyl)-1-piperazineethanesulfonic acid
HATU O-(7-azabenzotriazol-1-yl)-N,N,N',N'-tetramethyluronium hexafluorophosphate
HRMS high-resolution mass spectrometry
i-Pr isopropyl
L liter
LDA lithium diisopropylamide
LC/MS liquid chromatography-mass spectrometry
M molarity
m multiplet
Me methyl
mg milligram
MHz megahertz
min minute
mL milliliter
µL microliter
mmol millimole
N normal
NBS N-bromosuccinimide
NCS N-chlorosuccinimide
n-Bu normal butyl n-BuLi n-butyllithium
NMM N-methylmorpholine
NMR nuclear magnetic resonance
NMP N-methyl-2-pyrrolidone
NMO N-methylmorpholine-N-oxide
o/n overnight
Ph phenyl
pH $-\log_{10}$ H$^+$ concentration
ppm parts per million
q quartet
Rt retention time
RP-HPLC reverse-phase high performance liquid chromatography
s singlet
SFC supercritical fluid chromatography
sat. saturated
t triplet
t-Bu tert-butyl
TBAF tert-butylammonium fluoride
Tf trifluoromethanesulfonyl
TFA trifluoroacetic acid
TFAA trifluoroacetic anhydride
TBDMS tert-butyldimethylsilyl
TEA triethylamine
temp. temperature
THF tetrahydrofuran
TLC thin layer chromatography Liquid Chromatography (LC) Methods LC method 1: The retention times in minutes (Rt) were obtained on an Agilent 1100 system with an XBridge C18 Column, 3.5 μm, 3.0×30 mm column. A gradient of H$_2$O (+0.05% ammonium hydroxide)/CH$_3$CN (+0.05% ammonium hydroxide) 98/2 to 2/98 was applied over 1.7 min., then held for 0.3 min. (2.0 mL/min. as solvent flow) at an oven temperature of 40° C.

LC method 2: The retention times in minutes (Rt) were obtained on an Agilent 1100 system with an Sunfire C18 Column, 3.5 μm, 3.0×30 mm column. A gradient of H$_2$O (+0.05% trifluoroacetic acid)/CH$_3$CN (+0.05% trifluoroacetic acid) 95/5 to 5/95 was applied over 1.7 min., then held for 0.3 min. (2.0 mL/min. as solvent flow) at an oven temperature of 40° C.

LC method 3: The retention times in minutes (Rt) were obtained on an Agilent 1100 system with an XBridge C18 Column, 3.5 μm, 3.0×30 mm column. A gradient of H$_2$O (+0.05% ammonium hydroxide)/CH$_3$CN (+0.05% ammonium hydroxide) 98/2 to 2/98 was applied over 1.7 min., then held for 0.3 min. (2.0 mL/min. as solvent flow) at an oven temperature of 40° C.

LC method 4: The retention times in minutes (Rt) were obtained on an Waters AcQuity UPLC system with an AcQuity UPLC BEH C18 1.7 μm 2.1×30 mm column. A gradient of H$_2$O (+0.05% ammonium hydroxide)/CH$_3$CN (+0.05% ammonium hydroxide) 98/2 to 2/98 was applied over 1.7 min., then held for 0.3 min. (1.0 mL/min. as solvent flow) at an oven temperature of 50° C.

SYNTHESIS OF INTERMEDIATES 1 TO 13

5,8-Dichloro-1-(2,6-dichlorophenyl)-2-methyl-1,6-naphthyridin-4(1H)-one (Intermediate 1)

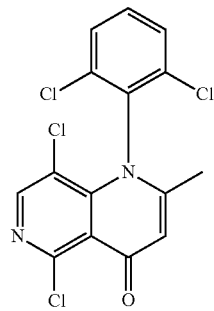 [SMILES: Cc1cc(=O)c2c(Cl)ncc(Cl)c2n1-c1c(Cl)cccc1Cl]

Step 1: 2,4,5-Trichloronicotinaldehyde

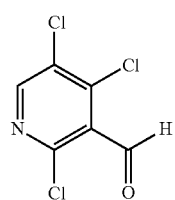

To a solution of 2,4,5-trichloropyridine (5 g, 27.4 mmol) in THF (150 ml) was added LDA (2 M in heptane, 20.56 ml, 41.1 mmol) at −78° C. The mixture was stirred at −78° C. for 1 hour. Then methyl formate (8.23 g, 137 mmol) in THF (20 mL) was added quickly into the reaction mixture followed by stirring at −78° C. for 1 hour. The reaction mixture was quenched with aqueous saturated NH$_4$Cl solution and extracted with EtOAc three times. The combined organic layers were dried over anhydrous Na$_2$SO$_4$ and volatiles were removed under reduced pressure. The residue was purified with silica-gel chromatography (10-100% EtOAc in heptane) to afford the title compound as solid (4.2 g, 73% yield). ESI-MS m/z: 211.8 [M+H]$^+$ (Rt=0.86 min, LC-method 1) $^1$H NMR (400 MHz, DCM-d$_2$) δ ppm=10.43 (s, 1H), 8.61 (s, 1H).

Step 2: 1-(2,4,5-Trichloropyridin-3-yl)but-2-yn-1-ol

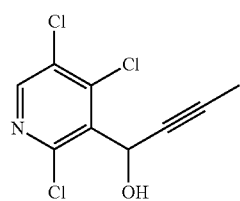

To a solution of 2,4,5-trichloronicotinaldehyde (2.11 g, 10.03 mmol) in THF (30 ml) was added prop-1-yn-1-ylmagnesium bromide (0.5 M in THF, 26.1 ml, 13.03 mmol) at 0° C. The reaction mixture was stirred at 0° C. for 1 hour. To the mixture was added aqueous saturated NH$_4$Cl solution followed by extraction with EtOAc. The combined organic layers were washed with water and brine, dried over anhydrous Na₂SO₄ and concentrated under reduced pressure. The crude was purified with silica-gel chromatography (10-100% EtOAc in heptane) to give the title compound (1.95 g, 78% yield). ESI-MS m/z: 250.0 [M+H]⁺ (Rt=0.94 min, LC-method 1) ¹H NMR (400 MHz, DCM-d₂) δ ppm=8.42 (s, 1H), 6.13 (s, 1H), 3.11 (bs, 1H), 1.90 (s, 3H).

Step 3:
1-(2,4,5-Trichloropyridin-3-yl)but-2-yn-1-one

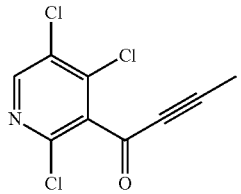

1-(2,4,5-trichloropyridin-3-yl)but-2-yn-1-ol (3.4 g, 13.57 mmol) in DCM (60 ml) was cooled down to 0° C. Then Dess-Martin reagent (6.91 g, 16.29 mmol) was added. The resulting solution was stirred at room temperature for 1 hour. Then it was quenched with aqueous saturated NaHCO₃ solution carefully, followed by dilution with DCM. The organic layer was washed with brine, dried over anhydrous MgSO₄, filtered, and concentrated under reduced pressure. The crude was purified with silica-gel chromatography (10-100% EtOAc in heptane) to give the title compound (2.6 g, 77% yield). ESI-MS m/z: 248.0 [M+H]⁺ (Rt=1.15 min, LC-method 1) ¹H NMR (400 MHz, DCM-d₂) δ ppm=8.51 (s, 1H), 2.16 (s, 3H).

Step 4: (E)-3-((2,6-Dichlorophenyl)amino)-1-(2,4,5-trichloropyridin-3-yl)but-2-en-1-one

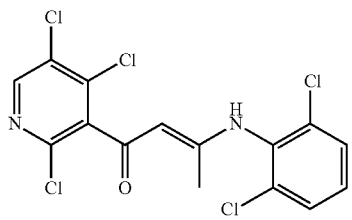 [SMILES: C/C(=C\C(=O)c1c(Cl)ncc(Cl)c1Cl)Nc1c(Cl)cccc1Cl]

To a solution of 1-(2,4,5-trichloropyridin-3-yl)but-2-yn-1-one (2.36 g, 9.50 mmol) and 2,6-dichloroaniline (1.69 g, 10.45 mmol) in 50 ml of DCM was added AlCl₃ (1.52 g, 11.40 mmol) at 0° C. The reaction mixture was stirred at room temperature overnight. 2N NaOH solution was added to the reaction mixture and it was extracted with DCM three times. The combined organic layers were dried over anhydrous Na₂SO₄ and concentrated under reduced pressure. The crude was purified with silica-gel chromatography (10-100% EtOAc in heptane) to give the title compound (2.99 g, 77%). ESI-MS m/z: 410.9 [M+H]⁺ (Rt=1.39 min, LC-method 1)

Step 5: 5,8-Dichloro-1-(2,6-dichlorophenyl)-2-methyl-1,6-naphthyridin-4(1H)-one

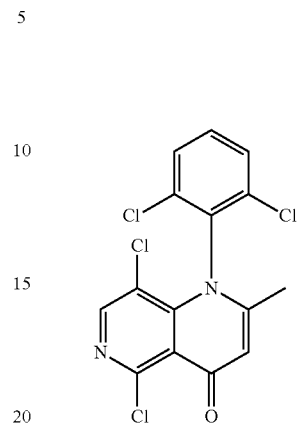

To a solution of 3-((2,6-dichlorophenyl)amino)-1-(2,4,5-trichloropyridin-3-yl)but-2-en-1-one (2.99 g, 7.28 mmol) in 45 ml of DMF was added K₂CO₃ (3.02 g, 21.85 mmol) at room temperature. The resulting solution was stirred overnight. The reaction was diluted with water and extracted with EtOAc three times. Combined organic layers were washed with brine and dried over anhydrous Na₂SO₄ and concentrated under reduced pressure. The crude product was purified with silica-gel chromatography (10-100% EtOAc in heptane) to give the title compound (1.8 g, 66% yield). ESI-MS m/z: 375.0 [M+H]⁺ (Rt=1.06 min, LC-method 1) ¹H NMR (400 MHz, DMSO-d₆) δ ppm=8.51 (s, 1H), 7.83-7.72 (m, 3H), 6.63 (d, J=0.7 Hz, 1H), 1.94 (s, 3H).

5,8-Dichloro-1-(2,6-dichloro-4-fluorophenyl)-2-methyl-1,6-naphthyridin-4(1H)-one (Intermediate 2)

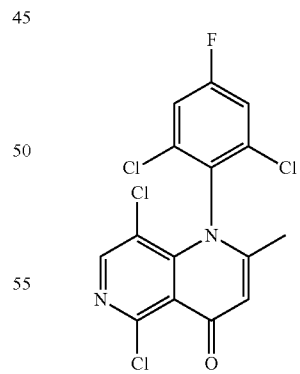

Intermediate 2 was prepared in an analogous way to intermediate 1 but using 2,6-dichloro-4-fluoroaniline in step 4 of the synthetic procedure to afford a white powder as the title compound.

2: ¹H NMR (400 MHz, DMSO-d6) δ ppm=8.32-8.76 (m, 1H), 7.92 (d, J=8.31 Hz, 2H), 6.63 (d, J=0.73 Hz, 1H), 1.96 (s, 3H).

3,5-Dichloro-4-(5,8-dichloro-2-methyl-4-oxo-1,6-naphthyridin-1(4H)-yl)benzonitrile (Intermediate 3)

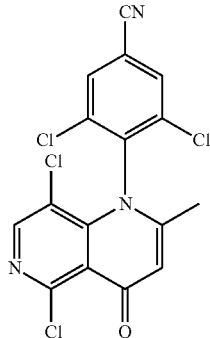 [SMILES: Cc1cc(=O)c2c(Cl)ncc(Cl)c2n1-c1c(Cl)cc(C#N)cc1Cl]

Intermediate 3 was prepared in an analogous way to intermediate 1 but using 2,6-dichloro-4-cyano aniline and BF$_3$*OEt$_2$ in step 4 of the synthetic procedure to afford a yellow powder. 3: $^1$H NMR (400 MHz, chloroform-d3) δ ppm=8.33 (s, 1H), 7.80 (s, 2H), 6.49 (d, J=0.7 Hz, 1H), 1.95 (d, J=0.6 Hz, 3H).

1-(4-Bromo-2,6-dichlorophenyl)-5,8-dichloro-2-methyl-1,6-naphthyridin-4(1H)-one (Intermediate 4)

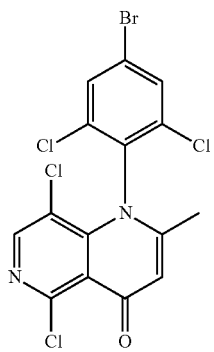 [SMILES: Cc1cc(=O)c2c(Cl)ncc(Cl)c2n1-c1c(Cl)cc(Br)cc1Cl]

Intermediate 4 was prepared in an analogous way to intermediate 1 but using 4-bromo-2,6-dichloroaniline in step 4 of the synthetic procedure to afford a white powder as the title compound. 4: $^1$H NMR (400 MHz, DMSO-d6) δ ppm=8.53 (s, 1H), 8.16 (s, 2H), 6.62 (d, J=0.7 Hz, 1H), 1.96 (s, 3H)

3-Chloro-2-(5,8-dichloro-2-methyl-4-oxo-1,6-naphthyridin-1(4H)-yl)benzonitrile (Intermediate 5)

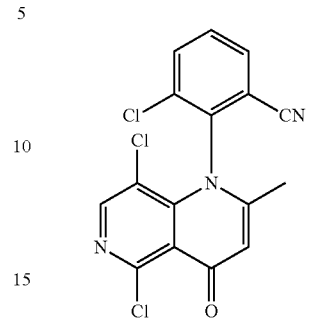

Intermediate 5 was prepared in an analogous way to intermediate 1 but using 2-cyano-6-chloro aniline and scandium triflate in step 4 of the synthetic procedure as described below.

Step 4: 3-Chloro-2-((4-oxo-4-(2,4,5-trichloropyridin-3-yl)but-2-en-2-yl)amino)benzonitrile

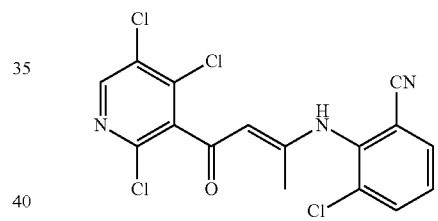

To a mixture solution of 1-(2,4,5-trichloropyridin-3-yl)but-2-yn-1-one (600 mg, 2.415 mmol) and 2-amino-3-chlorobenzonitrile (0.368 g, 2.415 mmol) in DCM (15 ml) was carefully added scandium trifluoromethanesulfonate (1.12 g, 2.415 mmol) at rt. After stirring at rt overnight, the mixture was quenched with 1N NaOH aqueous solution, the product was extracted with DCM. The organic layer was washed with brine, dried over anhydrous sodium sulfate, filtered, and concentrated on vacuum. The crude residue was purified by column chromatography on silica gel eluting with 0-50% EtOAc in heptane to provide the products: 3-chloro-2-((4-oxo-4-(2,4,5-trichloropyridin-3-yl)but-2-en-2-yl)amino) benzonitrile (0.166 g, 17.2%), ESI-MS m/z: 400.2 [M+H]$^+$ and 3-chloro-2-(5,8-dichloro-2-methyl-4-oxo-1,6-naphthyridin-1(4H)-yl)benzonitrile (0.143 g, 16.2% yield) ESI-MS m/z: 364.2 [M+H]$^+$ $^1$H NMR (400 MHz, MeCN-d3) δ ppm=8.36 (s, 1H) 7.87-8.06 (m, 2H) 7.62-7.85 (m, 1H) 6.47 (d, J=0.63 Hz, 1H) 1.98 (s, 3H)

Step 5: 3-Chloro-2-(5,8-dichloro-2-methyl-4-oxo-1,6-naphthyridin-1(4H)-yl)benzonitrile

Preparation of 2-amino-3-chloro-5-fluorobenzonitrile

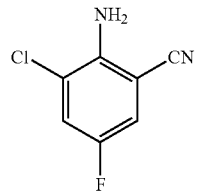

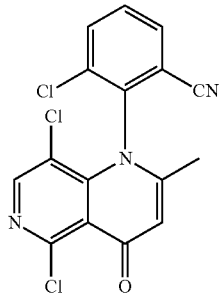 [SMILES: Cc1cc(=O)c2c(Cl)ncc(Cl)c2n1-c1c(Cl)cccc1C#N]

NCS (4.75 g, 35.6 mmol) was added to the solution of 2-amino-5-fluorobenzonitrile (4.4 g, 32.3 mmol) in MeCN (92 ml). The resulting mixture was stirred at 80° C. overnight. After the volume was reduced to half under vacuum, the residue was poured into water, the precipitate was collected by filtration, washed with water, dried to provide the desired aniline (4 g, 73%). $^1$H NMR (400 MHz, DMSO-$d_6$) δ ppm=7.64 (dd, J=8.40, 2.97 Hz, 1H) 7.50 (dd, J=8.40, 2.97 Hz, 1H) 6.08 (br s, 2H)

2-(((tert-Butyldimethylsilyl)oxy)methyl)-5,8-dichloro-1-(2,6-dichlorophenyl)-1,6-naphthyridin-4(1H)-one (Intermediate 7)

The mixture of 3-chloro-2-((4-oxo-4-(2,4,5-trichloropyridin-3-yl)but-2-en-2-yl)amino)benzonitrile (0.49 g, 1.22 mmol) and potassium carbonate (0.422 g, 3.05 mmol) in DMF (10 mL) was stirred at 95° C. for 1 h. After cooling to rt, the mixture was diluted with water, and the product was extracted with EtOAc. The organic layer was washed with water, brine, dried over anhydrous sulfate, filtered and concentrated under reduced pressure. The residue was purified via flash chromatography on silica gel using 0-100% EtOAc/in heptane as eluent to give the title compound (0.31 g, 70%). 5: ESI-MS m/z: 364.2 [M+H]$^+$. $^1$H NMR (400 MHz, MeCN-$d_3$) δ ppm=8.36 (s, 1H) 7.87-8.06 (m, 2H) 7.62-7.85 (m, 1H) 6.47 (d, J=0.63 Hz, 1H) 1.98 (s, 3H)

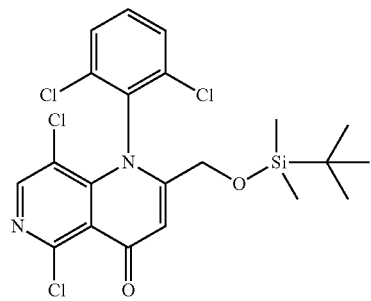 [SMILES: CC(C)(C)[Si](C)(C)OCc1cc(=O)c2c(Cl)ncc(Cl)c2n1-c1c(Cl)cccc1Cl]

Step 1: 2,4,5-Trichloronicotinaldehyde

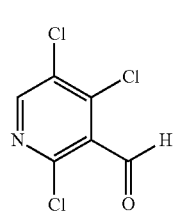 [SMILES: O=Cc1c(Cl)ncc(Cl)c1Cl]

3-Chloro-2-(5,8-dichloro-2-methyl-4-oxo-1,6-naphthyridin-1(4H)-yl)-5-fluorobenzonitrile (Intermediate 6)

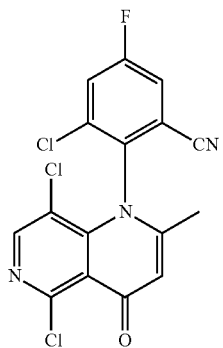

Intermediate 6 was prepared in an analogous way to intermediate 5 but using 2-amino-3-chloro-5-fluorobenzonitrile, which was synthesized by the following procedure to afford a white powder.

6: ESI-MS m/z: 382.2 [M+H]$^+$

To a solution of 2,4,5-trichloropyridine (5 g, 27.4 mmol) in 150 ml of THF was added LDA (2 M in heptane, 20.56 ml, 41.1 mmol) at −78° C. The mixture was stirred at −78° C. for 1 hour. Then methyl formate (8.23 g, 137 mmol) in THF (20 mL) was added quickly into the reaction mixture followed by stirring at −78° C. for 1 hour. The reaction mixture was quenched with aqueous saturated NH$_4$Cl solution and extracted with EtOAc three times. The combined organic layers were dried over anhydrous Na$_2$SO$_4$ and, volatiles were removed under reduced pressure. The residue was purified with silica-gel chromatography (10-100%

EtOAc in heptane) to afford the desired compound as a solid (4.2 g, 73%). ESI-MS m/z: 211.8 [M+H]+ (Rt=0.86 min, LC-method 1), ¹H NMR (400 MHz, DCM-d₂) δ ppm=10.43 (s, 1H), 8.61 (s, 1H).

Step 2: 4-((tert-Butyldimethylsilyl)oxy)-1-(2,4,5-trichloropyridin-3-yl)but-2-yn-1-ol

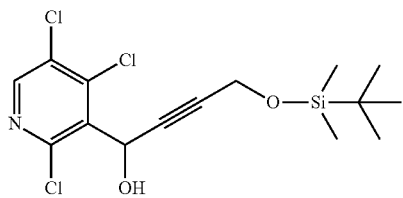 [SMILES: CC(C)(C)[Si](C)(C)OCC#CC(O)c1c(Cl)ncc(Cl)c1Cl]

Tert-butyldimethyl (prop-2-yn-1-yloxy)silane (11.14 g, 65.4 mmol) in 20 ml of THF was cooled to −78° C. and n-BuLi (1.6 M, 24.52 ml, 39.2 mmol) was added in dropwise. The mixture was stirred at −78° C. for 45 minutes and then treated with a solution 2,4,5-trichloronicotinaldehyde (6.88 g, 32.7 mmol) in 40 ml of THF. The mixture was allowed to stir at −78° C. for 2 hrs. The progress of the reaction was monitored by LC-MS which showed complete consumption of the aldehyde starting material. The mixture was quenched with saturated NH₄Cl and extracted with EtOAc. The organic layer was washed with water and brine, dried under Na₂SO₄, filtered and concentrated under reduced pressure to get crude compound as yellow liquid which was used further without any purification. ESI-MS m/z: 382 [M+H]+ (Rt=1.47 min, LC-method 1) ¹H NMR (400 MHz, DCM-d₂) δ ppm=8.32 (s, 1H), 6.27-5.96 (m, 1H), 4.40-4.15 (m, 2H), 0.93 (s, 9H), 0.02 (s, 6H).

Step 3: 4-((tert-Butyldimethylsilyl)oxy)-1-(2,4,5-trichloropyridin-3-yl)but-2-yn-1-one

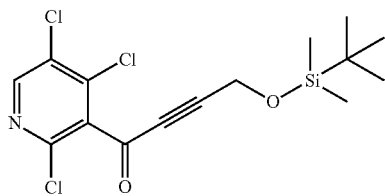 [SMILES: CC(C)(C)[Si](C)(C)OCC#CC(=O)c1c(Cl)ncc(Cl)c1Cl]

To a stirred solution of 4-((tert-butyldimethylsilyl)oxy)-1-(2,4,5-trichloropyridin-3-yl)but-2-yn-1-ol (12.45 g, 32.7 mmol) in DCM (131 ml), Dess-Martin periodinane (16.64 g, 39.2 mmol) was added at 0° C. The resulting solution was stirred at room temperature for 30 minutes. The progress of the reaction was monitored by LC-MS which showed complete consumption of the starting material. The reaction mixture was quenched with saturated aqueous NaHCO₃ solution carefully, followed by dilution with DCM. Precipitate was filtered off. The organic layer was washed with saturated NaHCO₃ and washed with brine, dried over anhydrous Na₂SO₄. The organic layer was concentrated under reduced pressure. The crude compound was purified by silica gel column chromatography (10-100% EtOAc in heptane) to afford desired compound (7.5 g, 61%). ESI-MS m/z: 380 [M+H]+ (Rt=1.66 min, LC-method 1)

¹H NMR (400 MHz, DCM-d₂) δ ppm=8.38 (s, 1H), 4.44 (s, 2H), 0.82 (s, 9H), 0.01 (s, 6H).

Step 4: (E)-4-((tert-Butyldimethylsilyl)oxy)-3-((2,6-dichlorophenyl)amino)-1-(2,4,5-trichloropyridin-3-yl)but-2-en-1-one

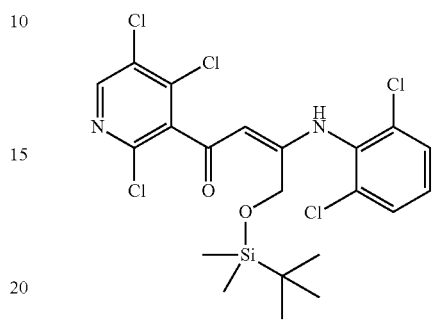

To a stirred solution of 4-((tert-butyldimethylsilyl)oxy)-1-(2,4,5-trichloropyridin-3-yl)but-2-yn-1-one (7.41 g, 19.56 mmol) in DCM (185 ml), were added 2,6-dichloroaniline (3.49 g, 21.52 mmol) followed by AlCl₃ (2.87 g, 21.52 mmol) in one portion at 0° C. and reaction mixture was stirred for 2 hours at room temperature. The progress of the reaction was monitored by LC-MS which showed complete consumption of the starting material. To the reaction mixture 2N NaOH (20 mL) was added and the mixture was stirred for 30 minutes at room temperature. Reaction mixture was extracted with DCM and the combined organic layers were washed with brine dried over anhydrous Na₂SO₄. The organic layer was concentrated under reduced pressure. The crude compound was purified by silica gel column chromatography (10-100% EtOAc in heptane) to afford the title compound (6.4 g, 61% yield). ESI-MS m/z: 540.9 [M+H]+ (Rt=2.01 min, LC-method 1)

Step 5: 2-(((tert-Butyldimethylsilyl)oxy)methyl)-5,8-dichloro-1-(2,6-dichlorophenyl)-1,6-naphthyridin-4(1H)-one

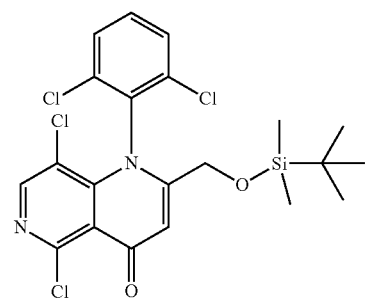 [SMILES: CC(C)(C)[Si](C)(C)OCc1cc(=O)c2c(Cl)ncc(Cl)c2n1-c1c(Cl)cccc1Cl]

To a stirred solution of (E)-4-((tert-butyldimethylsilyl)oxy)-3-((2,6-dichlorophenyl)amino)-1-(2,4,5-trichloropyridin-3-yl)but-2-en-1-one (6.37 g, 11.78 mmol) in DMF (47 ml) was added potassium carbonate (8.14 g, 58.9 mmol) and the reaction mixture was stirred at 80° C. for 3 hrs. The reaction mixture was poured in ice cold water and extracted with EtOAc. The organic layers were washed with brine, dried over anhydrous Na₂SO₄ and evaporated under reduced pressure. The crude compound was purified by silica gel column chromatography (10-100% EtOAc in heptane) to afford the desired compound (4.6 g, 77% yield).

7: ESI-MS m/z: 504.9 [M+H]+ (Rt=1.62, LC-method 1) $^1$H NMR (400 MHz, DCM-$d_2$) δ ppm=8.26 (s, 1H), 7.48 (d, J=2.0 Hz, 3H), 6.73 (s, 1H), 4.05-3.90 (m, 2H), 0.85 (s, 9H). 0.01 (s, 6H).

5,8-Dichloro-1-(2,6-dichlorophenyl)-2-(methoxymethyl)-1,6-naphthyridin-4(1H)-one (Intermediate 8)

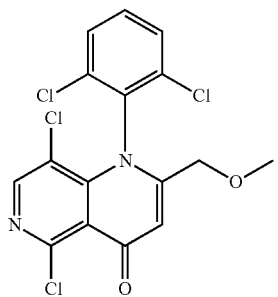 [SMILES: COCc1cc(=O)c2c(Cl)ncc(Cl)c2n1-c1c(Cl)cccc1Cl]

Intermediate 8 was prepared in an analogous way to intermediate 7 but using 3-methoxyprop-1-yne in step 2 of the synthetic procedure to afford a white powder. 8: ESI-MS m/z: 405.2 [M+H]+ (Rt=1.08 min, LC-method 1); $^1$H NMR (400 MHz, DCM-$d_2$) δ ppm=8.33 (s, 1H), 7.63-7.49 (m, 3H), 6.71 (s, 1H), 3.88 (s, 2H), 3.32 (s, 3H).

3-Chloro-2-(5,8-dichloro-2-cyclopropyl-4-oxo-1,6-naphthyridin-1(4H)-yl)benzonitrile (Intermediate 9)

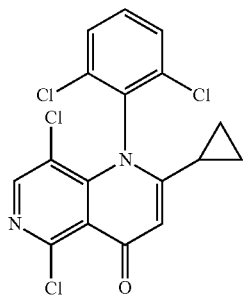 [SMILES: O=c1cc(C2CC2)n(-c2c(Cl)cccc2Cl)c2c(Cl)cnc(Cl)c12]

Intermediate 9 was prepared in an analogous way to intermediate 7 but using ethynylcyclopropane in step 2 and 2-amino-3-chlorobenzonitrile in step 4 of the synthetic procedure to afford a white powder. 9: ESI-MS m/z: 392.0 [M+H]+ (Rt=1.01 min, LC-method 1) 8-Bromo-5-chloro-1-(2,6-dichlorophenyl)-2-methyl-1,6-naphthyridin-4(1H)-one (Intermediate 10)

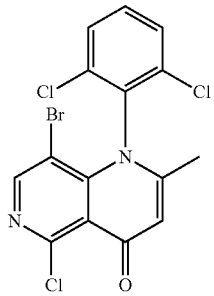 [SMILES: Cc1cc(=O)c2c(Cl)ncc(Br)c2n1-c1c(Cl)cccc1Cl]

Intermediate 10 was prepared in an analogous way to intermediate 1 using 5-bromo-2,4-dichloropyridine as a starting material to afford a white powder.

10: $^1$H NMR (400 MHz, chloroform-d3) δ ppm=8.50 (s, 1H), 7.50 (s, 3H), 6.51 (d, J=0.7 Hz, 1H), 1.96 (dd, J=2.5, 0.7 Hz, 3H).

5,7-Dichloro-1-(2,6-dichlorophenyl)-2-methyl-1,6-naphthyridin-4(1H)-one (Intermediate 11)

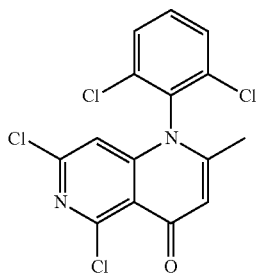 [SMILES: Cc1cc(=O)c2c(Cl)nc(Cl)cc2n1-c1c(Cl)cccc1Cl]

Step 1: 2,4,6-Trichloronicotinaldehyde

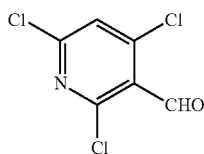 [SMILES: O=Cc1c(Cl)cc(Cl)nc1Cl]

2,4,6-Trichloropyridine (5 g, 27.4 mmol) in anhydrous THF (100 ml) was cooled to −78° C. A solution of n-butyllithium (22.27 ml, 28.8 mmol) (1.6M in hexane) was added slowly at −78° C. The solution was stirred at −78° C. for 30 mins, then treated with a solution of ethyl formate (10.15 g, 137 mmol) maintaining an internal temperature below −74° C. The resulting solution was stirred at −78° C. until all starting material was consumed (monitored by TLC, 9:1 heptane/EtOAC), then it was quenched at −78° C. with a solution of saturated ammonium chloride and 50 ml 0.5N aq. HCl under vigorous stirring. It was then allowed to warm to r.t. The quenched mixture was extracted with EtOAc, the organic phase was washed with brine, dried over MgSO$_4$, and concentrated. The crude residue (light yellow solid) was purified by flash chromatography on silica gel with 0-20% EtOAc/heptane to provide 5.1 g (88% yield) of the desired 2,4,6-trichloronicotinaldehyde as a white solid. $^1$H NMR (400 MHz, chloroform-d3) δ ppm=10.42 (s, 1H), 7.45 (s, 1H).

The remaining steps were prepared in an analogous way as described for intermediate 1. The intermediate 11 is produced as a white powder.

11: ¹H NMR (400 MHz, chloroform-d3) δ ppm=7.75-7.53 (m, 3H), 6.42 (d, J=0.8 Hz, 1H), 6.29 (s, 1H), 1.97 (d, J=0.8 Hz, 3H).

3,5-Dichloro-4-(5-fluoro-2-methyl-4-oxo-1,7-naphthyridin-1(4H)-yl)benzonitrile (Intermediate 12)

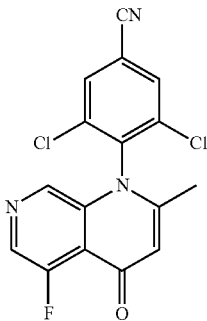 [SMILES: Cc1cc(=O)c2c(F)cncc2n1-c1c(Cl)cc(C#N)cc1Cl]

Step 1:
3,5-Difluoro-N-methoxy-N-methylisonicotinamide

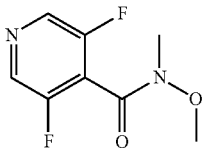

3,5-difluoroisonicotinic acid (18.78 g, 118 mmol), N,O-dimethylhydroxylamine hydrochloride (12.09 g, 124 mmol), HATU (47.1 g, 124 mmol) and DIPEA (61.9 ml, 354 mmol) were suspended in DCM (236 ml). The mixture was allowed to stir at room temperature for 24 hours. The mixture was concentrated under reduced pressure. The residue was extracted with EtOAc washing with saturated aqueous NH₄Cl solution (2×), water, saturated NaHCO₃ and brine. The organic layer was dried over sodium sulfate and concentrated. The crude was purified by chromatography on silica gel using 0-75% EtOAc in heptanes as eluent to give the title compound (18.9 g, 79% yield). ESI-MS m/z: 203.1 [M+H]⁺ (Rt=0.81 min, LC-method 2) ¹H NMR (400 MHz, DMSO-d₆) δ ppm=9.16 (s, 2H), 4.03 (s, 3H), 3.82 (s, 3H).

Step 2:
3,5-Difluoro-N-methoxy-N-methylisonicotinamide

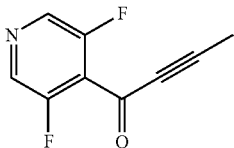

3,5-difluoro-N-methoxy-N-methylisonicotinamide (10.25 g, 50.7 mmol) was dissolved in THF (127 ml) and the reaction mixture was cooled down to 0° C. Prop-1-yn-1-ylmagnesium bromide (0.5 M in THF, 304 ml, 152 mmol) was then added slowly (~30 minutes) using an addition funnel and the moisture was allowed to warm up to room temperature overnight. The next day it was quenched by adding it to a stirring 0.5N HCl solution at 0° C. and extracted with DCM (3×). The combined organic layers were dried over sodium sulfate and concentrated under reduced pressure. The residue was purified with silica-gel chromatography (0-50% EtOAc in heptane) to afford the title compound as solid (7.22 g, 79% yield). ESI-MS m/z: 182.0 [M+H]⁺ (Rt=1.11 min, LC-method 2); ¹H NMR (400 MHz, DMSO-d₆) δ ppm=8.74 (s, 2H), 2.22 (s, 3H).

Step 3: 3-(2,6-Dichloro-4-cyanophenyl)-6-(3,5-difluoropyridin-4-yl)-2,2-difluoro-4-methyl-2,3-dihydro-1,3,2-oxazaborinin-1-ium-2-uide

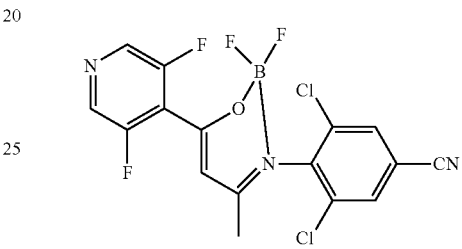

1-(3,5-difluoropyridin-4-yl)but-2-yn-1-one (7.86 g, 43.4 mmol) and 4-amino-3,5-dichlorobenzonitrile (9.74 g, 52.1 mmol) were dissolved in DCM (174 ml) and the mixture was treated with BF₃*OEt₂ (16.50 ml, 130 mmol). The reaction mixture was stirred at 50° C. overnight. The next day it was quenched via a slow addition to a saturated. NaHCO₃ solution. Some MeOH was used for complete dissolution and transfer of the reaction mixture. The mixture was extracted with DCM (3×). The combined organic layers were dried over sodium sulfate and concentrated under reduced pressure. The residue was purified by silica gel column chromatography (10-100% EtOAc in heptane) to give the title compound (10.05 g, 55.7% yield).

ESI-MS m/z: 368.0 [M+H]⁺ (Rt=1.43 min, LC-method 2)

Step 4: 3,5-Dichloro-4-(5-fluoro-2-methyl-4-oxo-1,7-naphthyridin-1(4H)-yl)benzonitrile

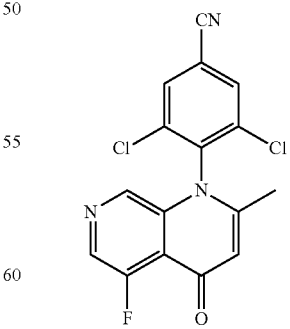

A mixture of 3-(2,6-dichloro-4-cyanophenyl)-6-(3,5-difluoropyridin-4-yl)-2,2-difluoro-4-methyl-2,3-dihydro-1,3,2-oxazaborinin-1-ium-2-uide (17.16 g, 41.3 mmol) and K₂CO₃ (28.5 g, 206 mmol) in THF (110 ml) and MeOH (55 mL) was heated at 50° C. for 1.5 hours. To the reaction mixture was added EtAOc. The solution was washed with water and brine, dried over Na$_2$SO$_4$, filtered, and concentrated in vacuo. The residue was purified by flash column chromatography on silica gel (0-100% EtOAc in heptane) to provide the title compound (8.26 g, 57%).

12: HRMS calc. 348.0095 [M+H]$^+$; found 348.0102; $^1$H NMR (400 MHz, DMSO-d6) δ ppm=9.06 (s, 2H), 8.99 (d, J=2.3 Hz, 1H), 8.61 (s, 1H), 6.92 (s, 1H).

3,5-Dichloro-4-(5-bromo-2-methyl-4-oxo-1,7-naphthyridin-1(4H)-yl)benzonitrile (Intermediate 13)

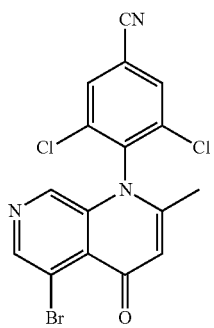 [SMILES: Cc1cc(=O)c2c(Br)cncc2n1-c1c(Cl)cc(C#N)cc1Cl]

Step 1: 3-Bromo-5-fluoroisonicotinaldehyde

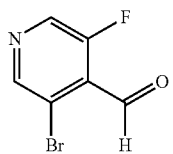

To a LDA solution (1M in hexanes/THF, 12.55 mL, 12.55 mmol) was added a solution of 3-bromo-5-fluoropyridine (1.84 g, 10.46 mmol) in THF (20 ml) at −78° C. dropwise. The mixture was stirred at −78° C. for 1 h. Then DMF (1.62 mL, 1.53 g, 20.91 mmol) was added to the reaction mixture. After stirring at −78° C. for 30 min, the reaction mixture was quenched with aq. sat. NaHCO$_3$ solution followed by extracting with EtOAC three times and DCM twice. All the organic layers were combined and dried over anhydrous Na$_2$SO$_4$. The solid was filtered out. Volatiles were removed under reduced pressure and the residue was purified with silica-gel chromatography (DCM) to afford the title compound (0.478 g, 22%). $^1$H NMR (400 MHz, chloroform-d3) δ ppm=10.36 (s, 1H), 8.75 (s, 1H), 8.63-8.57 (m, 1H).

Step 2: 1-(3-Bromo-5-fluoropyridin-4-yl)but-2-yn-1-ol

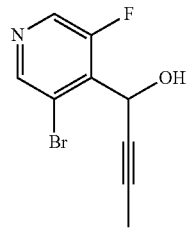

To a solution of 3-bromo-5-fluoroisonicotinaldehyde (0.656 g, 3.22 mmol) in THF (5 mL) was added prop-1-yn-1-ylmagnesium bromide (0.5 M in THF, 8.36 mL, 4.18 mmol) solution at 0° C. After stirring at 0° C. for 2 h, excess sat. aq. NaHCO$_3$ solution was added to quench the reaction mixture followed by extracting with EtOAc twice and DCM twice. All organic layers were combined and dried over anhydrous Na$_2$SO$_4$. The solid was filtered out. Volatiles were removed under reduced pressure to afford the title compound (0.78 g, 99%). It was used directly in the next step without further purification. ESI-MS m/z: 245.9 [M+H]$^+$ (Rt=0.92 min., LC-method 3)

Step 3: 1-(3-Bromo-5-fluoropyridin-4-yl)but-2-yn-1-one

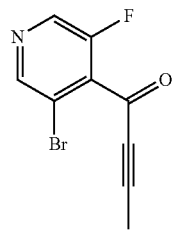

To a solution of 1-(3-bromo-5-fluoropyridin-4-yl)but-2-yn-1-ol (0.78 g, 3.2 mmol) in DCM (30 mL) was added Dess-Martin reagent (1.63 g, 3.84 mmol) at 0° C. The reaction mixture was stirred at room temperature for 30 min. followed by quenching with excess sat. aq. NaHCO$_3$ solution. The mixture was extracted with DCM three times. All DCM layers were combined, concentrated and then purified with silica-gel chromatography (10% EtOAc/heptane) to afford the title compound. ESI-MS m/z: 244.2 [M+H]$^+$ (Rt=1.17 min, LC-method 3).

Step 4: 4-((4-(3-Bromo-5-fluoropyridin-4-yl)-4-oxobut-2-en-2-yl(amino)-3,5-dichlorobenzonitrile

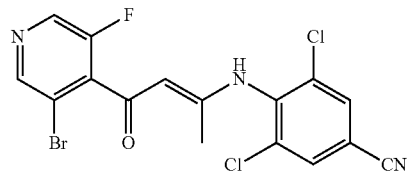 [SMILES: C/C(=C\C(=O)c1c(F)cncc1Br)Nc1c(Cl)cc(C#N)cc1Cl]

and 6-(3-bromo-5-fluoropyridin-4-yl)-3-(2,6-dichloro-4-cyanophenyl)-2,2-difluoro-4-methyl-2H-1,3,2-oxazaborinin-3-ium-2-uide

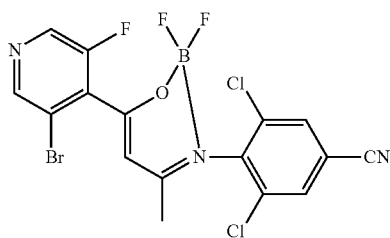

A mixture of 1-(3-bromo-5-fluoropyridin-4-yl)but-2-yn-1-one (2.50 g, 10.33 mmol), 4-amino-3,5-dichlorobenzonitrile (2.22 g, 11.88 mmol) and $BF_3*OEt_2$ (8.80 g, 62.0 mmol) in DCE (120 mL) was stirred at 80° C. overnight. The reaction mixture was quenched with 1 N aq. NaOH solution followed by extracting with DCM three times. All DCM layers were combined and dried over anhydrous $Na_2SO_4$. The solid was filtered out. Volatiles were removed under reduced pressure and the residue was purified with silica-gel chromatography (10-50% EtOAc/heptane) to afford a mixture of 4-((4-(3-bromo-5-fluoropyridin-4-yl)-4-oxobut-2-en-2-yl)amino)-3,5-dichlorobenzonitrile (ESI-MS m/z: 429.7 [M+H]+ (Rt=1.22 min, LC-method 3)) and its $BF_2$ complex 6-(3-bromo-5-fluoropyridin-4-yl)-3-(2,6-dichloro-4-cyanophenyl)-2,2-difluoro-4-methyl-2H-1,3,2-oxazaborinin-3-ium-2-uide (ES−-MS m/z: 475.9 [M−H]− (Rt=1.37 min, LC-method 3)) (3.84 g in total). The mixture was used directly in the next step.

Step 5: 4-(5-Bromo-2-methyl-4-oxo-1,7-naphthyridin-1(4H)-yl)-3,5-dichlorobenzonitrile

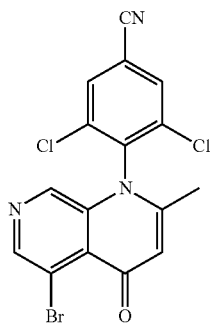

To a solution of the mixture (2.50 g) obtained from step 4 in DMF (15 mL) was added $K_2CO_3$ (3.22 g, 23.31 mmol). The reaction mixture was stirred at 100° C. for 25 min. The solid was filtered out. Volatiles were removed under reduced pressure and the residue was purified with silica-gel chromatography (20-50% EtOAc/heptane) to afford brown solid as the title compound (1.2 g).

13: ESI-MS m/z: 410.0 [M+H]+

$^1$H NMR (400 MHz, DMSO-d6) δ ppm=8.69 (s, 1H), 8.58 (s, 2H), 8.24 (s, 1H), 6.50 (s, 1H), 2.00 (s, 3H).

SYNTHESIS OF EXAMPLES

Synthesis of Examples 1 to 57

The following examples of formula Ia, Ib have been prepared from intermediates 1 to 13 by nucleophilic aromatic substitution with alcohols and amines. If necessary, deprotection of protective groups on additional alcohol functionality in the molecules was done as the ultimate step.

General Method:

In a reaction vial, intermediates 1 to 13 (typically 0.1-0.25 mmol, 1 eq.), alcohol (5-10 eq.) or amine (1.2 eq.), $K_2CO_3$ (5-10 eq.) and DMAP (0.1-0.5 eq.) were mixed in MeCN (1-3 mL). Other solvents which are used in case of poor solubility are THF or NMP or DMF. The resulting reaction mixture was heated for 1-16 h at 80° C. The reaction mixture was diluted with EtOAc and washed with water. The organic phase was dried over $Na_2SO_4$, filtered and concentrated in vacuo. The residue was purified by silica gel chromatography or in the case of very polar products by reverse phase HPLC (0.1% ammonia in MeCN/water) to afford the desired products Ia, Ib (40-80% yield) as a white or off white solid. In cases where the alcohol or amine has several reactive nucleophilic centers reagents were used where the additional functional group(s) was protected with a TBDMS, Boc group or as a ketal. In this case the protective group was removed by treatment with TFA in DCM at room temperature, TBAF in THF at 0° C. or AcOH/water (~2/1) at room temperature. After aqueous work-up as described above the crude product was purified by silica gel chromatography or in the case of very polar products by reverse phase HPLC (0.1% ammonia in MeCN/water) to afford the desired products Ia, Ib as a white or off white solid.

Example 1: (S)-8-Chloro-1-(2,6-dichlorophenyl)-5-(2,3-dihydroxpropoxy)-2-(hydroxymethyl)-1,6-naphthyridin-4(1H)-one

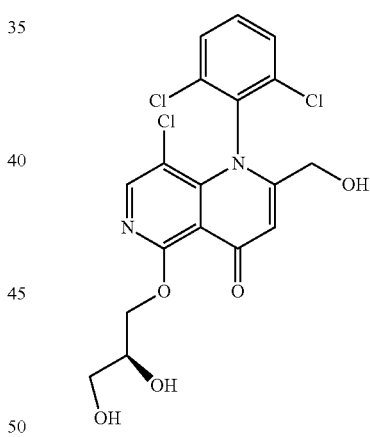

Step 1: (R)-2-(((tert-Butyldimethylsilyl)oxy)methyl)-8-chloro-1-(2,6-dichlorophenyl)-5-((2,2-dimethyl-1,3-dioxolan-4-yl)methoxy)-1,6-naphthyridin-4(1H)-one 2-(((tert-Butyldimethylsilyl)oxy)methyl)-5,8-dichloro-1-(2,6-dichlorophenyl)-1,6-naphthyridin-4(1H)-one (Intermediate 7, 1.3 g, 2.58 mmol) was dissolved in MeCN (15 mL). This solution was treated with potassium carbonate (1.069 g, 7.73 mmol), DMAP (0.157 g, 1.289 mmol), and (R)-(2,2-dimethyl-1,3-dioxolan-4-yl)methanol (1.022 g, 7.73 mmol). The resulting mixture was heated at 80° C. overnight. The next day the reaction mixture was filtered off and rinsed with ACN. The organic layer was concentrated in vacuo. The residue was purified by silica gel column chromatography (10-50% EtOAc in heptane) to provide the title compound (0.8 g, 52% yield). ESI-MS m/z: 601.0 [M+H]+ (Rt=3.53 min, LC-method 1); $^1$H NMR (400 MHz, DCM-d2) δ ppm=8.03 (s, 1H), 7.47 (s, 3H), 6.67 (s, 1H), 4.60-4.39 (m, 3H), 4.24-4.10 (m, 1H), 4.10-3.93 (m, 3H), 1.40 (s, 3H), 1.36 (s, 3H), 0.85 (s, 9H), 0.0 (s, 6H).

Step 2: (S)-8-Chloro-1-(2,6-dichlorophenyl)-5-(2,3-dihydroxypropoxy)-2-(hydroxymethyl)-1,6-naphthyridin-4(1H)-one Water (2 ml) and acetic acid (3 ml) were pre-mixed and added to the flask containing (R)-2-(((tert-butyldimethylsilyl)oxy)methyl)-8-chloro-1-(2,6-dichlorophenyl)-5-((2,2-dimethyl-1,3-dioxolan-4-yl)methoxy)-1,6-naphthyridin-4 (1H)-one (0.280 g, 0.467 mmol). To help to dissolve the starting material the flask was sonicated 5-10 minutes. The reaction mixture was stirred at room temperature overnight and followed by LC/MS. It was concentrated in vacuo at a bath temperature of 26° C. and vacuum of 20 mbar. The majority of the acetic acid was removed and the remaining aqueous solution was cooled in an ice bath and diluted with EtOAc. Slowly a 10% aqueous sodium carbonate solution was added until pH 7. The layers were separated and the organic phase was washed with brine, dried over sodium sulfate, filtered, and concentrated. The residue was purified by silica gel column chromatography (0-10% MeOH in DCM) to give the title compound with 97% ee (0.15 g, 72% yield) (around 3% regioisomer formation of example 9 was observed).

1: ESI-MS m/z: 446.9 [M+H]+ (Rt=0.74 min, LC-method 4)

$^1$H NMR (400 MHz, DCM-d2) δ ppm=8.13 (s, 1H), 7.58-7.43 (m, 3H), 6.94 (s, 1H), 4.70 (dd, J=11.2, 1.7 Hz, 1H), 4.39 (dd, J=11.2, 3.8 Hz, 1H), 4.07 (s, 2H), 4.04-3.97 (m, 1H), 3.91 (dd, J=11.7, 2.1 Hz, 1H), 3.78 (dd, J=11.6, 5.2 Hz, 1H).

Alternatively, example 1 can be prepared by the following procedures:

HPLC Method:

Column: Waters Acquity BEH C18 Length 100 mm, internal diameter 2.1 mm, particle size: 1.7 μm.

Mobile phase: A: 0.05% TFA in water, B: 0.05% TFA in methanol

Gradient:

| Time [min.] | Phase B [%] |
| --- | --- |
| 0.0 | 5.0 |
| 10.0 | 95.0 |
| 13.0 | 95.0 |
| 13.1 | 5.0 |
| 16.0 | 5.0 |

| Flow rate | 0.4 mL/min |
| --- | --- |
| Detection | UV 220 nm |

Column temperature: 30 Celsius degree.
Solvent for sample preparation: acetonitrile
Chiral Method:
Column: Daicel Chiralpak IE-3. Length 150 mm, internal diameter 4.6 mm, particle size: 3.0 μm.
Mobile phase: A: 0.1% TFA in heptane, B: Ethanol. (isocratic program: A/B=70/30; runtime: 25 min)

| Flow rate | 1.0 mL/min |
| --- | --- |
| Detection | UV 265 nm |

Column temperature: 40 Celsius degree

Step 1: 2-{[(tert-Butyldimethylsilyl)oxy]methyl}-8-chloro-1-(2,6-dichlorophenyl)-5-{[(4R)-2,2-dimethyl-1,3-dioxolan-4-yl]methoxy}-1,4-dihydro-1,6-naphthyridin-4-one To a solution of ((R)-2,2-dimethyl-[1,3]dioxolan-4-yl)-methanol (6.3 g, 47.59 mmol) in THF (140 mL) was added lithium diisopropylamide (2M in THF, 24 mL, 47.59 mmol) dropwise at −10° C. to −5° C. The reaction was allowed to stir at −5° to 0° C. for 1 h. Then a solution 2-{[(tert-butyldimethylsilyl) oxy]methyl}-5,8-dichloro-1-(2,6-dichlorophenyl)-1,4-dihydro-1,6-naphthyridin-4-one (Intermediate 7: 20 g, 39.658 mmol) in THF (60 mL) was added dropwise at −10° C. to −5° C. The reaction mixture was slowly warmed to room temperature in 30 min and stirred for 2 h. The progress of the reaction was monitored by HPLC. If starting material was <0.5%, workup was initiated, otherwise the reaction was stirred for another 4-16 h monitored by HPLC. Into the reaction mixture was added THF/H$_2$O=20 mL/2 mL with internal temperature of 20-25° C., then 20% of NH$_4$Cl solution (100 mL) was added with internal temperature of 20-25° C. The layers were separated and the aqueous layer was extracted with ethyl acetate (2×100 mL). The combined organic layers were washed with water (100 mL) followed by 20% of brine (100 mL).

Crystallization: The organic layer was concentrated under reduced pressure to get a residue of around 40 g, then n-heptane (2×400 ml) was used to run the azeotrope distillation until 50 g of residue was obtained. n-Heptane (400 mL) was added into the residue and the mixture was heated to internal temperature of 60° C. in 30 min, hold for 1-2 h and then the hot mixture was filtered. The filtrate was cooled down to 0° C. in 10 h and stirred for 6 h. The precipitate formed was separated via filtration. This wet cake was suspended in ethyl acetate (20 mL) and n-heptane (200 mL) and heated to 55° C. in 30 min. The resulting solution was stirred for 30 min at 55° C. The solution was slowly cooled to 0° C. in 6 h and hold for at least 3 h. The precipitate was filtered and dried to afford an off white solid as the title compound (13.8 g, 57% yield).

ESI-MS m/z: 601.0 [M+H]+; HPLC purity: 98.9%, enantiomeric excess: 99.1%; $^1$H NMR (400 MHz, DMSO-d6) δ ppm=8.26 (s, 1H), 7.82-7.68 (m, 3H), 6.53 (s, 1H), 4.53-4.38 (m, 3H), 4.17-4.08 (m, 1H), 4.06-3.98 (m, 3H), 1.37 (s, 3H), 1.33 (s, 3H), 0.85 (s, 9H), 0.02--0.05 (m, 6H); $^{13}$C NMR (101 MHz, DMSO-d6) δ ppm=−5.22, 18.37, 26.05, 26.20, 27.02, 60.72, 66.30, 67.09, 73.85, 109.20, 110.04, 111.18, 114.93, 129.48, 133.07, 133.90, 136.12, 145.07, 150.45, 151.56, 162.57, 175.16

Step 2: (R)-8-chloro-1-(2,6-dichlorophenyl)-5-((2,2-dimethyl-1,3-dioxolan-4-yl)methoxy)-2-(hydroxymethyl)-1,6-naphthyridin-4(1H)-one To a solution of 2-{[(tert-butyldimethylsilyl)oxy] methyl}-8-chloro-1-(2,6-dichlorophenyl)-5-{[(4R)-2,2-dimethyl-1,3-dioxolan-4-yl]methoxy}-1,4-dihydro-1,6-naphthyridin-4-one (15 g, 25 mmol) in THF (50 mL) was added a solution of tetrabutylammonium fluoride trihydrate (9.5 g, 30 mmol) in THF (25 mL) drop-wise with internal temperature of 20-25° C. The reaction mixture was allowed to stir for 2 h. The progress of the reaction was monitored by HPLC. HPLC shows 96.8% product with complete consumption of starting material. The reaction mixture was cooled down to internal temperature of 0-5° C., and then ice water (75 ml) was added dropwise with internal temperature of 0-5° C., followed with isopropyl acetate (75 ml).

The layers were separated and the aqueous layer was extracted with isopropyl acetate (75 mL).

The combined organic layer was washed with water (1×75 mL) followed by 20% of brine (1×75 mL)

Crystallization:

The organic layer was concentrated under vacuum to get 40 g of residue, and then isopropyl acetate (5×150 mL) was added to run azeotrope distillation until 50 g of residue was obtained. The mixture was cooled down to 20~25° C. and product seed (6 mg) was added. The mixture was hold for 2 h at internal temperature of 20~25° C., then the mixture was warmed to internal temperature of 35±3° C. in 30 min, hold for 30 min and n-heptane (150 mL) was added in 6 h. The mixture was cooled down to an internal temperature of 0±3° C. in 5 h and aged for at least 3 h. The desired product was obtained via filtration and the wet cake was washed with n-heptane (15 mL) and then dried over vacuum at 40° C. to get the title compound as a light yellow solid (10.5 g, 86.5% yield).

ESI-MS m/z: 486.9 [M+H]$^+$; HPLC purity: 98.3%, enantiomeric excess: 99.6%; $^1$H NMR (400 MHz, DMSO-d6) δ ppm=8.23 (s, 1H), 7.78-7.68 (m, 3H), 6.54 (s, 1H), 5.85 (t, J=6.0 Hz, 1H), 4.49-4.37 (m, 3H), 4.14-4.08 (m, 1H), 4.04-3.97 (m, 1H), 3.78 (d, J=5.26 Hz, 2H), 1.36 (s, 3H), 1.31 (s, 3H). $^{13}$C NMR (101 MHz, DMSO-d6) δ ppm=26.20, 27.00, 58.86, 66.33, 67.11, 73.86, 109.21, 110.00, 111.16, 114.06, 129.48, 133.15, 133.80, 135.98, 136.01, 145.00, 150.25, 153.49, 162.58, 175.10

Step 3: (S)-8-chloro-1-(2,6-dichlorophenyl)-5-(2,3-dihydroxypropoxy)-2-(hydroxymethyl)-1,6-naphthyridin-4(1H)-one To a 400 ml Flexy cube were charged acetonitrile (67.9 g) and (R)-8-chloro-1-(2,6-dichlorophenyl)-5-((2,2-dimethyl-1,3-dioxolan-4-yl)methoxy)-2-(hydroxymethyl)-1,6-naphthyridin-4(1H)-one (13.1 g, 1.0 eq). To another 100 ml flask were added acetonitrile (29.1 g), Water (1.96 g) and Bi(OTf)$_3$ (4.42 g, 0.25 eq). The corresponding Bi(OTf)$_3$ solution was added into the flexy cube at 20±3° C. over 15 min. The reaction mixture was cooled to 10±3° C. over 40 min and held at 10±3° C. for 45 min. After that, the reaction mixture was cooled to 0±3° C. over 30 min and held at 0±3° C. for 30 min, when the reaction was complete by UPLC analysis. To the reaction mixture was added 5% wt NaHCO$_3$ aq. solution (67 g) slowly to keep the temperature below 10° C. Ethyl acetate (120 g) was added and the mixture was warmed up to room temperature. The phases were separated and the aqueous solution was extracted with ethyl acetate (59 g) and isopropyl alcohol (5.1 g). The combined organic phase was washed with 20% wt brine (75 g). The organic solvent was exchanged to isopropyl alcohol and concentrated under 50-100 mbar at 50° C. to 32.6 grams of residue left. To the residue was added methyl-tert-butylether (20 g) at 50±3° C. over 30 min. The mixture was stirred for another 30 min till more solid precipitated out. Methyl-tert-butylether (80 g) was added over 1 h. The temperature was cooled to 23±3° C. over 2 h, methyl-tert-butylether (60 g) was added over 2 h and held for 2 h. The solid was filtered; the wet cake was washed with mixed solvent of isopropyl alcohol (3.9 g) and methyl-tert-butylether (37 g) twice. The crude material was then dissolved in acetonitrile (27.2 g) and water (103 g) at 25±3° C. to become a clear solution. Seeds (48 mg) were added and stirred for 30 min, followed by addition of water (137.5 g) over 2 h. The mixture was held at 25±3° C. for 1 h and then cooled to 0±3° C. over 7 h. It was filtered and the wet cake was washed with water. The wet cake was dried in vacuum at 60° C. for 16 h to provide (S)-8-chloro-1-(2,6-dichlorophenyl)-5-(2,3-dihydroxypropoxy)-2-(hydroxymethyl)-1,6-naphthyridin-4(1H)-one as light yellow solid (7.95 g, 66% yield).

ESI-MS m/z: 445.011 [M+H]$^+$; HPLC purity: 99.34%, enantiomeric excess: 99.3%; $^1$H NMR (400 MHz, DMSO-d6) δ ppm=8.28 (s, 1H), 7.91-7.70 (m, 3H), 6.62 (s, 1H), 5.91 (s, 1H), 5.24 (t, J=5.38 Hz, 1H), 4.85 (t, J=5.75 Hz, 2H), 3.85 (br d, J=5.38 Hz, 2H), 3.75 (t, J=5.56 Hz, 4H); $^{13}$C NMR (101 MHz, DMSO-d6) δ ppm=58.27, 63.36, 68.90, 69.03, 109.24, 110.52, 113.35, 128.93, 132.48, 133.29, 135.35, 144.26, 149.95, 153.26, 162.20, 174.94

Example 1A (Hydrate Form B)

Recrystallization:

To 200 mg of amorphous material of example 1, 1 ml acetonitrile/water (9:1, v/v) was added to get a clear solution at 50° C. with stirring. After 1 h of stirring at this temperature, the solution was cooled down slowly to 5° C. and a white precipitate occurred. The precipitate was separated by centrifugation and dried at 40° C. for 12 hrs. A white crystalline powder (modification hydrate form B) of the compound was obtained.

Alternatively, hydrate B can be produced by exposing (S)-8-chloro-1-(2,6-dichlorophenyl)-5-(2,3-dihydroxypropoxy)-2-(hydroxymethyl)-1,6-naphthyridin-4(1H)-one (any form from example 1) to 92% RH for more than 72 h at 25° C. or by slurrying (S)-8-chloro-1-(2,6-dichlorophenyl)-5-(2,3-dihydroxypropoxy)-2-(hydroxymethyl)-1,6-naphthyridin-4(1H)-one (any form from example 1) in pure water at 25° C. for at least 72 h.

a) X-Ray Powder Diffraction (XRPD) Method Description

An x-ray powder diffraction pattern was recorded on a Bruker™ D8 Advancediffractometer with CuKα anode (CuKα radiation (λ=1.5418 Å). A sample of ca 75-100 mg is place on zero-background Si-wafer sample holder and centered in the x-ray beam. The X-ray diffraction pattern thus determined is shown in FIG. 1 and represented in Table 2 below by the reflection lines of the most important lines.

TABLE 2

| Angle 2-Theta° | d value Angstrom | Intensity % % |
|---|---|---|
| 6.7 | 13.149 | 16.1 |
| 7.0 | 12.578 | 100 |
| 11.9 | 7.423 | 37.4 |
| 12.3 | 7.162 | 15.8 |
| 14.1 | 6.257 | 54.6 |
| 18.5 | 4.787 | 50.0 |
| 22.2 | 4.008 | 37.2 |
| 24.7 | 3.597 | 92.3 |
| 26.0 | 3.424 | 70.3 |
| 26.9 | 3.307 | 95.9 |
| 34.2 | 2.619 | 39.3 |
| 39.1 | 2.302 | 30.7 | b) Differential Scanning Calorimetry (DSC) and Thermogravimetric Analysis (TGA)

Differential scanning calorimetry (DSC) and thermogravimetric analysis (TGA) trace of Form B was obtained using TA Instruments Q2000 (DSC) and Q5000 (TGA) using the heating range indicated in the FIGS. 2 to 3.

DSC Method Description

Accurately weigh 0.5-1.5 mg of test substance each into a sample pan with pinhole and a closed (hermetic) sample pan. Empty sample pans are used as reference. The DSC thermogram is recorded as follow: the temperature of the apparatus is adjusted to about −40° C., and heated to 300° C. at a heating rate of 10° C./min, under a nitrogen flow of 50 mL/min. The instrument is calibrated for temperature and enthalpy with Indium, at least 99.9999% pure to 300° C. at a heating rate of 10° C./min, under a nitrogen flow of 50 mL/min. The accuracy of the measured sample temperature with this method is within about ±1° C., and the heat of fusion can be measured within a relative error of about ±5%.

With pinhole sample pan (FIG. 2.) I Glass temperature onset: $T_{onset}$=38.77° C., melting endotherm onset: $T_{onset}$=113.69° C.

With hermetic sample pan (FIG. 3); Melting endotherm onset: $T_{onset}$=82.30° C.

TGA Method Description

Accurately weigh 10-20 mg of test substance into the Al-sample pan. The TGA thermogram is recorded as follows: To avoid weight losses the sample pan has a hermetically sealed lid that is pierced automatically only moments before the sample is loaded into the furnace. The temperature equilibrated to 30° C. and heated to 200° C. at a heating rate of 10° C./min, under a flow of nitrogen at 25 mL/min.

The instrument is calibrated for temperature with nickel and aluminum, and calibrated for weight with a 5 and 10 mg standard. (FIG. 4)

The following examples in Table 1 were prepared using method A:

TABLE 1

Examples 2-58

| Ex. | Structure | Chemical name | Analytical data |
|---|---|---|---|
| 2 | 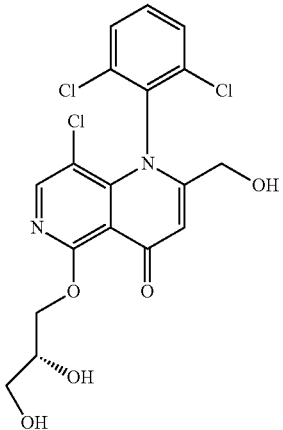 [SMILES: O=c1cc(CO)n(-c2c(Cl)cccc2Cl)c2c(Cl)cnc(OC[C@H](O)CO)c12] | (R)-8-chloro-1-(2,6-dichlorophenyl)-5-(2,3-dihydroxypropoxy)-2-(hydroxymethyl)-1,6-naphthyridin-4(1H)-one | ESI-MS m/z: 445 [M + H]$^+$ (Rt = 0.80 min, LC-method 1). $^1$H NMR (400 MHz, DMSO-d6) δ ppm = 8.24 (s, 1H), 7.85-7.57 (m, 3H), 6.56 (s, 1H), 5.85 (t, J = 5.9 Hz, 1H), 4.88 (d, J = 5.2 Hz, 1H), 4.76 (t, J = 6.0 Hz, 1H), 4.38 (dd, J = 10.7, 5.5 Hz, 1H), 4.30 (dd, J = 10.7, 5.8 Hz, 1H), 3.86 (p, J = 5.4 Hz, 1H), 3.79 (d, J = 5.2 Hz, 2H), 3.65-3.48 (m, 2H). |
| 3 | 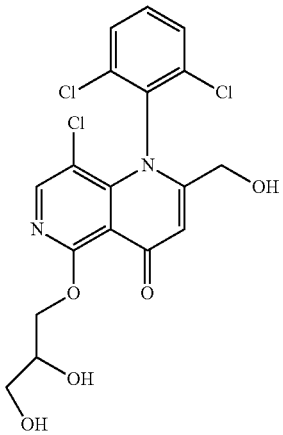 [SMILES: O=c1cc(CO)n(-c2c(Cl)cccc2Cl)c2c(Cl)cnc(OCC(O)CO)c12] | 8-chloro-1-(2,6-dichlorophenyl)-5-(2,3-dihydroxypropoxy)-2-(hydroxymethyl)-1,6-naphthyridin-4(1H)-one | ESI-MS m/z: 445 [M + H]$^+$ (Rt = 0.79 min, LC-method 1). $^1$H NMR (400 MHz, DCM-d2) δ ppm = 8.02 (d, J = 3.8 Hz, 1H), 7.42 (d, J = 2.6 Hz, 3H), 6.74 (d, J = 4.4 Hz, 1H), 4.61 (ddd, J = 11.2, 2.2, 1.2 Hz, 1H), 4.25 (dd, J = 11.2, 3.6 Hz, 1H), 3.97 (s, 2H), 3.91-3.80 (m, 2H), 3.73-3.66 (m, 1H). |

TABLE 1-continued

Examples 2-58

| Ex. | Structure | Chemical name | Analytical data |
|---|---|---|---|
| 4 | 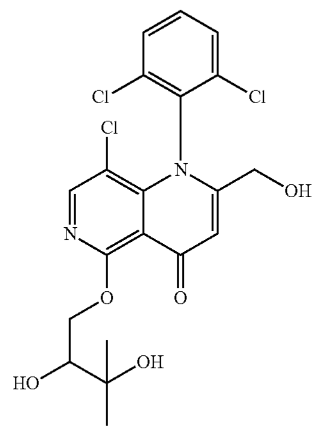 [SMILES: CC(C)(O)C(O)COc1ncc(Cl)c2c1c(=O)cc(CO)n2-c1c(Cl)cccc1Cl] | 8-chloro-1-(2,6-dichlorophenyl)-5-(2,3-dihydroxy-3-methylbutoxy)-2-(hydroxymethyl)-1,6-naphthyridin-4(1H)-one | HRMS calc. 474.7386 [M + H]$^+$; found 474.7356, $^1$H NMR (400 MHz, MeCN-d3) δ ppm = 8.18 (s, 1 H) 7.40-7.83 (m, 3 H) 6.42-6.90 (m, 1 H) 4.87 (s, 1 H) 4.66 (d, J = 3.03 Hz, 1H) 4.27-4.51 (m, 1 H) 3.90-4.07 (m, 2 H) 3.85 (m, 1 H) 3.67 (m, 2 H) 1.96 (s, 3 H) 1.28 (d, J = 19.96 Hz, 6H) |
| 5 | 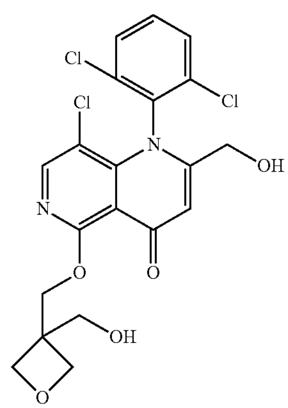 [SMILES: O=c1cc(CO)n(-c2c(Cl)cccc2Cl)c2c(Cl)cnc(OCC3(CO)COC3)c12] | 8-chloro-1-(2,6-dichlorophenyl)-2-(hydroxymethyl)-5-((3-(hydroxymethyl)oxetan-3-yl)methoxy)-1,6-naphthyridin-4(1H)-one | ESI-MS m/z: 471 [M + H]$^+$ (Rt = 0.89 min, LC-method 1) $^1$H NMR (400 MHz, DMSO-d6) δ ppm = 8.26 (s, 1H), 7.82-7.58 (m, 3H), 6.54 (s, 1H), 5.85 (t, J = 5.9 Hz, 1H), 5.03 (t, J = 5.8 Hz, 1H), 4.57 (s, 2H), 4.52-4.28 (m, 4H), 3.82 (dd, J = 26.8, 5.5 Hz, 4H). |
| 6 | 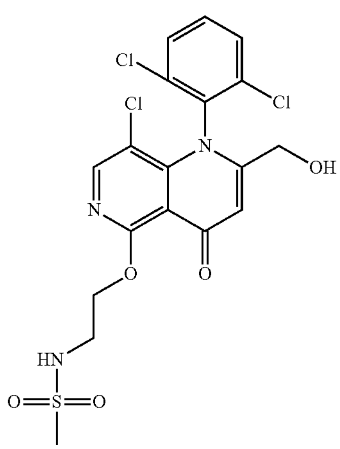 | N-(2-((8-chloro-1-(2,6-dichlorophenyl)-2-(hydroxymethyl)-4-oxo-1,4-dihydro-1,6-naphthyridin-5-yl)oxy)ethyl)methanesulfonamide | HRMS calc. 466.0507 [M + H]$^+$; found 466.0506, $^1$H NMR (400 MHz, DCM-d2) δ ppm = 9.78 (s, 1H), 7.97 (s, 3H), 7.11 (s, 1H), 6.37-6.17 (m, 1H), 4.74 (s, 1H), 3.58 (q, J = 5.8 Hz, 2H), 3.48 (q, J = 5.6 Hz, 2H), 3.02 (s, 3H), 2.10 (s, 3H). |

TABLE 1-continued

Examples 2-58

| Ex. | Structure | Chemical name | Analytical data |
|---|---|---|---|
| 7 | 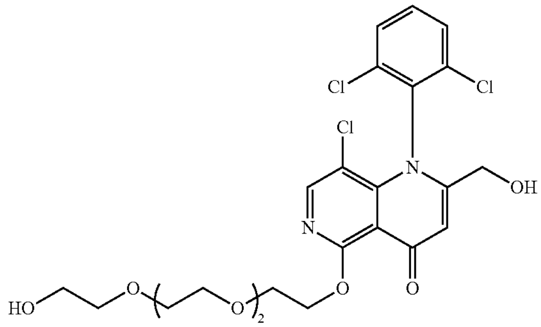 | 8-chloro-1-(2,6-dichlorophenyl)-5-(2-(2-(2-(2-hydroxyethoxy)ethoxy)ethoxy)ethoxy)-2-(hydroxymethyl)-1,6-naphthyridin-4(1H)-one | HRMS calc. 547.0806 [M + H]$^+$; found 547.0796, $^1$H NMR (400 MHz MeCN-d3) δ ppm = 8.03-8.22 (m, 1 H) 7.41-7.73 (m, 3 H) 6.60 (m, 1 H) 4.51-4.70 (m, 2 H) 3.93 (m, 2 H) 3.84-3.89 (m, 2 H) 3.72-3.78 (m, 2 H) 3.57-3.65 (m, 9 H) 3.48-3.53 (m, 2 H) 2.94 (br s, 1 H) |
| 8 | 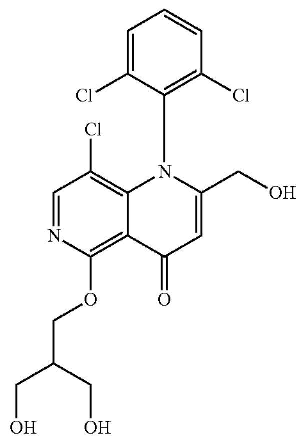 [SMILES: O=c1cc(CO)n(-c2c(Cl)cccc2Cl)c2c(Cl)cnc(OCC(CO)CO)c12] | 8-chloro-1-(2,6-dichlorophenyl)-5-(3-hydroxy-2-(hydroxymethyl)propoxy)-2-(hydroxymethyl)-1,6-naphthyridin-4(1H)-one | ESI-MS m/z: 445.1 [M + H]$^+$ (Rt = 0.84 min, LC-method 1), $^1$H NMR (400 MHz, MeCN-d3) δ ppm = 8.07 (s, 1H), 7.50 (d, J = 2.9 Hz, 3H), 6.56 (s, 1H), 4.41 (d, J = 5.8 Hz, 2H), 3.89-3.77 (m, 3H), 3.70-3.54 (m, 4H). |
| 9 | 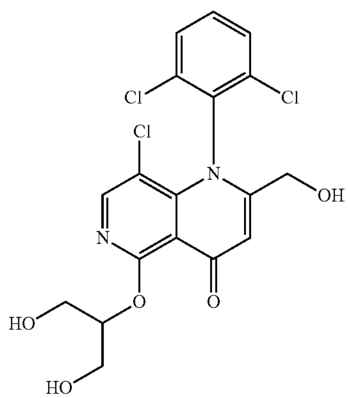 [SMILES: O=c1cc(CO)n(-c2c(Cl)cccc2Cl)c2c(Cl)cnc(OC(CO)CO)c12] | 8-chloro-1-(2,6-dichlorophenyl)-5-((1,3-dihydroxypropan-2-yl)oxy)-2-(hydroxymethyl)-1,6-naphthyridin-4(1H)-one | ESI-MS m/z: 445 [M + H]$^+$ (Rt = 0.78 min, LC-method 1), $^1$H NMR (400 MHz, DCM-d2) δ ppm = 8.01 (s, 1H), 7.42 (d, J = 2.6 Hz, 3H), 6.72 (s, 1H), 4.88 (dt, J = 7.6, 4.2 Hz, 1H), 3.97 (s, 2H), 3.68 (qd, J = 12.2, 5.4 Hz, 4H). |
| 10 | 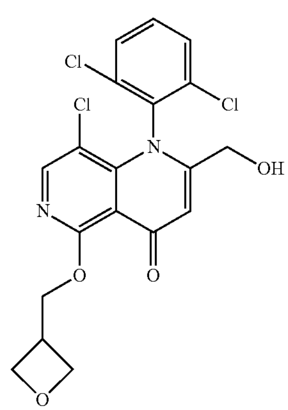 [SMILES: O=c1cc(CO)n(-c2c(Cl)cccc2Cl)c2c(Cl)cnc(OCC3COC3)c12] | 8-chloro-1-(2,6-dichlorophenyl)-2-(hydroxymethyl)-5-(oxetan-3-ylmethoxy)-1,6-naphthyridin-4(1H)-one | ESI-MS m/z: 443 [M + H]$^+$ (Rt = 0.93 min, LC-method 1), $^1$H NMR (400 MHz, MeCN-d3) δ ppm = 8.13 (s, 1H), 7.68-7.56 (m, 3H), 6.60 (t, J = 1.1 Hz, 1H), 4.76 (dd, J = 8.0, 6.0 Hz, 2H), 4.70-4.53 (m, 3H), 3.98-3.86 (m, 2H), 3.77 (q, J = 6.4, 5.5 Hz, 1H), 3.50 (dtd, J = 14.3, 6.4, 1.5 Hz, 1H). |

TABLE 1-continued

Examples 2-58

| Ex. | Structure | Chemical name | Analytical data |
|---|---|---|---|
| 11 | 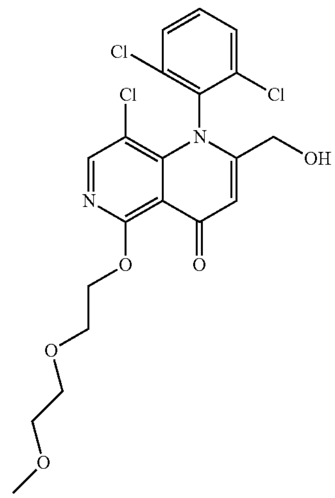 [SMILES: COCCOCCOc1ncc(Cl)c2c1c(=O)cc(CO)n2-c1c(Cl)cccc1Cl] | 8-chloro-1-(2,6-dichlorophenyl)-2-(hydroxymethyl)-5-(2-(2-methoxyethoxy)ethoxy)-1,6-naphthyridin-4(1H)-one | ESI-MS m/z: 475 [M + H]+ (Rt = 0.96 min, LC-method 1), $^1$H NMR (400 MHz, DCM-d2) δ ppm = 7.96 (s, 1H), 7.39 (d, J = 1.3 Hz, 3H), 6.61 (t, J = 1.0 Hz, 1H), 4.48 (dd, J = 5.5, 4.3 Hz, 2H), 3.92 (d, J = 1.0 Hz, 2H), 3.79 (dd, J = 5.5, 4.3 Hz, 2H), 3.69-3.57 (m, 2H), 3.48-3.38 (m, 2H), 3.25 (s, 3H). |
| 12 | 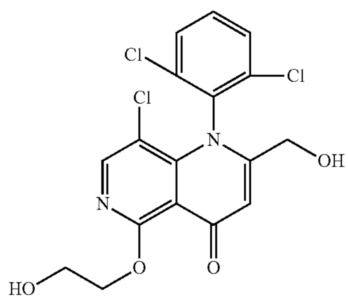 [SMILES: O=c1cc(CO)n(-c2c(Cl)cccc2Cl)c2c(Cl)cnc(OCCO)c12] | 8-chloro-1-(2,6-dichlorophenyl)-5-(2-hydroxyethoxy)-2-(hydroxymethyl)-1,6-naphthyridin-4(1H)-one | HRMS: calc. 415.0019 [M + H]+, found 415.0008; $^1$H NMR (400 MHz, DMSO-d6) δ ppm = 8.22 (s, 1H), 7.78-7.63 (m, 3H), 6.53 (s, 1H), 5.83 (s, 1H), 4.77 (t, J = 5.6 Hz, 1H), 4.42 (t, J = 5.5 Hz, 2H), 3.76 (dd, J = 11.0, 5.5 Hz, 4H) |
| 13 | 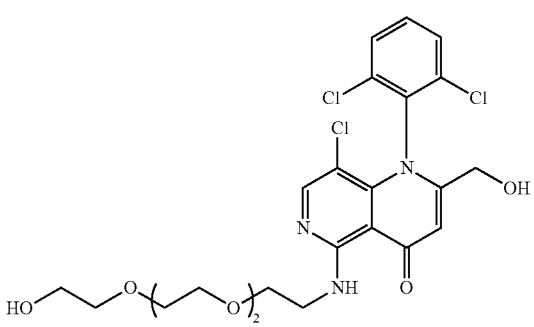 | 8-chloro-1-(2,6-dichlorophenyl)-5-((2-(2-(2-(2-hydroxy-ethoxy)ethoxy)ethoxy)ethyl)amino)-2-(hydroxymethyl)-1,6-naphthyridin-4(1H)-one | HRMS calc. 546.0966 [M + H]+; found 546.0653, $^1$H NMR (400 MHz, MeCN-d3) δ ppm = 10.73 (br s, 1 H) 7.98 (s, 1 H) 7.45-7.72 (m, 3 H) 6.41-6.88 (m, 1 H) 3.86-3.94 (m, 2 H) 3.65-3.72 (m, 4 H) 3.54-3.63 (m, 11 H) 3.46-3.52 (m, 2 H) 2.86 (t, J = 5.87 Hz, 1 H) 2.13 (s, 3H) 1.97 (s, 3 H). |
| 14 | 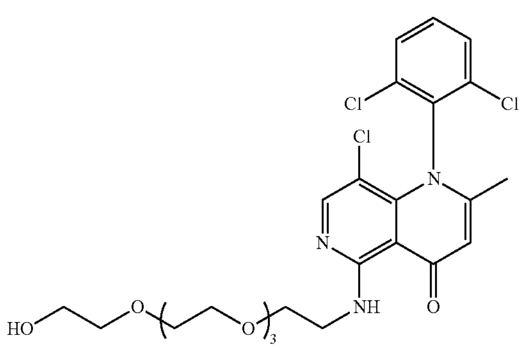 | 8-chloro-1-(2,6-dichlorophenyl)-5-((14-hydroxy-3,6,9,12-tetraoxatetradecyl)oxy)-2-methyl-1,6-naphthyridin-4(1H)-one | HRMS calc. 575.1119 [M + H]+; found 575.1125, $^1$H NMR (400 MHz, MeCN-d3) δ ppm = 8.06-8.29 (m, 1 H) 7.49-7.71 (m, 3 H) 6.38 (d, J = 0.76 Hz, 1 H) 4.44-4.74 (m, 2 H) 3.82-3.96 (m, 2 H) 3.70-3.77 (m, 2 H) 3.54-3.65 (m, 12 H) 3.45-3.50 (m, 2 H) 2.97-3.13 (m, 1 H) 1.97 (s, 3 H) |

TABLE 1-continued

Examples 2-58

| Ex. | Structure | Chemical name | Analytical data |
|---|---|---|---|
| 15 | 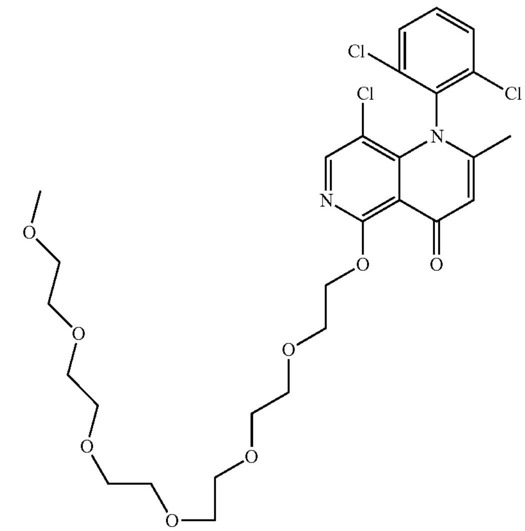 [SMILES: COCCOCCOCCOCCOCCOCCOc1ncc(Cl)c2c1c(=O)cc(C)n2-c1c(Cl)cccc1Cl] | 5-(2,5,8,11,14,17-hexaoxanonadecan-19-yloxy)-8-chloro-1-(2,6-dichlorophenyl)-2-methyl-1,6-naphthyridin-4(1H)-one | ESI-MS m/z: 635 [M + H]$^+$ (Rt = 1.08 min, LC-method 1), $^1$H NMR (400 MHz, DCM-d2) δ ppm = 8.09 (s, 1H), 7.61-7.33 (m, 3H), 6.38 (d, J = 0.8 Hz, 1H), 4.72-4.46 (m, 2H), 4.01-3.90 (m, 2H), 3.84-3.75 (m, 2H), 3.71-3.56 (m, 16H), 3.57-3.47 (m, 2H), 3.37 (s, 3H), 1.94 (d, J = 0.7 Hz, 3H). |
| 16 | 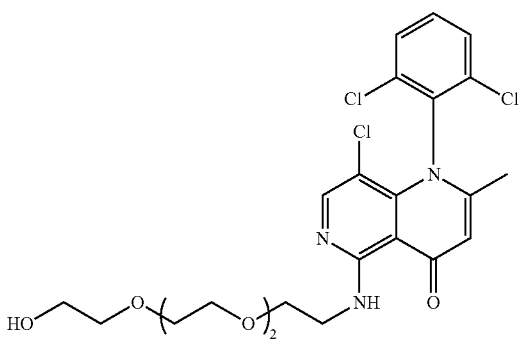 | 3-chloro-2-(8-chloro-5-((2-(2-(2-(2-hydroxy-ethoxy)ethoxy)ethoxy)ethyl)amino)-2-methyl-4-oxo-1,6-naphthyridin-1(4H)-yl)benzo-nitrile | HRMS calc. 521.1359 [M + H]$^+$; found 521.1365, $^1$H NMR (400 MHz, MeCN-d3) δ ppm = 10.67 (br s, 1H) 8.00 (s, 1 H) 7.83-7.94 (m, 2 H) 7.74 (d, J = 8.08 Hz, 1 H) 6.39 (d, J = 0.76 Hz, 1 H) 3.67 (m, 4 H) 3.59 (m, 10 H) 3.49 (m, 2 H) 2.77-2.90 (m, 1 H) 1.96 (s, 3 H) |
| 17 | 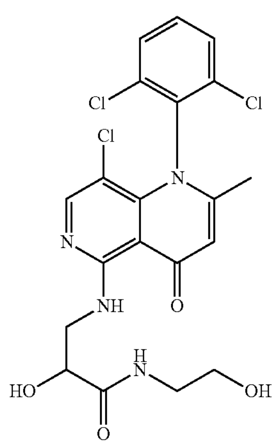 [SMILES: Cc1cc(=O)c2c(NCC(O)C(=O)NCCO)ncc(Cl)c2n1-c1c(Cl)cccc1Cl] | 3-((8-chloro-1-(2,6-dichlorophenyl)-2-methyl-4-oxo-1,4-dihydro-1,6-naphthyridin-5-yl)amino)-2-hydroxy-N-(2-hydroxyethyl)propanamide | HRMS calc. 485.0551 [M + H]$^+$; found 485.0576, $^1$H NMR (400 MHz, MeCN-d3) δ ppm = 10.72 (br s, 1 H) 7.89 (s, 1 H) 7.38-7.61 (m, 3 H) 7.11-7.30 (m, 1 H) 6.31 (d, J = 0.76 Hz, 1 H) 4.06-4.30 (m, 1 H) 3.74-3.95 (m, 1 H) 3.62 (d, J = 14.02 Hz, 1 H) 3.37-3.46 (m, 2 H) 3.33 (t, J = 5.49 Hz, 1 H) 3.05-3.27 (m, 2 H) 2.56 (t, J = 5.56 Hz, 1 H) 1.82 (d, J = 0.63 Hz, 3 H) |

TABLE 1-continued

Examples 2-58

| Ex. | Structure | Chemical name | Analytical data |
|---|---|---|---|
| 18 | 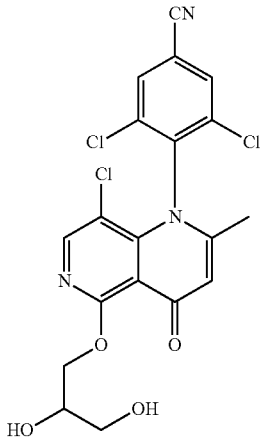 | 3,5-dichloro-4-(5-(2,3-dihydroxypropoxy)-2-methyl-4-oxo-1,7-naphthyridin-1(4H)-yl)benzonitrile | HRMS calc. 420.0518 [M + H]$^+$; found 420.0505, $^1$H NMR (400 MHz, DMSO-d6) δ ppm = 8.57 (s, 2H), 8.32 (s, 1H), 7.78 (s, 1H), 6.35 (s, 1H), 5.75 (s, 1H), 5.06 (dd, J = 8.5, 5.6 Hz, 1H), 4.80 (t, J = 6.0 Hz, 1H), 4.20 (d, J = 5.3 Hz, 2H), 3.57 (tt, J = 12.7, 6.1 Hz, 2H), 1.98 (d, J = 9.1 Hz, 3H). |
| 19 | 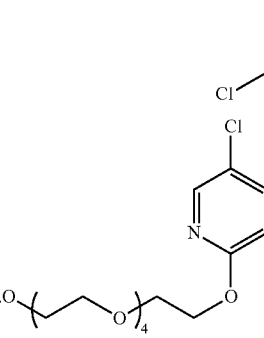 | 8-chloro-1-(2,6-dichlorophenyl)-5-((17-hydroxy-3,6,9,12,15-pentaoxaheptadecyl)oxy)-2-methyl-1,6-naphthyridin-4(1H)-one | HRMS calc. 619.1381 [M + H]$^+$; found 619.1394, $^1$H NMR (400 MHz, MeCN-d3) δ ppm = 8.13 (s, 1 H) 7.47-7.72 (m, 3 H) 6.37 (d, J = 0.76 Hz, 1 H) 4.52-4.73 (m, 2 H) 3.84-3.98 (m, 2 H) 3.67-3.80 (m, 2 H) 3.55-3.65 (m, 17 H) 3.45-3.53 (m, 2 H) 1.93 (s, 3 H) |
| 20 | 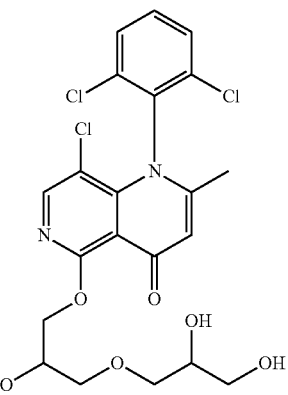 | 8-chloro-1-(2,6-dichlorophenyl)-5-(3-(2,3-dihydroxypropoxy)-2-hydroxypropoxy)-2-methyl-1,6-naphthyridin-4(1H)-one | HRMS calc. 503.0543 [M + H]$^+$; found 503.0533, $^1$H NMR (400 MHz, methanol-d4) δ ppm = 8.18 (s, 1H), 7.64 (d, J = 2.0 Hz, 3H), 6.52 (d, J = 9.0 Hz, 1H), 4.64-4.43 (m, 2H), 4.29-4.15 (m, 1H), 3.91-3.45 (m, 7H), 2.00 (d, J = 2.5 Hz, 3H). |
| 21 | 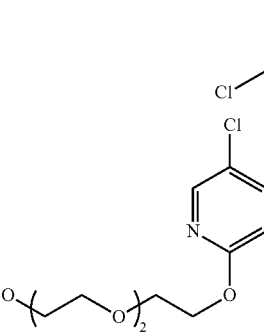 | 3-chloro-2-(8-chloro-5-(2-(2-(2-(2-hydroxyethoxy)ethoxy)ethoxy)eth-oxy)-2-methyl-4-oxo-1,6-naphthyridin-1(4H)-yl)benzonitrile | HRMS calc. 522.1199 [M + H]$^+$; found 522.1204, $^1$H NMR (400 MHz, MeCN-d3) δ ppm = 8.15 (s, 1 H) 7.92 (d, J = 2.15 Hz, 2 H) 7.77 (s, 1 H) 6.38 (d, J = 0.76 Hz, 1 H) 4.52-4.81 (m, 2 H) 3.84-3.98 (m, 2 H) 3.70-3.79 (m, 2 H) 3.57-3.65 (m, 8 H) 3.51 (d, J = 5.31 Hz, 2 H) 1.97 (s, 3 H) |

TABLE 1-continued

Examples 2-58

| Ex. | Structure | Chemical name | Analytical data |
|---|---|---|---|
| 22 | 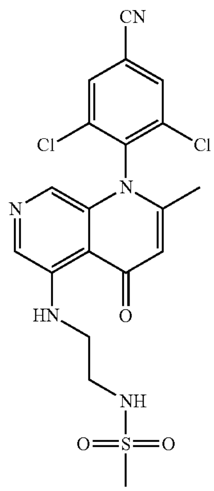 [SMILES: Cc1cc(=O)c2c(NCCNS(C)(=O)=O)cncc2n1-c1c(Cl)cc(C#N)cc1Cl] | N-(2-((1-(2,6-dichloro-4-cyanophenyl)-2-methyl-4-oxo-1,4-dihydro-1,7-naphthyridin-5-yl)amino)ethyl)methanesulfonamide | HRMS calc,. 466.0507 [M + H]+; found 466.0506, $^1$H NMR (400 MHz, DCM-d2) δ 9.78 (s, 1H), 7.97 (s, 3H), 7.11 (s, 1H), 6.37-6.17 (m, 1H), 4.74 (s, 1H), 3.58 (q, J = 5.8 Hz, 2H), 3.48 (q, J = 5.6 Hz, 2H), 3.02 (s, 3H), 2.10 (s, 3H). |
| 23 | 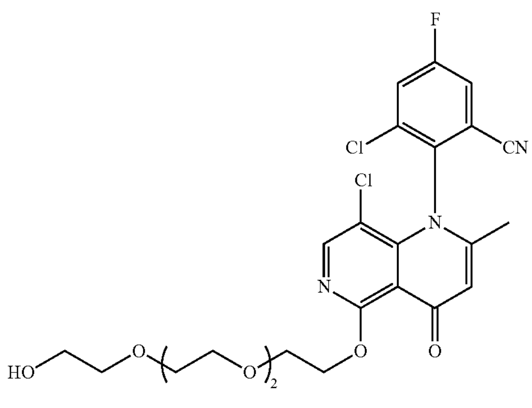 | 3-chloro-2-(8-chloro-5-(2-(2-(2-(2-hydroxyethoxy)ethoxy)ethoxy)ethoxy)-2-methyl-4-oxo-1,6-naphthyridin-1(4H)-yl)-5-fluorobenzonitrile | HRMS calc. 540.1105 [M + H]+; found 540.1110, $^1$H NMR (400 MHz, MeCN-d3) δ ppm = 8.11-8.35 (m, 1 H) 7.78 (ddd, J = 15.38, 7.86, 2.78 Hz, 2 H) 6.39 (d, J = 0.76 Hz, 1 H) 4.40-4.84 (m, 2 H) 3.83-4.01 (m, 2 H) 3.71-3.78 (m, 2 H) 3.57-3.65 (m, 8 H) 3.46-3.54 (m, 2 H) 2.92 (br s, 1 H) 1.97 (s, 3 H) |
| 24 | 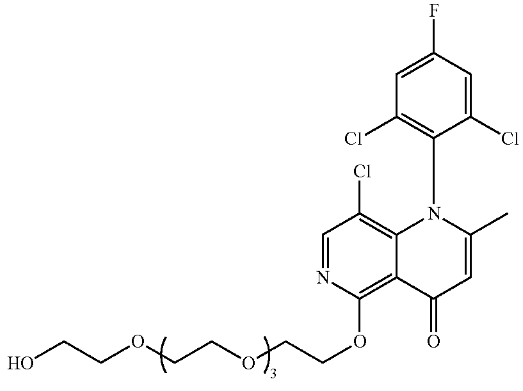 | 8-chloro-1-(2,6-dichloro-4-fluorophenyl)-5-((17-hydroxy-3,6,9,12,15-pentaoxaheptadecyl)oxy)-2-methyl-1,6-naphthyridin-4(1H)-one | HRMS: calc. 637.1287 [M + H]+, found 637.1303, $^1$H NMR (400 MHz, DMSO-d$_6$) δ ppm = 8.23 (s, 1H), 7.89 (d, J = 8.3 Hz, 2H), 6.44 (d, J = 0.8 Hz, 1H), 4.55 (t, J = 5.4 Hz, 1H), 4.48 (dd, J = 5.5, 4.2 Hz, 2H), 3.83-3.76 (m, 2H), 3.66 (dd, J = 5.7, 3.9 Hz, 2H), 3.57-3.44 (m, 16H), 3.43-3.36 (m, 2H), 1.90 (s, 3H). |

TABLE 1-continued

Examples 2-58

| Ex. | Structure | Chemical name | Analytical data |
|---|---|---|---|
| 25 | 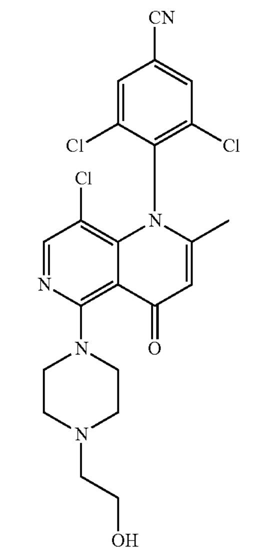 [SMILES: Cc1cc(=O)c2c(N3CCN(CCO)CC3)ncc(Cl)c2n1-c1c(Cl)cc(C#N)cc1Cl] | 3,5-dichloro-4-(8-chloro-5-(4-(2-hydroxyethyl)piperazin-1-yl)-2-methyl-4-oxo-1,6-naphthyridin-1(4H)-yl)benzonitrile | HRMS calc. 492.0751 [M + H]$^+$; found 492.0746; $^1$H NMR (400 MHz, chloroform-d3) δ ppm = 8.01 (s, 1H), 7.76 (s, 2H), 6.c33 (s, 1H), 3.75-3.49 (m, 6H), 2.67 (dt, J = 30.9, 4.8 Hz, 6H), 1.90 (s, 3H). |
| 26 | 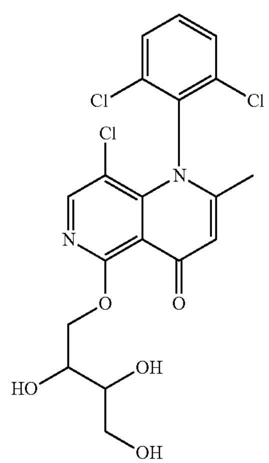 [SMILES: Cc1cc(=O)c2c(OCC(O)C(O)CO)ncc(Cl)c2n1-c1c(Cl)cccc1Cl] | 8-chloro-1-(2,6-dichlorophenyl)-2-methyl-5-(2,3,4-trihydroxybutoxy)-1,6-naphthyridin-4(1H)-one | HRMS calc. 459.0281 [M + H]$^+$; found 459.0278, $^1$H NMR (400 MHz, methanol-d4) δ ppm = 8.19 (d, J = 3.5 Hz, 1H), 7.65 (d, J = 2.2 Hz, 3H), 6.60-6.48 (m, 1H), 4.70 (dd, J = 11.3, 3.7 Hz, 1H), 4.56 (dd, J = 11.3, 5.4 Hz, 1H), 4.04-3.93 (m, 1H), 3.85-3.74 (m, 2H), 3.75-3.62 (m, 1H), 2.05-1.98 (m, 3H). |
| 27 | 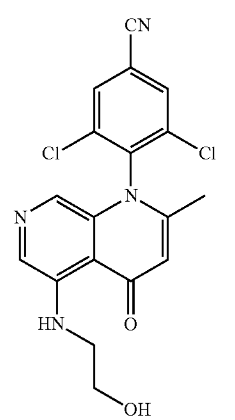 [SMILES: Cc1cc(=O)c2c(NCCO)cncc2n1-c1c(Cl)cc(C#N)cc1Cl] | 3,5-dichloro-4-(5-((2-hydroxyethyl)amino)-2-methyl-4-oxo-1,7-naphthyridin-1(4H)-yl)benzonitrile | HRMS calc. 389.0572 [M + H]$^+$; found 389.0569, $^1$H NMR (400 MHz, DMSO-d6) δ ppm = 9.54 (t, J = 5.5 Hz, 1H), 8.55 (s, 2H), 7.88 (s, 1H), 7.07 (s, 1H), 6.29 (s, 1H), 4.87 (t, J = 5.1 Hz, 1H), 3.65 (q, J = 5.4 Hz, 2H), 3.41-3.30 (q, J = 5.4 Hz, 2H), 1.95 (s, 3H). |

TABLE 1-continued

Examples 2-58

| Ex. | Structure | Chemical name | Analytical data |
|---|---|---|---|
| 28 | 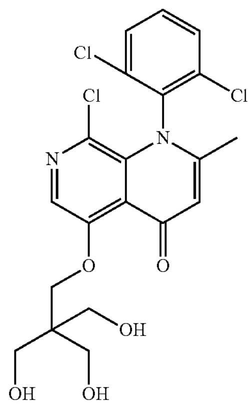 [SMILES: Cc1cc(=O)c2c(OCC(CO)(CO)CO)cnc(Cl)c2n1-c1c(Cl)cccc1Cl] | 8-chloro-1-(2,6-dichlorophenyl)-5-(3-hydroxy-2,2-bis(hydroxymethyl)propoxy)-2-methyl-1,6-naphthyridin-4(1H)-one | ESI-MS m/z: 475 [M + H]⁺ (Rt = 1.80 min, LC-method 1), ¹H NMR (400 MHz, DCM-d2) δ ppm = 8.02 (s, 1H), 7.53-7.12 (m, 3H), 6.36 (d, J = 0.7 Hz, 1H), 4.31 (s, 2H), 3.68 (s, 6H), 1.87 (d, J = 0.7 Hz, 4H). |
| 29 | 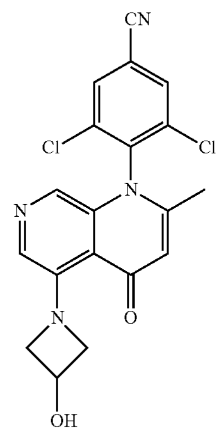 [SMILES: Cc1cc(=O)c2c(N3CC(O)C3)cncc2n1-c1c(Cl)cc(C#N)cc1Cl] | 3,5-dichloro-4-(5-(3-hydroxyazetidin-1-yl)-2-methyl-4-oxo-1,7-naphthyridin-1(4H)-yl)benzonitrile | HRMS calc. 401.0572 [M + H]⁺; found 401.0576. ¹H NMR (400 MHz, chloroform-d3) δ ppm = 7.90 (s, 2H), 7.71 (s, 1H), 7.16 (s, 1H), 6.24 (s, 1H), 4.77 (ddd, J = 10.9, 6.5, 4.4 Hz, 1H), 4.52 (dd, J = 10.1, 6.9 Hz, 2H), 4.02 (dd, J = 10.6, 4.3 Hz, 2H), 1.96 (s, 3H). |
| 30 | 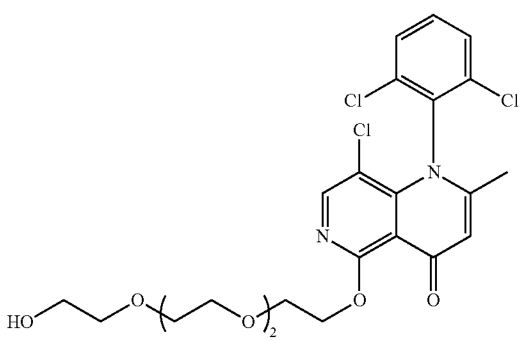 | 8-chloro-1-(2,6-dichlorophenyl)-5-(2-(2-(2-(2-hydroxyethoxy)ethoxy)ethoxy)ethoxy)-2-methyl-1,6-naphthyridin-4(1H)-one | HRMS calc. 531.0856 [M + H]⁺; found 531.0881, ¹H NMR (400 MHz, MeCN-d3) δ ppm = 8.12 (s, 1 H) 7.61 (m, 3 H) 6.30-6.44 (m, 1 H) 4.52-4.64 (m, 2 H) 3.82-3.92 (m, 2 H) 3.70-3.76 (m, 2 H) 3.56-3.64 (m, 8 H) 3.47-3.53 (m, 2 H) 2.86 (t, J = 5.87 Hz, 1 H) 1.93 (s, 3 H) |
| 31 | 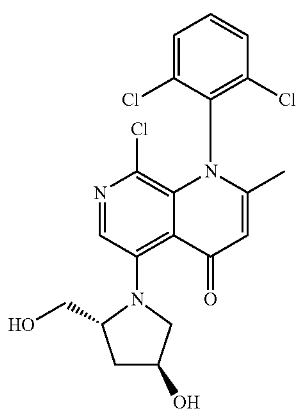 [SMILES: Cc1cc(=O)c2c(N3C[C@@H](O)C[C@@H]3CO)cnc(Cl)c2n1-c1c(Cl)cccc1Cl] | 8-chloro-1-(2,6-dichlorophenyl)-5-((2R,4S)-4-hydroxy-2-(hydroxymethyl)pyrrolidin-1-yl)-2-methyl-1,6-naphthyridin-4(1H)-one | HRMS calc. 454.0492 [M + H]⁺; found 454.0483, ¹H NMR (400 MHz, chloroform-d3) δ ppm = 7.94 (s, 1H), 7.54-7.37 (m, 3H), 6.38-6.24 (m, 1H), 4.90 (td, J = 7.0, 3.5 Hz, 1H), 4.44 (s, 1H), 4.25 (s, 1H), 4.10-3.95 (m, 2H), 3.59 (dd, J = 11.7, 3.7 Hz, 1H), 2.72 (dd, J = 12.7, 2.1 Hz, 1H), 2.52-1.95 (m, 3H), 1.95-1.87 (m, 3H). |

TABLE 1-continued

Examples 2-58

| Ex. | Structure | Chemical name | Analytical data |
|---|---|---|---|
| 32 | 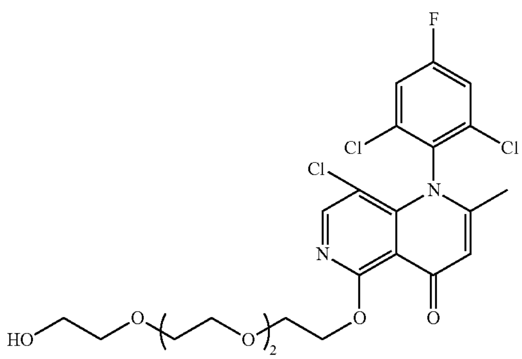 | 8-chloro-1-(2,6-dichloro-4-fluorophenyl)-5-(2-(2-(2-(2-hydroxyethoxy)ethoxy)ethoxy)ethoxy)-2-methyl-1,6-naphthyridin-4(1H)-one | HRMS calc. 549.0762 [M + H]$^+$, found 549.0756, $^1$H NMR (400 MHz, methanol-d$_4$) δ ppm = 8.19 (s, 1H), 7.59 (d, J = 8.1 Hz, 2H), 6.50 (s, 1H), 4.68-4.61 (m, 2H), 3.97-3.90 (m, 2H), 3.80-3.74 (m, 2H), 3.69-3.58 (m, 9H), 3.58-3.51 (m, 2H), 2.03-1.99 (m, 3H). |
| 33 | 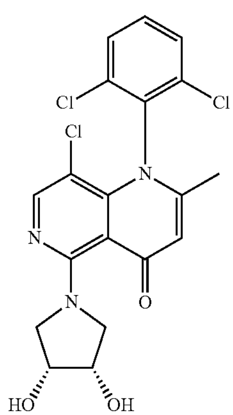 [SMILES: Cc1cc(=O)c2c(N3C[C@@H](O)[C@@H](O)C3)ncc(Cl)c2n1-c1c(Cl)cccc1Cl] | 8-chloro-1-(2,6-dichlorophenyl)-5-((3R,4S)-3,4-dihydroxypyrrolidin-1-yl)-2-methyl-1,6-naphthyridin-4(1H)-one | HRMS calc. 440.0335 [M + H]$^+$, found 440.0324; $^1$H NMR (400 MHz, methanol-d4) δ ppm = 7.99 (s, 1H), 7.69-7.52 (m, 3H), 6.42 (s, 1H), 4.25 (t, J = 4.0 Hz, 2H), 3.71 (dd, J = 11.6, 4.9 Hz, 2H), 3.42 (dd, J = 11.1, 4.2 Hz, 2H), 1.97 (s, 3H). |
| 34 | 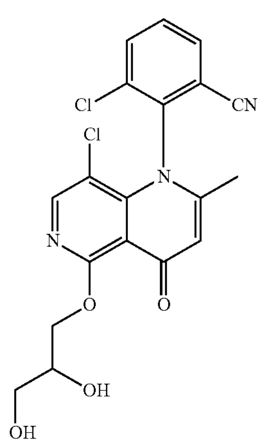 [SMILES: Cc1cc(=O)c2c(OCC(O)CO)ncc(Cl)c2n1-c1c(Cl)cccc1C#N] | 3-chloro-2-(8-chloro-5-(2,3-dihydroxypropoxy)-2-methyl-4-oxo-1,6-naphthyridin-1(4H)-yl)benzonitrile | HRMS calc. 420.0518 [M + H]$^+$, found 420.0530; 1H NMR (400 MHz, chloroform-d3) δ 8.11 (d, J = 0.7 Hz, 1H), 7.87-7.72 (m, 2H), 7.65 (t, J = 8.0 Hz, 1H), 6.46 (s, 1H), 5.16-4.83 (m, 1H), 4.77 (t, J = 12.2 Hz, 1H), 4.37 (ddd, J = 11.3, 9.9, 3.5 Hz, 1H), 4.10-3.72 (m, 4H), 1.97 (s, 3H). |

TABLE 1-continued

Examples 2-58

| Ex. | Structure | Chemical name | Analytical data |
| --- | --- | --- | --- |
| 35 | 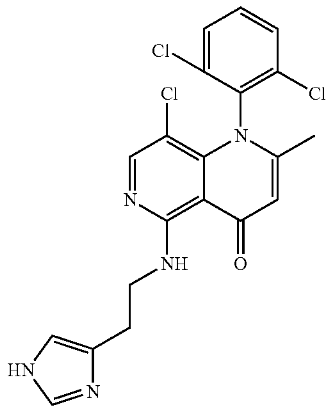 [SMILES: Cc1cc(=O)c2c(NCCc3c[nH]cn3)ncc(Cl)c2n1-c1c(Cl)cccc1Cl] | 5-((2-(1H-imidazol-4-yl)ethyl)amino)-8-chloro-1-(2,6-dichlorophenyl)-2-methyl-1,6-naphthyridin-4(1H)-one | ESI-MS m/z: 448.1 [M + H]+ (Rt = 2.08 min, LC-method 1), 1H NMR (400 MHz, DCM-d2) δ ppm = 10.73 (s, 1H), 8.02 (s, 1H), 7.64 (s, 1H), 7.59-7.38 (m, 3H), 6.94 (s, 1H), 6.36 (s, 1H), 3.92-3.71 (m, 2H), 3.01 (t, J = 6.7 Hz, 2H), 1.94 (s, 3H). |
| 36 | 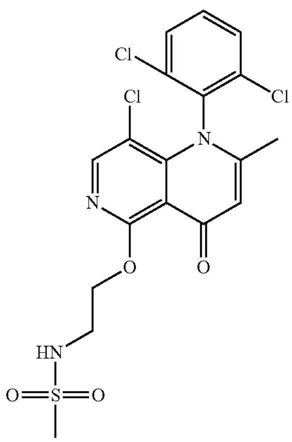 [SMILES: Cc1cc(=O)c2c(OCCNS(C)(=O)=O)ncc(Cl)c2n1-c1c(Cl)cccc1Cl] | N-(2-((8-chloro-1-(2,6-dichlorophenyl)-2-methyl-4-oxo-1,4-dihydro-1,6-naphthyridin-5-yl)oxy)ethyl)methanesulfonamide | HRMS calc. 476.0019 [M + H]+; found 476.0002, 1H NMR (400 MHz, DCM-d2) δ 8.13 ppm = (s, 1H), 7.55 (t, J = 7.4 Hz, 3H), 6.82 (bs, 1H), 6.47 (s, 1H), 4.64-4.56 (m, 2H), 3.56 (q, J = 5.1 Hz, 2H), 3.03 (s, 3H), 2.01 (s, 3H). |
| 37 | 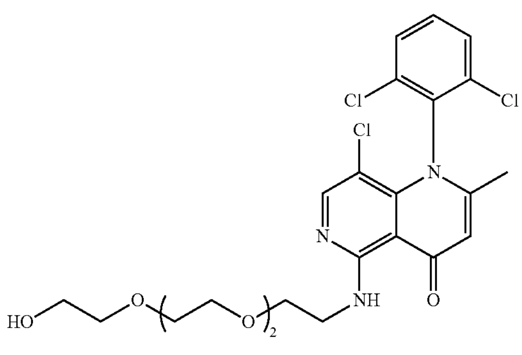 | 8-chloro-1-(2,6-dichlorophenyl)-5-((2-(2-(2-(2-hydroxyethoxy)ethoxy)ethoxy)ethyl)amino)-2-methyl-1,6-naphthyridin-4(1H)-one | HRMS calc. 530.1016 [M + H]+; found 530.1026, 1H NMR (400 MHz, MeCN-d3) δ ppm = 10.58-10.87 (m, 1 H) 7.99 (s, 1 H) 7.50-7.70 (m, 3 H) 6.39 (d, J = 0.76 Hz, 1 H) 3.56-3.76 (m, 14 H) 3.45-3.54 (m, 2 H) 2.16-2.51 (m, 1 H) 1.91 (s, 3 H) |
| 38 | 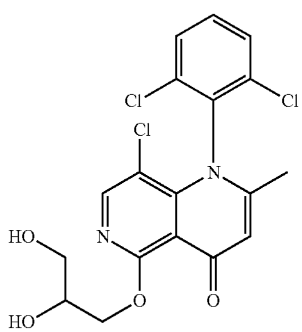 [SMILES: Cc1cc(=O)c2c(OCC(O)CO)ncc(Cl)c2n1-c1c(Cl)cccc1Cl] | 8-chloro-1-(2,6-dichlorophenyl)-5-(2,3-dihydroxypropoxy)-2-methyl-1,6-naphthyridin-4(1H)-one | HRMS calc. 429.0176 [M + H]+; found 429.0169, 1H NMR (400 MHz, chloroform-d3) δ ppm = 8.09 (s, 1H), 7.48 (s, 3H), 6.45 (s, 1H), 5.14 (dd, J = 10.4, 3.9 Hz, 1H), 4.77 (dd, J = 11.2, 2.0 Hz, 1H), 4.35 (dd, J = 11.2, 3.5 Hz, 1H), 4.09-3.70 (m, 4H), 1.94 (s, 3H). |

TABLE 1-continued

Examples 2-58

| Ex. | Structure | Chemical name | Analytical data |
|---|---|---|---|
| 39 | 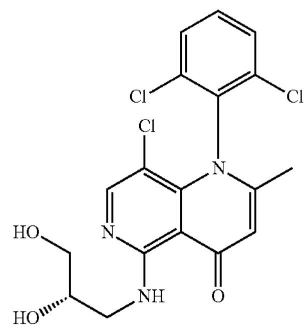 [SMILES: Cc1cc(=O)c2c(NC[C@H](O)CO)ncc(Cl)c2n1-c1c(Cl)cccc1Cl] | (S)-8-chloro-1-(2,6-dichlorophenyl)-5-((2,3-dihydroxypropyl)amino)-2-methyl-1,6-naphthyridin-4(1H)-one | HRMS calc. 428.0335 [M + H]+; found 428.0332; 1H NMR (400 MHz, chloroform-d) δ ppm = 10.88 (s, 1H), 7.92 (s, 1H), 7.54-7.37 (m, 3H), 6.54-6.26 (m, 1H), 4.29-3.40 (m, 7H), 1.92 (s, 3H). |
| 40 | 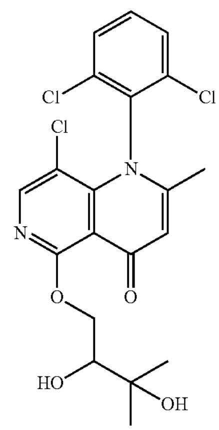 [SMILES: Cc1cc(=O)c2c(OCC(O)C(C)(C)O)ncc(Cl)c2n1-c1c(Cl)cccc1Cl] | 8-chloro-1-(2,6-chlorophenyl)-5-(2,3-dihydroxy-3-methylbutoxy)-2-methyl-1,6-naphthyridin-4(1H)-one | HRMS calc. 457.0489 [M + H]+; found 457.0499 [M + H]+, 1H NMR (400 MHz, MeCN-d3) δ ppm 8.20 (s, 1 H) 7.64 (m, 3 H) 6.53 (s, 1 H) 4.79-4.97 (m, 1 H) 4.65 (m, 1 H) 4.45 (m, 1 H) 3.81-3.95 (m, 1 H) 3.60-3.732 (m, 1 H) 2.01 (s, 3 H) 1.29 (d, J = 14.91 Hz, 6 H) |
| 41 | 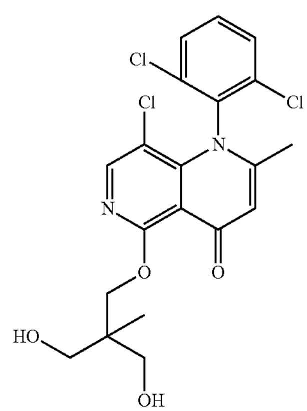 [SMILES: Cc1cc(=O)c2c(OCC(C)(CO)CO)ncc(Cl)c2n1-c1c(Cl)cccc1Cl] | 8-chloro-1-(2,6-dichlorophenyl)-5-(3-hydroxy-2-(hydroxymethyl)-2-methylpropoxy)-2-methyl-1,6-naphthyridin-4(1H)-one | ESI-MS m/z: 459.1 [M + H]+ (Rt = 2.07 min, LC-method 1), 1H NMR (400 MHz, DCM-d2) δ ppm = 8.01 (s, 1H), 7.51-7.27 (m, 3H), 6.34 (s, 1H), 4.22 (s, 2H), 3.74 (d, J = 11.5 Hz, 2H), 3.52 (d, J = 11.5 Hz, 2H), 3.44 (s, 3H), 1.86 (s, 3H). |
| 42 | 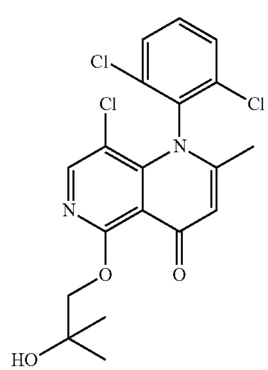 [SMILES: Cc1cc(=O)c2c(OCC(C)(C)O)ncc(Cl)c2n1-c1c(Cl)cccc1Cl] | 8-chloro-1-(2,6-dichlorophenyl)-5-(2-hydroxy-2-methylpropoxy)-2-methyl-1,6-naphthyridin-4(1H)-one | HRMS calc. 427.0383 [M + H]+; found 427.0383, 1H NMR (400 MHz, DCM-d2) δ ppm = 7.98 (s, 1H), 7.46-7.34 (m, 3H), 6.29 (s, 1H), 4.16 (s, 2H), 1.84 (s, 3H), 1.22 (s, 6H). |

TABLE 1-continued

Examples 2-58

| Ex. | Structure | Chemical name | Analytical data |
|---|---|---|---|
| 43 | 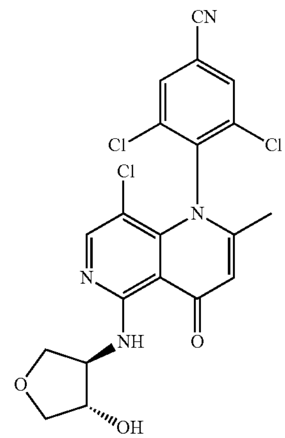 [SMILES: Cc1cc(=O)c2c(N[C@@H]3COC[C@H]3O)ncc(Cl)c2n1-c1c(Cl)cc(C#N)cc1Cl] | 3,5-dichloro-4-(8-chloro-5-(((3R,4S)-4-hydroxytetrahydrofuran-3-yl)amino)-2-methyl-4-oxo-1,6-naphthyridin-1(4H)-yl)benzonitrile | HRMS calc. 465.0288 [M + H]$^+$; found 465.0289. 1H NMR (400 MHz, Chloroform-d) δ 10.77 (d, J = 3.6 Hz, 1H), 8.01 (s, 1H), 7.78 (d, J = 0.7 Hz, 2H), 6.48-6.25 (m, 1H), 4.55 (br, s, 1H), 4.39-4.21 (m, 3H), 4.12 (dd, J = 9.6, 5.9 Hz, 1H), 3.82 (ddd, J = 12.7, 9.0, 5.1 Hz, 2H), 1.92 (s, 3H)., |
| 44 | 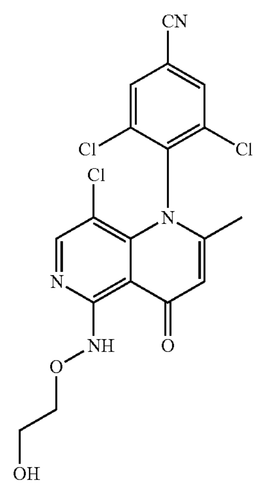 [SMILES: Cc1cc(=O)c2c(NOCCO)ncc(Cl)c2n1-c1c(Cl)cc(C#N)cc1Cl] | 3,5-dichloro-4-(8-chloro-5-((2-hydroxyethoxy)amino)-2-methyl-4-oxo-1,6-naphthyridin-1(4H)-yl)benzonitrile | HRMS calc. 439.0131 [M + H]$^+$; found 439.0126, $^1$H NMR (400 MHz, chloroform-d3) δ ppm = 12.26 (s, 1H), 8.12 (s, 1H), 7.78 (s, 2H), 6.44 (d, J = 0.8 Hz, 1H), 5.56 (s, 1H), 4.21-3.97 (m, 2H), 3.87-3.60 (m, 2H), 1.94 (d, J = 0.6 Hz, 3H). |
| 45 | 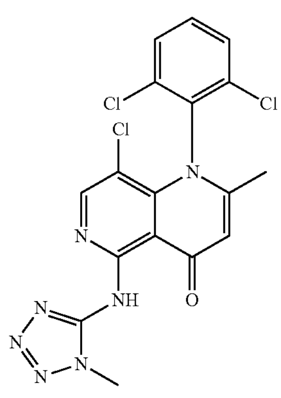 [SMILES: Cc1cc(=O)c2c(Nc3nnnn3C)ncc(Cl)c2n1-c1c(Cl)cccc1Cl] | 8-chloro-1-(2,6-dichlorophenyl)-2-methyl-5-((1-methyl-1H-tetrazol-5-yl)amino)-1,6-naphthyridin-4(1H)-one | HRMS calc. 436.0247 [M + H]$^+$; found 436.0240, $^1$H NMR (400 MHz, chloroform-d3) δ ppm = 13.45 (s, 1H), 8.20 (s, 1H), 7.50 (s, 3H), 6.53 (s, 1H), 4.01 (s, 3H), 2.01 (s, 3H). |

TABLE 1-continued

Examples 2-58

| Ex. | Structure | Chemical name | Analytical data |
|---|---|---|---|
| 46 | 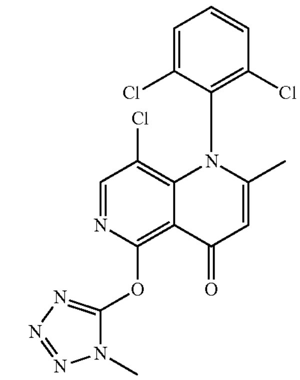 [SMILES: Cc1cc(=O)c2c(Oc3nnnn3C)ncc(Cl)c2n1-c1c(Cl)cccc1Cl] | 8-chloro-1-(2,6-dichlorophenyl)-2-methyl-5-((1-methyl-1H-tetrazol-5-yl)oxy)-1,6-naphthyridin-4(1H)-one | HRMS calc. 437.0087 [M + H]$^+$; found 437.0085, $^1$H NMR (400 MHz, chloroform-d3) δ ppm = 8.57 (s, 1H), 7.52 (d, J = 2.4 Hz, 3H), 6.42 (d, J = 0.7 Hz, 1H), 3.74 (s, 3H), 1.98 (s, 3H). |
| 47 | 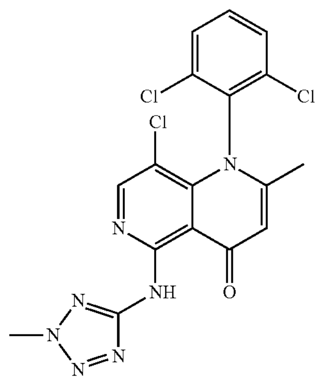 [SMILES: Cc1cc(=O)c2c(Nc3nnn(C)n3)ncc(Cl)c2n1-c1c(Cl)cccc1Cl] | 8-chloro-1-(2,6-dichlorophenyl)-2-methyl-5-((2-methyl-2H-tetrazol-5-yl)amino)-1,6-naphthyridin-4(1H)-one | HRMS calc. 436.0247 [M + H]$^+$; found 436.0257; $^1$H NMR (400 MHz, chloroform-d3) δ ppm = 13.68 (s, 1H), 8.29 (s, 1H), 7.49 (d, J = 3.4 Hz, 3H), 6.52 (s, 1H), 4.35 (s, 3H), 1.98 (s, 3H). |
| 48 | 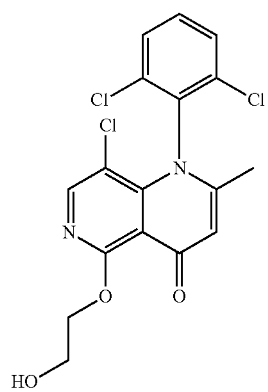 [SMILES: Cc1cc(=O)c2c(OCCO)ncc(Cl)c2n1-c1c(Cl)cccc1Cl] | 8-chloro-1-(2,6-dichlorophenyl)-5-(2-hydroxyethoxy)-2-methyl-1,6-naphthyridin-4(1H)-one | HRMS calc. 399.0070 [M + H]$^+$; found 399.0056, $^1$H NMR (400 MHz, chloroform-d3) δ ppm = 8.08 (s, 1H), 7.52-7.44 (m, 3H), 6.42 (d, J = 0.7 Hz, 1H), 4.64-4.53 (m, 2H), 4.15 (br, s, 1H), 4.01-3.87 (m, 2H), 1.94 (s, 3H). |
| 49 | 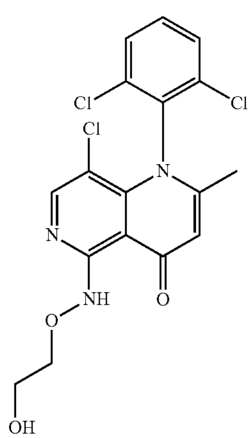 [SMILES: Cc1cc(=O)c2c(NOCCO)ncc(Cl)c2n1-c1c(Cl)cccc1Cl] | 8-chloro-1-(2,6-dichlorophenyl)-5-((2-hydroxyethoxy)amino)-2-methyl-1,6-naphthyridin-4(1H)-one | HRMS calc. 414.0179 [M + H]$^+$; found 414.0171; $^1$H NMR (400 MHz, chloroform-d3) δ ppm = 12.32 (s, 1H), 8.10 (s, 1H), 7.61-7.32 (m, 3H), 6.51-6.34 (m, 1H), 5.73 (s, 1H), 4.09 (dd, J = 5.1, 3.7 Hz, 2H), 3.76 (s, 2H), 2.07-1.80 (m, 3H). |

TABLE 1-continued

Examples 2-58

| Ex. | Structure | Chemical name | Analytical data |
|---|---|---|---|
| 50 | 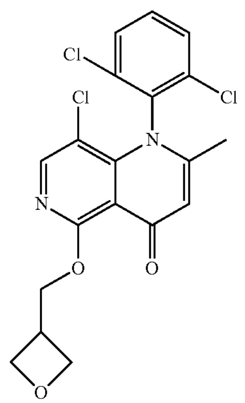 [SMILES: Cc1cc(=O)c2c(OCC3COC3)ncc(Cl)c2n1-c1c(Cl)cccc1Cl] | 8-chloro-1-(2,6-dichlorophenyl)-2-methyl-5-(oxetan-3-ylmethoxy)-1,6-naphthyridin-4(1H)-one | HRMS calc. 425.0227 [M + H]$^+$; found 425.0211, $^1$H NMR (400 MHz, DCM-d$_2$) δ ppm = 8.09 (s, 1H), 7.59-7.45 (m, 3H), 6.35 (s, 1H), 4.85 (dd, J = 7.9, 6.1 Hz, 2H), 4.73-4.59 (m, 4H), 3.64-3.49 (m, 1H), 1.94 (s, 3H). |
| 51 | 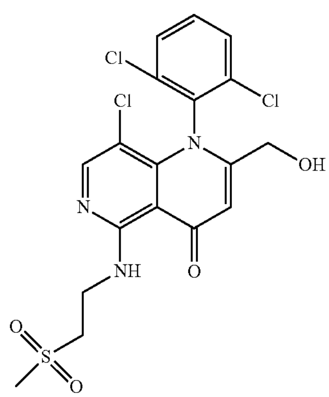 [SMILES: CS(=O)(=O)CCNc1ncc(Cl)c2c1c(=O)cc(CO)n2-c1c(Cl)cccc1Cl] | 8-chloro-1-(2,6-dichlorophenyl)-2-(hydroxymethyl)-5-((2-(methylsulfonyl)ethyl)amino)-1,6-naphthyridin-4(1H)-one | ESI-MS m/z: 477.8 [M + H]$^+$ (Rt = 0.84 min, LC-method 4), $^1$H NMR (400 MHz, DCM-d2) δ ppm = 0.62 (t, J = 5.6 Hz, 1H), 7.94 (s, 1H), 7.47-7.35 (m, 3H), 6.74 (s, 1H), 3.93 (q, J = 6.2 Hz, 4H), 3.31 (t, J = 6.6 Hz, 2H), 2.87 (s, 3H). |
| 52 | 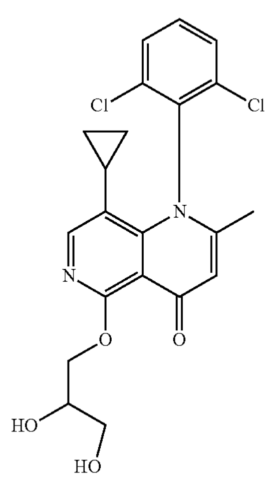 [SMILES: Cc1cc(=O)c2c(OCC(O)CO)ncc(C3CC3)c2n1-c1c(Cl)cccc1Cl] | 8-cyclopropyl-1-(2,6-dichlorophenyl)-5-(2,3-dihydroxypropoxy)-2-methyl-1,6-naphthyridin-4(1H)-one | HRMS calc. 435.0878 [M + H]$^+$; found 435.0903, $^1$H NMR (400 MHz, chloroform-d3) δ ppm = 7.69-7.46 (m, 3H), 6.35-6.24 (m, 1H), 5.82 (s, 1H), 5.49 (s, 1H), 4.73 (d, J = 11.4 Hz, 1H), 4.27 (dd, J = 11.4, 2.5 Hz, 1H), 4.16-3.72 (m, 4H), 2.04-1.87 (m, 3H), 1.69 (dd, J = 8.0, 4.6 Hz, 1H), 1.13-1.01 (m, 2H), 0.98-0.82 (m, 2H). |

TABLE 1-continued

Examples 2-58

| Ex. | Structure | Chemical name | Analytical data |
|---|---|---|---|
| 53 | 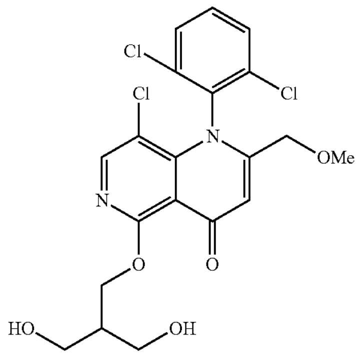 [SMILES: COCc1cc(=O)c2c(OCC(CO)CO)ncc(Cl)c2n1-c1c(Cl)cccc1Cl] | 8-chloro-1-(2,6-dichlorophenyl)-5-(3-hydroxy-2-(hydroxymethyl)propoxy)-2-(methoxymethyl)-1,6-naphthyridin-4(1H)-one | HRMS calc. 473.0438 [M + H]$^+$; found 473.0451, $^1$H NMR (400 MHz, DCM-d2) δ ppm = 8.02 (s, 1H), 7.44-7.41 (m, 3H), 7.41 (s, 3H), 6.55 (s, 1H), 4.48 (d, J = 4.8 Hz, 2H), 3.96-3.71 (m, 8H), 3.19 (s, 3H), 2.11 (d, J = 4.5 Hz, 1H). |
| 54 | 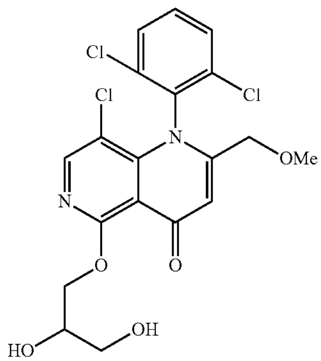 [SMILES: COCc1cc(=O)c2c(OCC(O)CO)ncc(Cl)c2n1-c1c(Cl)cccc1Cl] | 8-chloro-1-(2,6-dichlorophenyl)-5-(2,3-dihydroxypropoxy)-2-(methoxymethyl)-1,6-naphthyridin-4(1H)-one | HRMS calc. 459.0281 [M + H]$^+$; found 459.0286, $^1$H NMR (400 MHz, DCM-d2) δ ppm = 8.03 (s, 1H), 7.50-7.36 (m, 3H), 6.56 (s, 1H), 4.88 (td, J = 11.0, 9.4, 5.6 Hz, 1H), 4.62 (ddd, J = 11.2, 2.2, 1.2 Hz, 1H), 4.25 (dd, J = 11.2, 3.6 Hz, 1H), 3.85 (d, J = 12.2 Hz, 2H), 3.76 (s, 2H), 3.75-3.64 (m, 2H), 3.19 (s, 3H). |
| 55 | 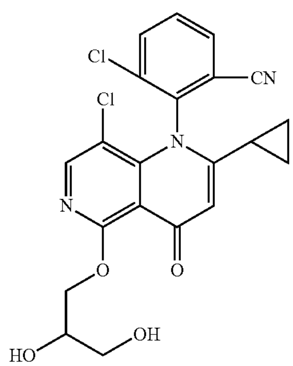 [SMILES: N#Cc1cccc(Cl)c1-n1c(C2CC2)cc(=O)c2c(OCC(O)CO)ncc(Cl)c21] | 3-chloro-2-(8-chloro-2-cyclopropyl-5-(2,3-dihydroxypropoxy)-4-oxo-1,6-naphthyridin-1(4H)-yl)benzonitrile | ESI-MS m/z: 446.1 [M + H]$^+$ (Rt = 1.67 min, LC-method 1), $^1$H NMR (400 MHz, DCM-d2) δ ppm = 8.17 (s, 1H), 7.83 (ddt, J = 8.8, 6.4, 1.4 Hz, 2H), 7.75-7.62 (m, 1H), 6.34 (s, 1H), 4.73 (ddd, J = 10.2, 8.5, 1.7 Hz, 1H), 4.38 (ddd, J = 11.2, 6.0, 3.6 Hz, 1H), 4.07-3.91 (m, 2H), 3.87-3.73 (m, 2H), 1.38-1.19 (m, 1H), 0.88 (dtt, J = 11.3, 7.7, 4.1 Hz, 2H), 0.82-0.68 (m, 2H). |
| 56 | 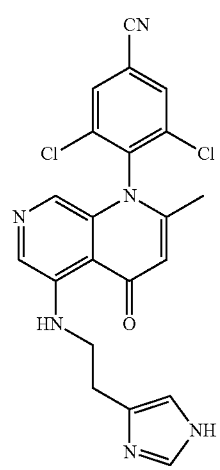 [SMILES: Cc1cc(=O)c2c(NCCc3c[nH]cn3)cncc2n1-c1c(Cl)cc(C#N)cc1Cl] | 4-(5-((2-(1H-imidazol-4-yl)ethyl)amino)-2-methyl-4-oxo-1,7-naphthyridin-1(4H)-yl)-3,5-dichlorobenzonitrile | HRMS calc. 439.0841 [M + H]$^+$; found 439.0828, $^1$H NMR (400 MHz, DMSO-d6) δ ppm = 9.48 (dt, J = 20.1, 5.4 Hz, 1H), 8.54 (s, 3H), 7.91 (d, J = 24.6 Hz, 1H), 7.54 (d, J = 8.7 Hz, 1H), 7.09 (d, J = 12.5 Hz, 1H), 6.32-6.18 (m, 1H), 5.75 (s, 1H), 3.00-2.87 (m, 2H), 2.83 (t, J = 6.8 Hz, 2H). |

TABLE 1-continued

Examples 2-58

| Ex. | Structure | Chemical name | Analytical data |
|---|---|---|---|
| 57 | 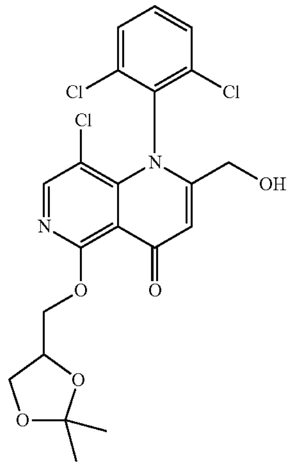 [SMILES: CC1(C)OCC(COc2ncc(Cl)c3c2c(=O)cc(CO)n3-c2c(Cl)cccc2Cl)O1] | 8-chloro-1-(2,6-dichlorophenyl)-5-((2,2-dimethyl-1,3-dioxolan-4-yl)methoxy)-2-(hydroxymethyl)-1,6-naphthyridin-4(1H)-one | ESI-MS m/z: 487 [M + H]$^+$ (Rt = 1.05 min, LC-method 1), $^1$H NMR (400 MHz, DCM-d2) δ ppm = 8.14 (s, 1H), 7.54 (d, J = 1.9 Hz, 3H), 6.99 (s, 1H), 4.66-4.46 (m, 3H), 4.28-4.17 (m, 1H), 4.15-3.96 (m, 3H), 1.47 (s, 3H), 1.41 (s, 3H). |

Chiral Separation of the Racemic Compound of Example 40

Examples 58 and 59: One of Examples 58 and 59 is (R)-8-Chloro-1-(2,6-dichlorophenyl)-5-(2,3-dihydroxy-3-methylbutoxy)-2-methyl-1,6-naphthyridin-4(1H)-one and the other is (S)-8-Chloro-1-(2,6-dichlorophenyl)-5-(2,3-dihydroxy-3-methylbutoxy)-2-methyl-1,6-naphthyridin-4(1H)-one 8-chloro-1-(2,6-dichlorophenyl)-5-(2,3-dihydroxy-3-methylbutoxy)-2-methyl-1,6-naphthyridin-4(1H)-one was dissolved in methanol and submitted in multiple injections of 1.6 ml each to chiral preparative SFC (ChiralPak AD-H column, 250×330 mm ID, 5 μm, flow rate of 80 ml/min at 38° C.) using 35% 2-propanol in carbon dioxide as mobile phase. After chiral separation, the fractions were dried off via rotary evaporation to give example 58 as the first eluting peak (>99% ee) and example 59 as the second eluting peak (>99% ee) as white solids. Retention times were obtained on an ChiralPak AD-H column, 4.6×100 mm, 5 μm column, A gradient of 5-55% 2-propanol in carbon dioxide as mobile phase was applied over 5.5 min, then held for 0.1 min (5.0 ml/min as solvent flow) at an oven temperature of 38° C. (Example 58: Rt=4.23 min; Example 59: Rt=4.68 min)

The following examples were prepared as described in Scheme B

Example 60: 8-Chloro-1-(2,6-dichloro-4-fluorophenyl)-5-(2,3-dihydroxypropoxy)-2-(hydroxymethyl)-1,6-naphthyridin-4(1H)-one

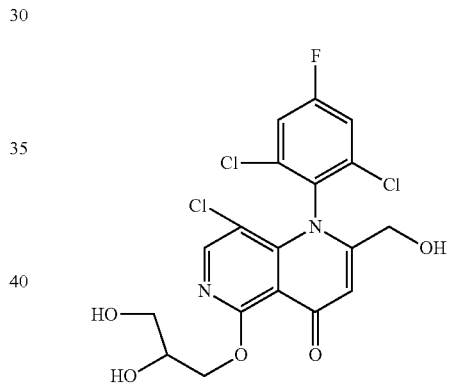

Step 1: 8-Chloro-1-(2,6-dichloro-4-fluorophenyl)-5-((2,2-dimethyl-1,3-dioxolan-4-yl)methoxy)-2-methyl-1,6-naphthyridin-4(1H)-one

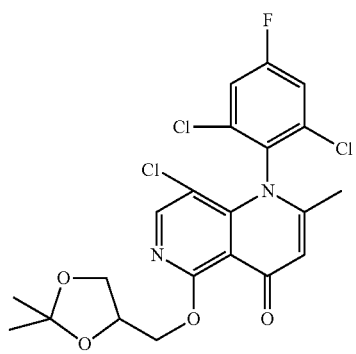

A mixture of 5,8-dichloro-1-(2,6-dichloro-4-fluorophenyl)-2-methyl-1,6-naphthyridin-4(1H)-one (intermediate 2, 0.4 g, 1.02 mmol), (2,2-dimethyl-1,3-dioxolan-4-yl)methanol (0.674 g, 5.10 mmol), K$_2$CO$_3$ (0.423 g, 3.06 mmol) and DMAP (0.037 g, 0.306 mmol) in acetonitrile (10 mL) was stirred at 80° C. for 2 days. The solid was filtered out and the reaction mixture was then purified with silica-gel chromatography (10-50% EtOAc/heptane) to afford white solid as the title compound (0.436 g, 88%). ESI-MS m/z: 489.1 [M+H]$^+$ (Rt=1.42 min, LC-method 3)

Step 2: 8-Chloro-1-(2,6-dichloro-4-fluorophenyl)-5-(2,3-dihydroxpropoxy)-4-oxo-1,4-dihydro-1,6-naphthyridine-2-carbaldehyde

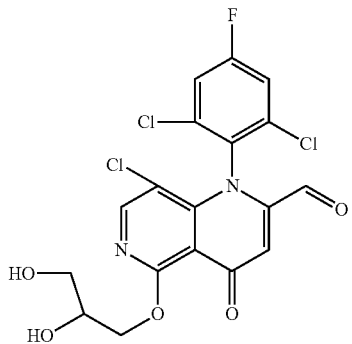 [SMILES: O=Cc1cc(=O)c2c(OCC(O)CO)ncc(Cl)c2n1-c1c(Cl)cc(F)cc1Cl]

A mixture of 8-chloro-1-(2,6-dichloro-4-fluorophenyl)-5-((2,2-dimethyl-1,3-dioxolan-4-yl)methoxy)-2-methyl-1,6-naphthyridin-4(1H)-one (0.104 g, 0.213 mmol) and SeO$_2$ (0.036 g, 0.32 mmol) in 1,4-dioxane (2 mL) was stirred at 90° C. overnight. Another batch of SeO$_2$ (0.030 g, 0.27 mmol) was added to the reaction mixture followed by stirring at 100° C. overnight. The solid was filtered out. Volatiles were removed under reduced pressure to afford crude product. LC-MS indicate the title compound is the major component of the crude product. ESI-MS m/z: 463.1 [M+H]$^+$ (Rt=1.02 min, LC-method 3)

Step 3: 8-Chloro-1-(2,6-dichloro-4-fluorophenyl)-5-(2,3-dihydroxpropoxy)-2-(hydroxymethyl)-1,6-naphthyridin-4(1H)-one

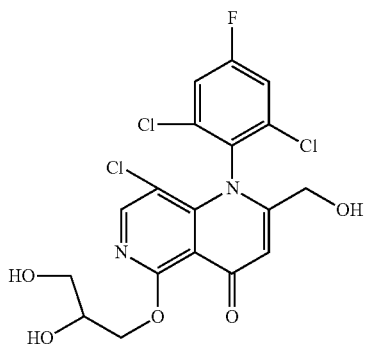 [SMILES: O=c1cc(CO)n(-c2c(Cl)cc(F)cc2Cl)c2c(Cl)cnc(OCC(O)CO)c12]

To a solution of crude 8-chloro-1-(2,6-dichloro-4-fluorophenyl)-5-(2,3-dihydroxypropoxy)-4-oxo-1,4-dihydro-1,6-naphthyridine-2-carbaldehyde (0.098 g, 0.213 mmol) in EtOH (5 mL) was added NaBH$_4$ (0.04 g, 1.07 mmol). The reaction mixture was stirred at 60° C. for 5 min. The solid was filtered out followed by purifying with reverse phase HPLC (X-bridge 30×50 mm 5 um column, ACN/H$_2$O with 10 mM NH$_4$OH, 75 mL/min, 1.5 mL injection, gradient: 15-40% ACN in 3.5 min.) to afford white solid as the title compound (0.027 g, 26%).

60: HRMS: calc. 463.0031 [M+H]$^+$, found 463.0036; $^1$H NMR (400 MHz, DMSO-d6) δ ppm=8.26 (s, 1H), 7.88 (d, J=8.3 Hz, 2H), 6.55 (s, 1H), 5.85 (bs, 1H), 4.88 (bs, 1H), 4.75 (bs, 1H), 4.38 (dd, J=10.7, 5.5 Hz, 1H), 4.30 (dd, J=10.7, 5.8 Hz, 1H), 3.78-3.91 (m, 3H), 3.58 (m, 2H)

The following example was prepared by an analogous method as described for the above example using ethan-1,2-diol in step 1.

Example 61: 8-Chloro-1-(2,6-dichloro-4-fluorophenyl)-5-(2-hydroxyethoxy)-2-(hydroxymethyl)-1,6-naphthyridin-4(1H)-one

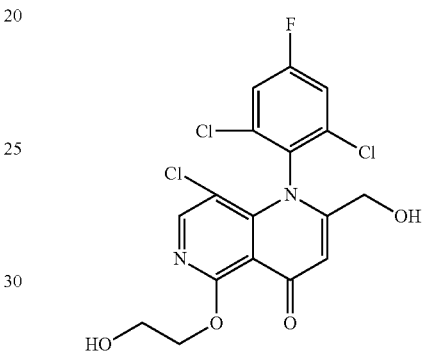

61: HRMS: calc. 432.9925 [M+H]$^+$, found 432.9919; $^1$H NMR (400 MHz, DMSO-d6) δ ppm=8.23 (s, 1H), 7.88 (d, J=8.3 Hz, 2H), 6.52 (s, 1H), 5.82 (bs, 1H), 4.77 (bs, 1H), 4.42 (t, J=5.5 Hz, 2H), 3.81 (s, 2H), 3.76 (q, J=4.4 Hz, 2H)

Example 62: 8-Chloro-1-(2,6-dichlorophenyl)-2-(difluoromethyl)-5-(2,3-dihydroxypropoxy)-1,6-naphthyridin-4(1H)-one

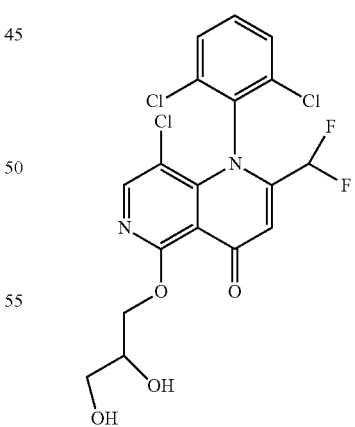

Step 1: 8-Chloro-1-(2,6-dichlorophenyl)-5-((2,2-dimethyl-1,3-dioxolan-4-yl)methoxy)-2-methyl-1,6-naphthyridin-4(1H)-one To a solution of 5,8-dichloro-1-(2,6-dichlorophenyl)-2-methyl-1,6-naphthyridin-4(1H)-one (0.250 g, 0.668 mmol)

in NMP (1 ml) was added (2,2-dimethyl-1,3-dioxolan-4-yl)methanol (0.883 g, 6.68 mmol), K$_2$CO$_3$ (0.277 g, 2.005 mmol) and DMAP (0.008 g 0.067 mmol). The resulting solution was heated at 75° C. for 1 hr. The reaction mixture was taken into EtOAc/water mixture. Aqueous layer was extracted with EtOAc. Combined organic layers were dried over anhydrous Na$_2$SO$_4$, filtered and evaporated. The crude was purified with silica-gel chromatography (10-100% EtOAc in heptane) to give the title compound (0.277 g, 79%). ESI-MS m/z: 471.1 [M+H]$^+$ (Rt=1.17 min, LC-method 1), $^1$H NMR (400 MHz, DCM-d2) δ ppm=8.09 (s, 1H), 7.61-7.41 (m, 3H), 6.40 (d, J=0.7 Hz, 1H), 4.62-4.45 (m, 3H), 4.20 (dd, J=8.5, 6.1 Hz, 1H), 4.04 (dd, J=8.4, 6.2 Hz, 1H), 1.95 (s, 3H), 1.47 (s, 3H), 1.41 (s, 3H).

Step 2: 8-Chloro-1-(2,6-dichlorophenyl)-5-((2,2-dimethyl-1,3-dioxolan-4-yl)methoxy)-4-oxo-1,4-dihydro-1,6-naphthyridine-2-carbaldehyde A mixture of 8-chloro-1-(2,6-dichlorophenyl)-5-(3-hydroxy-2-(hydroxymethyl)propoxy)-2-methyl-1,6-naphthyridin-4(1H)-one (0.123 g, 0.262 mmol) and selenium dioxide (0.035 g, 0.314 mmol) in 1,4-dioxane (5 mL) was refluxed overnight. Insolubles were filtered off and washed with EtOAc. The organic layer was concentrated under reduced pressure. To the residue was added EtOAc and water. The organic layer was separated and the aq. layer was extracted with EtOAc. Combined organic layer was dried over anhydrous Na$_2$SO$_4$, filtered and evaporated. The crude was purified with silica-gel chromatography (10-100% EtOAc in heptane) to give the title compound (0.057 g, 45%).

Step 3: 8-Chloro-1-(2,6-dichlorophenyl)-2-(difluoromethyl)-5-((2,2-dimethyl-1,3-dioxolan-4-yl)methoxy)-1,6-naphthyridin-4(1H)-one To a solution of 8-chloro-1-(2,6-dichlorophenyl)-5-((2,2-dimethyl-1,3-dioxolan-4-yl)methoxy)-4-oxo-1,4-dihydro-1,6-naphthyridine-2-carbaldehyde (0.056 g, 0.116 mmol) in 2 ml of DCM was added DeoxoFluor (0.320 ml, 1.737 mmol). The resulting mixture was stirred at room temperature over the weekend. It was quenched with a 10% NaHCO$_3$ solution at 0° C., then extracted with CH$_2$Cl$_2$. The combined organic layers were washed with brine, dried over anhydrous Na$_2$SO$_4$, filtered and concentrated under reduced pressure to dryness. The residue was purified with silica-gel chromatography (10-100% EtOAc in heptane) to give the title compound (0.025 g, 43% yield). ESI-MS m/z: 505.1 [M+H]$^+$ (Rt=1.23 min, LC-method 1).

Step 4: 8-Chloro-1-(2,6-dichlorophenyl)-2-(difluoromethyl)-5-(2,3-dihydroxypropoxy)-1,6-naphthyridin-4(1H)-one To a solution of 8-chloro-1-(2,6-dichlorophenyl)-2-(difluoromethyl)-5-((2,2-dimethyl-1,3-dioxolan-4-yl)methoxy)-1,6-naphthyridin-4(1H)-one (0.025 g, 0.049 mmol) in 0.5 ml of DCM was added 0.5 ml of TFA. The reaction mixture was stirred 1.5 hours. Then it was concentrated. The residue was diluted with ACN and filtered through LP-HCO3 resin to neutralize the TFA salt. The filtrate was concentrated to provide the title compound (0.020 g, 78% yield).

62: ESI-MS m/z: 467.1 [M+H]$^+$ (Rt=1.91 min, LC-method 1); $^1$H NMR (400 MHz, DCM-d2) δ ppm=8.09 (s, 1H), 7.56-7.36 (m, 3H), 6.78 (s, 1H), 5.99 (t, J=53.0 Hz, 1H), 4.64 (ddd, J=11.2, 2.4, 1.2 Hz, 1H), 4.27 (dd, J=11.2, 3.7 Hz, 1H), 3.98-3.79 (m, 2H), 3.77-3.61 (m, 1H).

Example 63: 8-Chloro-1-(2,6-dichlorophenyl)-5-(2,3-dihydroxypropoxy)-4-oxo-1,4-dihydro-1,6-naphthyridine-2-carbonitrile

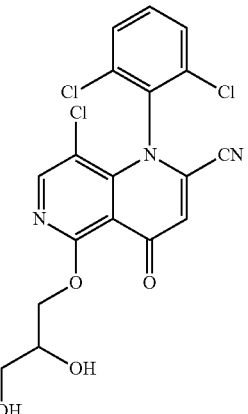

8-Chloro-1-(2,6-dichlorophenyl)-5-((2,2-dimethyl-1,3-dioxolan-4-yl)methoxy)-4-oxo-1,4-dihydro-1,6-naphthyridine-2-carbaldehyde was prepared as described in example 63 in step 1 and 2.

Step 3: 8-Chloro-1-(2,6-dichlorophenyl)-5-(2,3-dihydroxypropoxy)-4-oxo-1,4-dihydro-1,6-naphthyridine-2-carboxylic acid

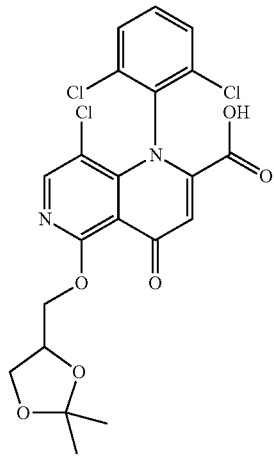 [SMILES: CC1(C)OCC(COc2ncc(Cl)c3c2c(=O)cc(C(=O)O)n3-c2c(Cl)cccc2Cl)O1]

To a solution of 8-chloro-1-(2,6-dichlorophenyl)-5-((2,2-dimethyl-1,3-dioxolan-4-yl)methoxy)-4-oxo-1,4-dihydro-1,6-naphthyridine-2-carbaldehyde (0.358 g, 0.740 mmol) in acetone (1 ml) and water (1 ml) mixture were added sodium chlorite (0.134 g, 1.48 mmol) and sulfamic acid (0.216 g, 2.22 mmol). The mixture was stirred at room temperature overnight. The solvent was removed. The residue was washed with water, filtered and dried under vacuum. It was used as it was for the next step. ESI-MS m/z: 460.9 [M+H]$^+$ (Rt=0.46 min, LC-method 4), $^1$H NMR (400 MHz, DMSO-d6) δ ppm=8.19 (s, 1H), 7.48 (d, J=4.2 Hz, 3H), 6.14 (s, 1H), 4.97-4.79 (m, 2H), 4.38 (dd, J=10.6, 5.5 Hz, 1H), 4.26 (dd, J=10.6, 6.0 Hz, 1H), 3.92-3.79 (m, 1H), 3.57 (dq, J=10.8, 5.5 Hz, 2H).

Step 4: 8-Chloro-1-(2,6-dichlorophenyl)-5-(2,3-dihydroxypropoxy)-4-oxo-1,4-dihydro-1,6-naphthyridine-2-carboxamide

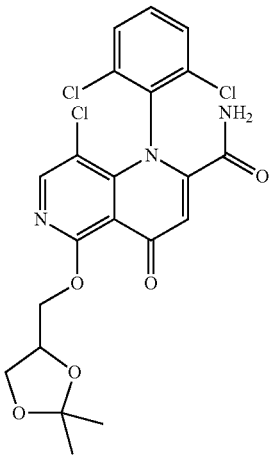 [SMILES: CC1(C)OCC(COc2ncc(Cl)c3c2c(=O)cc(C(N)=O)n3-c2c(Cl)cccc2Cl)O1]

To a solution of 8-chloro-1-(2,6-dichlorophenyl)-5-(2,3-dihydroxypropoxy)-4-oxo-1,4-dihydro-1,6-naphthyridine-2-carboxylic acid (0.160 g, 0.348 mmol), HATU (0.397 g, 1.044 mmol), and DIEA (0.304 ml, 1.74 mmol) in DMF (4 ml) was added ammonium chloride (0.056 g, 1.044 mmol). The mixture was stirred at room temperature overnight. The reaction mixture was diluted with EtOAc and washed with water. The aq. layer was extracted with EtOAc. Combined organic layer was dried over anhydrous $Na_2SO_4$, filtered and concentrated under reduced pressure. The residue was purified with silica-gel chromatography (0-10% MeOH in DCM) to give the title compound (0.132 g, 83%). ESI-MS m/z: 458.0 [M+H]$^+$ (Rt=0.68 min, LC-method 4), $^1$H NMR (400 MHz, DMSO-d6) δ ppm=8.38 (s, 1H), 8.29 (s, 1H), 7.79 (s, 1H), 7.66-7.50 (m, 3H), 6.42 (s, 1H), 4.88 (d, J=5.2 Hz, 1H), 4.71 (t, J=5.9 Hz, 1H), 4.44-4.21 (m, 2H), 3.87 (q, J=5.3 Hz, 1H), 3.66-3.48 (m, 2H).

Step 5: 8-Chloro-1-(2,6-dichlorophenyl)-5-(2,3-dihydroxypropoxy)-4-oxo-1,4-dihydro-1,6-naphthyridine-2-carbonitrile

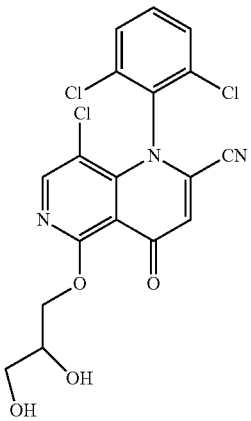 [SMILES: N#Cc1cc(=O)c2c(OCC(O)CO)ncc(Cl)c2n1-c1c(Cl)cccc1Cl]

To a solution of 8-chloro-1-(2,6-dichlorophenyl)-5-(2,3-dihydroxypropoxy)-4-oxo-1,4-dihydro-1,6-naphthyridine-2-carboxamide (0.130 g, 0.283 mmol) in THF (3 mL) and TEA (0.099 ml, 0.709 mmol) was added TFAA (0.140 mL, 0.992 mmol) dropwise at 0° C. (internal temperature did not exceed 15° C.—monitored using an internal thermometer). Reaction was stirred at 0° C. for 2 hours. Then it was poured into water and the product was extracted with EtOAc (3×). The combined organic layers are washed with saturated aqueous $NaHCO_3$ solution, brine, and dried over anhydrous $Na_2SO_4$, filtered and concentrated. The crude was purified with silica-gel chromatography (0-10% MeOH in DCM) to give the title compound (0.09 g, 72%).

63: ESI-MS m/z: 442.0 [M+H]$^+$ (Rt=0.68 min, LC-method 4), $^1$H NMR (400 MHz, DCM-d2) δ ppm=8.25 (s, 1H), 7.61 (d, J=4.5 Hz, 3H), 6.99 (s, 1H), 4.70-4.59 (m, 4H), 4.52 (dd, J=10.9, 5.6 Hz, 1H), 4.39 (dt, J=11.1, 5.6 Hz, 2H).

Example 64: 8-Chloro-1-(2,6-dichlorophenyl)-5-hydroxy-2-(hydroxymethyl)-1,6-naphthyridin-4(1H)-one

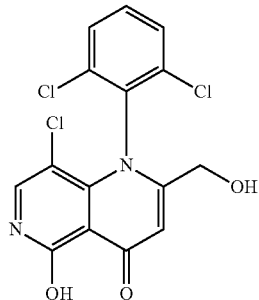 [SMILES: O=c1cc(CO)n(-c2c(Cl)cccc2Cl)c2c(Cl)cnc(O)c12]

To a solution of 2-(((tert-butyldimethylsilyl)oxy)methyl)-5,8-dichloro-1-(2,6-dichlorophenyl)-1,6-naphthyridin-4(1H)-one (intermediate 7, 0.1 g, 0.198 mmol) in water (5 ml) was added 1N HCl (5 ml). The resulting mixture was stirred at 80° C. overnight. It was neutralized with saturated aqueous $NaHCO_3$ solution and desired product was extracted with EtOAc. The combined organic layers were dried over anhydrous $Na_2SO_4$, filtered, and concentrated. The residue was triturated with the mixture of MeCN and heptane to give the title compound (0.043 g, 55% yield). 64: ESI-MS m/z: 372.8 [M+H]$^+$ (Rt=0.88 min, LC-method 1), $^1$H NMR (400 MHz, DCM-d2) δ ppm=8.19 (s, 1H), 7.57 (d, J=2.8 Hz, 3H), 7.01 (s, 1H), 4.23-4.08 (m, 2H).

Example 65: 1-(2,6-Dichlorophenyl)-5-(2,3-dihydroxpropoxy)-2-methyl-7-(methylamino)-1,6-naphthyridin-4(1H)-one

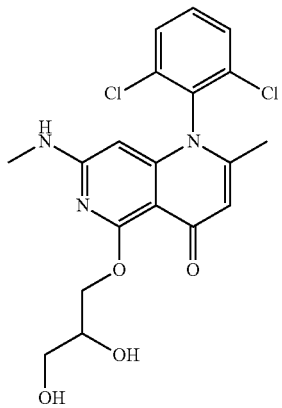

Step 1: 7-Chloro-1-(2,6-dichlorophenyl)-5-((2,2-dimethyl-1,3-dioxolan-4-yl)methoxy)-2-methyl-1,6-naphthyridin-4(1H)-one

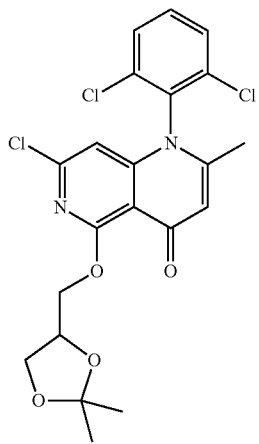 [SMILES: Cc1cc(=O)c2c(OCC3COC(C)(C)O3)nc(Cl)cc2n1-c1c(Cl)cccc1Cl]

To a solution of intermediate 11 (1 g, 2.67 mmol) in NMP (8 ml) was added DMAP (0.163 g, 1.337 mmol), K$_2$CO$_3$ (1.108 g, 8.02 mmol) and (2,2-dimethyl-1,3-dioxolan-4-yl)methanol (1.060 g, 8.02 mmol) at rt. The resulting solution was stirred at 75° C. for 1 hour. The reaction was cooled to rt, quenched with brine, extracted with EtOAC. The organic phase was washed with water, brine, dried over MgSO$_4$, and concentrated in vacuo. The crude residue was purified by column chromatography on silica gel eluting with 0-100% EtOAc/Heptane, then 5% MeOH/EtOAc, to provide the title compound as white solid (0.51 g, 40.6% yield). LC/MS (m/z, [M+H]$^+$): 471.1

Step 2: 1-(2,6-Dichlorophenyl)-5-(2,3-dihydroxpropoxy)-2-methyl-7-(methylamino)-1,6-naphthyridin-4(1H)-one To a solution of 7-Chloro-1-(2,6-dichlorophenyl)-5-((2,2-dimethyl-1,3-dioxolan-4-yl)methoxy)-2-methyl-1,6-naphthyridin-4(1H)-one (20 mg, 0.043 mmol) in Hünig's base (0.074 ml, 0.426 mmol) and NMP (0.5 ml) was added methylamine hydrochloride and the reaction was heated at 90° C. overnight. The reaction was filtered and purified by basic preparative HPLC (Waters Xbridge 5 um 30×100 mm, Water/Acetonitrile with 10 mM NH4OH, 75 mL/min, 1.5 mL injection, 30-45% ACN at 11.5 min) to afford the desired the product as white powder. This white powder was dissolved in DCM (1 ml) and TFA (1 ml) was added. The resulting solution was stirred at rt overnight. The reaction mixture was concentrated, neutralized with conc. ammonia, and then purified by basic preparative HPLC (Waters Xbridge 5 um 30×100 mm, Water/Acetonitrile with 10 mM NH4OH, 75 mL/min, 1.5 mL injection, 20-35% ACN at 11.5 min) to afford the title compound as an off white powder (8.9 mg, 0.021 mmol)

65: HRMS: calc. 424.0844 [M+H]$_+$, found 424.0830; $^1$H NMR (400 MHz, chloroform-d3) δ ppm=7.56-7.46 (m, 2H), 7.40 (dd, J=8.6, 7.5 Hz, 1H), 6.09-5.99 (m, 1H), 5.67 (s, 1H), 4.72-4.51 (m, 3H), 4.18 (d, J=9.8 Hz, 1H), 4.02-3.70 (m, 4H), 2.64 (d, J=5.1 Hz, 3H), 1.88-1.76 (m, 3H).

Example 66: 1-(2,6-Dichlorophenyl)-5-(2,3-dihydroxpropoxy)-7-ethyl-2-methyl-1,6-naphthyridin-4(1H)-one and example 67: 1-(2-Chloro-6-ethylphenyl)-5-(2,3-dihydroxypropoxy)-7-ethyl-2-methyl-1,6-naphthyridin-4(1H)-one

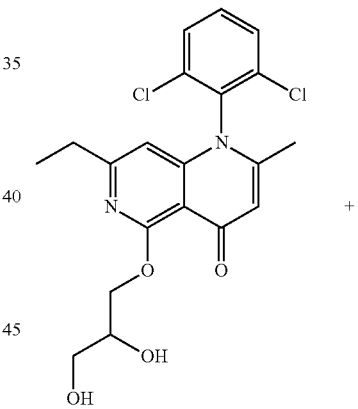

+

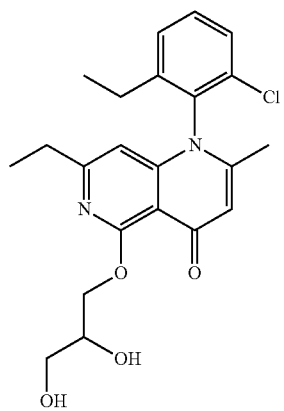

Step 1: 1-(2,6-Dichlorophenyl)-5-((2,2-dimethyl-1,3-dioxolan-4-yl)methoxy)-7-ethyl-2-methyl-1,6-naphthyridin-4(1H)-one and 1-(2-chloro-6-ethylphenyl)-5-((2,2-dimethyl-1,3-dioxolan-4-yl)methoxy)-7-ethyl-2-methyl-1,6-naphthyridin-4(1H)-one Diethyl zinc (3.55 ml, 3.55 mmol) solution (1M in heptane) was added to the mixture of 7-chloro-1-(2,6-dichlorophenyl)-5-((2,2-dimethyl-1,3-dioxolan-4-yl)methoxy)-2-methyl-1,6-naphthyridin-4(1H)-one (0.833 g, 1.774 mmol), DPPF (0.197 g, 0.355 mmol), and Pd(OAc)$_2$ (0.040 g 0.177 mmol) in toluene (10 ml) dropwise at −78° C. under nitrogen atmosphere. After addition, the reaction was heated at 90° C. for 1 hour. The reaction was cooled to rt and quenched with sat. aq.NH$_4$Cl, diluted with EtOAc and filtered through celite. The organic phase was washed with brine, dried over anhydrous MgSO$_4$ and concentrated in vacuo. The crude residue was purified by column chromatography eluting with 0-100% EtOAc/Heptane to afford 1-(2,6-dichlorophenyl)-5-(2,3-dihydroxypropoxy)-7-ethyl-2-methyl-1,6-naphthyridin-4(1H)-one (0.7 g yellow solid, 1.44 mmol) and 1-(2-chloro-6-ethylphenyl)-5-(2,3-dihydroxpropoxy)-7-ethyl-2-methyl-1,6-naphthyridin-4(1H)-one (0.012 g white solid, 0.025 mmol).

Step 2: 1-(2,6-Dichlorophenyl)-5-(2,3-dihydroxpropoxy)-7-ethyl-2-methyl-1,6-naphthyridin-4(1H)-one compound and 1-(2-chloro-6-ethylphenyl)-5-(2,3-dihydroxypropoxy)-7-ethyl-2-methyl-1,6-naphthyridin-4(1H)-one The two compounds from above were separately dissolved in a 1:1 mixture of DCM and TFA and stirred at rt for 1 hour. After removal of volatiles and purification by basic preparative HPLC, fractions containing examples 66 and 67 were obtained as white powders.

66: HRMS: calc. 423.0878 [M+F1]$^+$, found 423.0897; $^1$H NMR (400 MHz, chloroform-d3) δ ppm=7.67-7.46 (m, 3H), 6.34 (s, 1H), 5.74 (s, 1H), 4.84 (d, J=11.5 Hz, 1H), 4.38 (dd, J=11.4, 3.3 Hz, 1H), 4.07-3.94 (m, 2H), 3.87 (dd, J=11.7, 5.4 Hz, 1H), 2.56 (q, J=7.5 Hz, 2H), 1.95 (s, 3H), 1.16 (t, J=7.5 Hz, 3H).

67: HRMS: calc. 417.1581 [M+H]$^+$, found 417.1626; $^1$H NMR (400 MHz, chloroform-d3) δ ppm=7.59-7.32 (m, 3H), 6.37 (d, J=15.1 Hz, 1H), 5.83 (d, J=41.9 Hz, 1H), 4.97-4.74 (m, 1H), 4.37 (ddd, J=10.9, 7.1, 3.1 Hz, 1H), 4.11-3.69 (m, 3H), 2.56 (dq, J=15.1, 7.6 Hz, 2H), 2.29 (dddd, J=30.2, 22.7, 15.0, 7.3 Hz, 2H), 1.93 (d, J=9.4 Hz, 3H), 1.12 (dt, J=11.1, 7.6 Hz, 6H).

Example 68: 1-(2,6-Dichlorophenyl)-5-(2,3-dihydroxpropoxy)-7-methoxy-2-methyl-1,6-naphthyridin-4(1H)-one

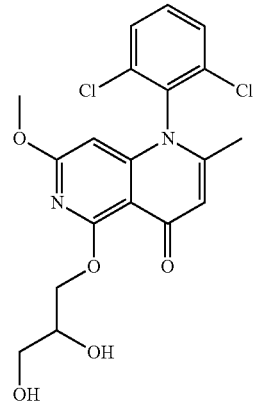 [SMILES: COc1cc2c(c(OCC(O)CO)n1)c(=O)cc(C)n2-c1c(Cl)cccc1Cl]

The mixture of 7-chloro-1-(2,6-dichlorophenyl)-5-((2,2-dimethyl-1,3-dioxolan-4-yl)methoxy)-2-methyl-1,6-naphthyridin-4(1H)-one (29 mg, 0.062 mmol), Na$_2$CO$_3$ (19.63 mg, 0.185 mmol), X-Phos (5.75 mg, 0.012 mmol) and Pd(OAc)$_2$ (1.386 mg, 6.17 μmol) in toluene (0.5 ml) and MeOH (0.050 ml, 1.235 mmol) was purged with nitrogen and heated at 80° C. overnight. After cooling, the mixture was concentrated, taken up into ethyl acetate and filtered through a silica gel plug. The solvent was removed and the crude residue was then dissolved in HOAc (1 ml). Water (1 ml) was added. The resulting solution was stirred at rt overnight. The reaction mixture was concentrated, neutralized with conc. ammonia and purified by basic preparative HPLC (Waters Xbridge 5 um 30×100 mm, water/acetonitrile with 10 mM NH$_4$OH 75 mL/min, 1.5 mL injection, 15-30% ACN at 11.5 min) to afford the title compound as off white powder (11.8 mg, 0.027 mmol) 68: HRMS: calc. 425.0671 [M+H]$^+$, found 425.0685; $^1$H NMR (400 MHz, chloroform-d3) δ ppm=7.64-7.43 (m, 3H), 6.27-6.18 (m, 1H), 5.28 (s, 1H), 4.84 (dd, J=11.2, 1.5 Hz, 1H), 4.35 (dd, J=11.2, 3.3 Hz, 1H), 4.10-3.96 (m, 3H), 3.96-3.82 (m, 5H), 1.93 (s, 3H).

Example 69: 1-(2,6-Dichlorophenyl)-5-(2,3-dihydroxpropoxy)-8-ethyl-2-methyl-1,6-naphthyridin-4(1H)-one

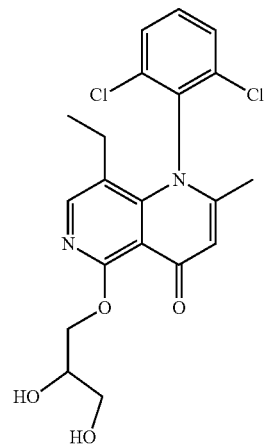 [SMILES: CCc1cnc(OCC(O)CO)c2c(=O)cc(C)n(-c3c(Cl)cccc3Cl)c12]

Example 69 was prepared in an analogous way to example 66 using intermediate 10 as a starting material to afford a white powder.

69: HRMS: calc. 423.0878 [M+H]⁺, found 423.0888; ¹H NMR (400 MHz, chloroform-d3) δ ppm=7.96 (s, 1H), 7.59-7.44 (m, 3H), 6.42 (s, 1H), 5.23 (s, 1H), 4.77 (d, J=10.8 Hz, 1H), 4.37 (dd, J=11.1, 3.4 Hz, 1H), 3.93 (dd, J=55.4, 11.9 Hz, 4H), 1.97-1.79 (m, 5H), 0.95 (t, J=7.4 Hz, 3H).

Example 70: N-(1-(2,6-Dichloro-4-cyanophenyl)-2-methyl-4-oxo-1,4-dihydro-1,7-naphthyridin-5-yl)-1H-pyrazole-4-sulfonamide

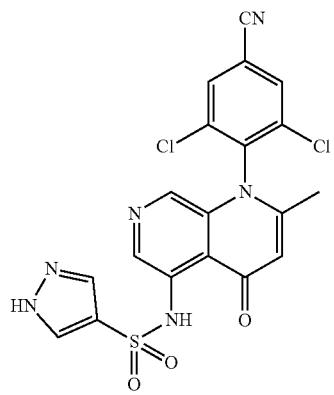 [SMILES: Cc1cc(=O)c2c(NS(=O)(=O)c3cn[nH]c3)cncc2n1-c1c(Cl)cc(C#N)cc1Cl]

Step 1: 4-(5-Amino-2-methyl-4-oxo-1,7-naphthyridin-1(4H)-yl)-3,5-dichlorobenzonitrile

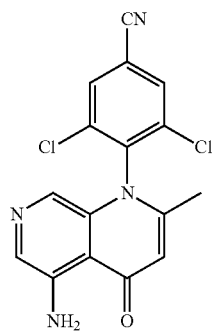 [SMILES: Cc1cc(=O)c2c(N)cncc2n1-c1c(Cl)cc(C#N)cc1Cl]

The mixture of intermediate 12 (0.028 g, 0.080 mmol), aq. concentrated ammonia (0.035 ml, 0.402 mmol) in THF (0.5 ml) was heated at 80° C. in a sealed tube for 1 hour. The reaction mixture was concentrated in vacuo and the residue was purified by basic preparative HPLC (Waters X-bridge 30×50 mm 5 um column, ACN/H₂O with 10 mM NH₄OH, 75 mL/min, 1.5 mL injection, gradient: 25-50% ACN in 4.5 min) to afford the title compound (0.015 g, 54% yield) as a white powder.

Step 2: N-(1-(2,6-Dichloro-4-cyanophenyl)-2-methyl-4-oxo-1,4-dihydro-1,7-naphthyridin-5-yl)-1H-pyrazole-4-sulfonamide The mixture of 4-(5-Amino-2-methyl-4-oxo-1,7-naphthyridin-1(4H)-yl)-3,5-dichlorobenzonitrile (0.015 g, 0.043 mmol) and 1H-pyrazole-4-sulfonyl chloride (0.015 g, 0.087 mmol) in pyridine (0.5 ml) was stirred at 80° C. overnight. The reaction was concentrated in vacuo. The residue was purified by basic preparative HPLC (Waters X-bridge 30×50 mm 5 um column, ACN/H2O with 10 mM NH4OH, 75 mL/min, 1.5 mL injection, gradient: 25-50% ACN in 4.5 min) to afford the title compound (4.8 mg) as an off-white powder.

70: HRMS: calc. 475.0147 [M+H]⁺, found 475.0142; ¹H NMR (400 MHz, chloroform-d3) δ ppm=13.01 (s, 1H), 8.78 (s, 1H), 8.05 (s, 2H), 7.94 (s, 2H), 7.58 (s, 1H), 6.40 (s, 1H), 2.05 (s, 3H).

Example 71: 8-Chloro-1-(2,6-dichlorophenyl)-2-methyl-5-(1H-1,2,4-triazol-1-yl)-1,6-naphthyridin-4(1H)-one

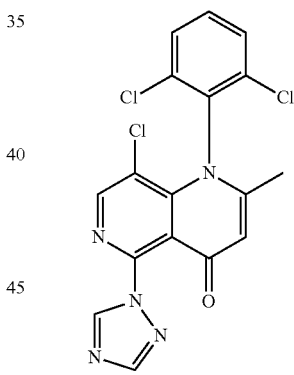

The mixture of intermediate 1 (20 mg, 0.053 mmol) and sodium 1,2,4-triazol-1-ide (7.30 mg, 0.080 mmol) in THF (1 ml) was heated at 70° C. for 2 hours. The reaction mixture was concentrated. The crude residue was purified by basic preparative HPLC (Waters X-bridge 30×50 mm 5 um column, ACN/H2O with 10 mM NH4OH, 75 mL/min, 1.5 mL injection, gradient: 25-50% ACN in 4.5 min) to afford the title compound as off white powder (17 mg).

71: HRMS: calc. 406.0029 [M+H]⁺, found 406.0036; ¹H NMR (400 MHz, chloroform-d3) δ ppm=8.54 (s, 1H), 8.49 (s, 1H), 8.16 (s, 1H), 7.53 (d, J=2.4 Hz, 3H), 6.43 (s, 1H), 1.99 (s, 3H).

The compounds below were prepared as described in Scheme C

Example 72: 3,5-dichloro-4-(2-methyl-4-oxo-5-(1H-pyrazol-3-yl)-1,7-naphthyridin-1(4H)-yl)benzonitrile

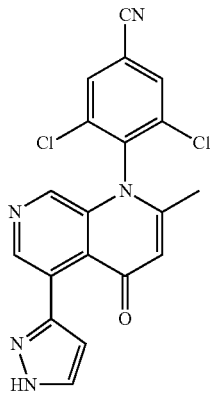 [SMILES: Cc1cc(=O)c2c(-c3cc[nH]n3)cncc2n1-c1c(Cl)cc(C#N)cc1Cl]

A mixture of 4-(5-bromo-2-methyl-4-oxo-1,7-naphthyridin-1(4H)-yl)-3,5-dichlorobenzonitrile (intermediate 13, 0.040 g, 0.098 mmol), (1H-pyrazol-3-yl)boronic acid (0.044 g, 0.391 mmol), Pd(PPh$_3$)$_4$ (0.011 g, 9.78 umol) and Cs$_2$CO$_3$ (0.096 g, 0.293 mmol) in dioxane (2 mL) was stirred in microwave at 140° C. for 10 h. The solid was filtered off. Volatiles were removed under reduced pressure and the residue was purified with silica-gel chromatography (0-5% MeOH/DCM) to afford crude product which was further purified with reverse phase HPLC (X-bridge 30×50 mm 5 um column, ACN/H$_2$O with 5 mM NH$_4$OH, 75 mL/min, 1.5 mL injection, gradient: 15-40% ACN in 3.5 min) to afford white powder as the title compound (10 mg, 25% yield). 72: HRMS: calc. 396.0419 [M+H]$^+$, found 396.0422; $^1$H NMR (400 MHz, DMSO-d6) δ ppm=12.77 (bs, 1H), 8.60 (s, 2H), 8.47 (s, 1H), 8.25 (s, 1H), 7.65 (bs., 1H), 6.45 (d, J=2.02 Hz, 1H), 6.40 (s, 1H), 2.01 (s, 3H).

The following compound was prepared using analogous methods as the above compound.

Example 73: 3,5-Dichloro-4-(2-methyl-5-(1-methyl-1H-pyrazol-4-yl)-4-oxo-1,7-naphthyridin-1(4H)-yl)benzonitrile

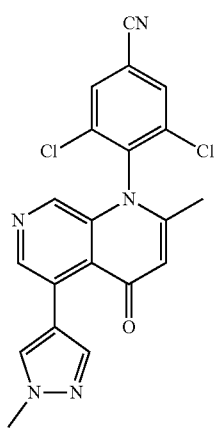

73: HRMS: calc. 410.0575 [M+H]$^+$, found 410.0564. $^1$H NMR (400 MHz, DMSO-d6) δ ppm=8.59 (s, 2H), 8.41 (s, 1H), 8.10 (s, 1H), 7.99 (s, 1H), 7.65 (s, 1H), 6.38 (s, 1H), 3.89 (s, 3H), 2.00 (s, 3H).

Example 74: 8-Chloro-1-(2,6-dichlorophenyl)-2-(hydroxymethyl)-5-(3-hydroxypropyl)-1,6-naphthyridin-4(1H)-one

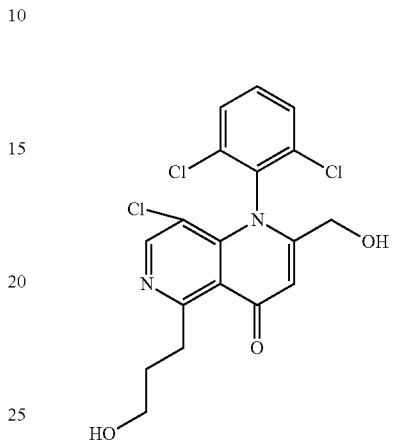

Step 1: 5-(2-(1,3-Dioxan-2-yl)ethyl)-2-(((tert-butyldimethylsilyl)oxy)methyl)-8-chloro-1-(2,6-dichlorophenyl)-1,6-naphthyridin-4(1H)-one

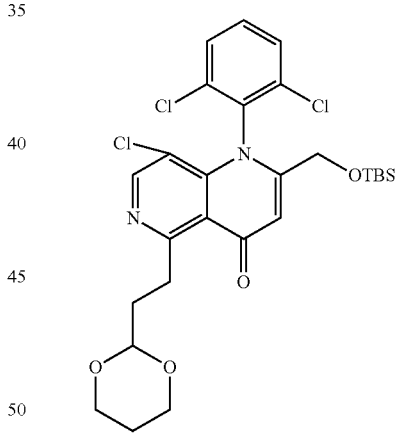

To a solution of 2-(((tert-butyldimethylsilyl)oxy)methyl)-5,8-dichloro-1-(2,6-dichlorophenyl)-1,6-naphthyridin-4(1H)-one (intermediate 7, 0.2 g, 0.397 mmol) in THF (4 mL) was added (2-(1,3-dioxan-2-yl)ethyl)magnesium bromide (0.5 M in THF, 1.03 mL, 0.516 mmol). The mixture was stirred at room temperature for 1 h followed by adding another batch of (2-(1,3-dioxan-2-yl)ethyl)magnesium bromide (0.5 M in THF, 1.0 mL, 0.50 mmol). The reaction mixture was stirred at room temperature for another 1 h. Water was then added to quench the reaction mixture. THF was removed under reduced pressure and the residue was purified with silica-gel chromatography (10-40% EtOAc/heptane) to afford the title compound (0.083 g, 36% yield). ESI-MS m/z: 585.2 [M+H]$^+$ (Rt=1.84 min, LC-method 3)

Step 2: 3-(8-Chloro-1-(2,6-dichlorophenyl)-2-(hydroxymethyl)-4-oxo-1,4-dihydro-1,6-naphthyridin-5-yl)propanal

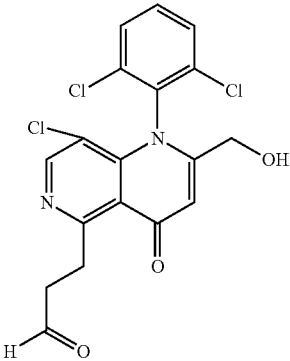 [SMILES: O=CCCc1ncc(Cl)c2c1c(=O)cc(CO)n2-c1c(Cl)cccc1Cl]

A mixture of 5-(2-(1,3-dioxan-2-yl)ethyl)-2-(((tert-butyldimethylsilyl)oxy)methyl)-8-chloro-1-(2,6-dichlorophenyl)-1,6-naphthyridin-4(1H)-one (0.044 g, 0.075 mmol) and aq. HCl (1 N, 0.678 mL, 0.678 mmol) in THF (1 mL) was stirred at 60° C. for 3 h. The reaction mixture was then quenched with aq. sat. NaHCO$_3$ until no more bubbles (CO$_2$) was generated. This reaction mixture was used directly in the next step. LC-MS indicate the title compound is the only product in this step. ESI-MS m/z: 412.8 [M+H]$^+$ (Rt=1.12 min, LC-method 3)

Step 3: 8-Chloro-1-(2,6-dichlorophenyl)-2-(hydroxymethyl)-5-(3-hydroxypropyl)-1,6-naphthyridin-4(1H)-one

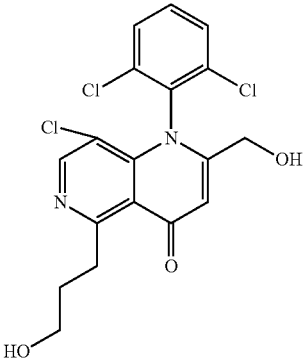 [SMILES: O=c1cc(CO)n(-c2c(Cl)cccc2Cl)c2c(Cl)cnc(CCCO)c12]

To the reaction mixture from step 2 was added EtOH (1 mL) and then NaBH$_4$ (0.023 g, 0.60 mmol). The resulted mixture was stirred at room temperature for 20 min. The solid was filtered out. THF was removed under reduced pressure and the residue was purified with reverse phase HPLC (Waters X-bridge 30×50 mm 5 um column, ACN/H$_2$O with 10 mM NH$_4$OH, 75 mL/min, 1.5 mL injection, gradient: 35-60% ACN in 4.5 min) to afford white solid as the title compound (25 mg, 0.025 g, 77% total yield for steps 2 and 3). 74: HRMS: calc. 413.0227 [M+H]$^+$, found 413.0213; $^1$H NMR (400 MHz, DMSO-d6) δ ppm=8.53 (s, 1H), 7.79-7.66 (m, 3H), 6.63 (s, 1H), 5.88 (s, 1H), 4.44 (t, J=4.9 Hz, 1H), 3.85-3.78 (m, 2H), 3.54-3.46 (m, 2H), 3.46-3.37 (m, 2H), 1.83 (dq, J=9.7, 6.7 Hz, 2H)

Example 75: 8-Chloro-1-(2,6-dichlorophenyl)-5-(3,4-dihydroxybutyl)-2-(hydroxymethyl)-1,6-naphthyridin-4(1H)-one

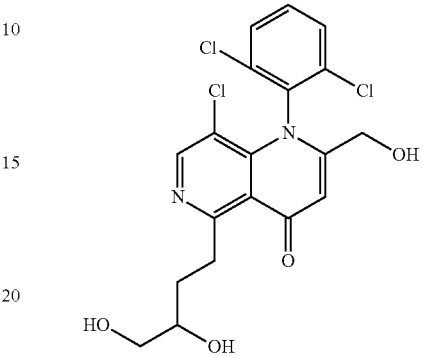

Step 1: 5-(But-3-en-1-yl)-2-(((tert-butyldimethylsilyl)oxy)methyl)-8-chloro-1-(2,6-dichlorophenyl)-1,6-naphthyridin-4(1H)-one

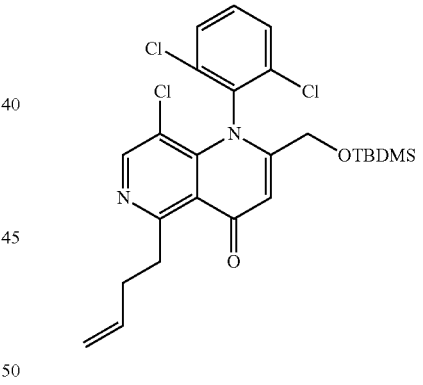

To a solution of 2-(((tert-butyldimethylsilyl)oxy)methyl)-5,8-dichloro-1-(2,6-dichlorophenyl)-1,6-naphthyridin-4 (1H)-one in (0.3 g, 0.595 mmol) THF (6 mL) was added but-3-en-1-ylmagnesium bromide (0.5 M in THF, 1.78 ml, 0.892 mmol). The resulting solution was stirred at room temperature for 3 hours. Reaction mixture was quenched with couple drops of water and concentrated under reduced pressure. The residue was purified by silica gel chromatography (0-50% EtOAc in heptane) to give the title compound (0.151 g, 48% yield). ESI-MS m/z: 525.1 [M+H]$^+$ (Rt=1.99 min, LC-method 1), $^1$H NMR (400 MHz, DCM-d2) δ ppm=8.38 (s, 1H), 7.47 (s, 3H), 6.68 (t, J=1.1 Hz, 1H), 6.04-5.87 (m, 1H), 5.14-4.87 (m, 2H), 4.00 (d, J=1.2 Hz, 2H), 3.54 (dd, J=8.5, 7.0 Hz, 2H), 2.54-2.40 (m, 2H), 0.86 (s, 9H), 0.0 (s, 6H).

Step 2: 2-(((tert-Butyldimethylsilyl)oxy)methyl)-8-chloro-1-(2,6-dichlorophenyl)-5-(3,4-dihydroxybutyl)-1,6-naphthyridin-4(1H)-one

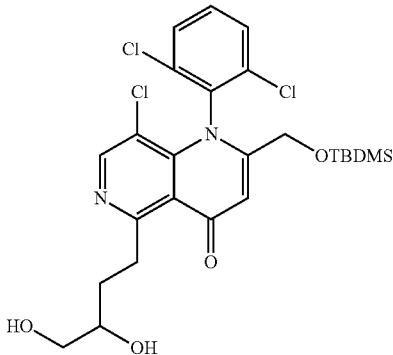 [SMILES: CC(C)(C)[Si](C)(C)OCc1cc(=O)c2c(CCC(O)CO)ncc(Cl)c2n1-c1c(Cl)cccc1Cl]

Osmium tetroxide (2.5 wt % solution in tert-butanol, 0.133 ml, 10.59 mmol) was added to a solution of 5-(but-3-en-1-yl)-2-(((tert-butyldimethylsilyl)oxy)methyl)-8-chloro-1-(2,6-dichlorophenyl)-1,6-naphthyridin-4(1H)-one (0.111 g, 0.212 mmol) and N-methylmorpholine N-oxide (0.027 g, 0.233 mmol) in the mixture of tert-butanol/water (2 ml/2 ml). The resulting mixture was stirred at room temperature for 4 hours. The product was separated between EtOAc and brine and combined organic extracts were dried over anhydrous $Na_2SO_4$, filtered and concentrated under reduced pressure. The residue was purified by silica gel chromatography (0-100% EtOAc in heptane) to give the title compound (0.077 g, 65% yield). ESI-MS m/z: 558.9 $[M+H]^+$ (Rt=1.55 min, LC-method 1), $^1$H NMR (400 MHz, DCM-d2) δ ppm=8.40 (s, 1H), 7.52-7.45 (m, 3H), 6.74 (t, J=1.1 Hz, 1H), 4.04-3.95 (m, 2H), 3.68-3.43 (m, 5H), 1.97-1.75 (m, 2H), 0.85 (s, 9H), 0.0 (s, 6H).

Step 3: 8-Chloro-1-(2,6-dichlorophenyl)-5-(3,4-dihydroxybutyl)-2-(hydroxymethyl)-1,6-naphthyridin-4(1H)-one 2-(((tert-butyldimethylsilyl)oxy)methyl)-8-chloro-1-(2,6-dichlorophenyl)-5-(3,4-dihydroxybutyl)-1,6-naphthyridin-4(1H)-one (0.077 g, 0.138 mmol) in THF (2 ml) was added a 1 M solution of TBAF in THF (0.207 ml, 0.207 mmol) at 0° C. The reaction was stirred at 0° C. for 1 hour. It was quenched with water and diluted in EtOAc. The aqueous layer was extracted with EtOAc. The combined organic layer was washed with brine, dried over anhydrous $Na_2SO_4$, filtered, and concentrated under reduced pressure. The residue was purified by silica gel chromatography (0-5% MeOH in DCM) to give the title compound (0.031 g, 46% yield).

75: ESI-MS m/z: 443.2 $[M+H]^+$ (Rt=0.75, LC-method 1), $^1$H NMR (400 MHz, DCM-d2) δ ppm=8.47 (s, 1H), 7.55 (d, J=1.9 Hz, 3H), 6.87 (t, J=1.1 Hz, 1H), 4.11 (s, 2H), 3.78-3.45 (m, 5H), 2.08-1.84 (m, 2H).

Chiral Separation of the Above Racemate

Examples 76 and 77: One of Examples 76 and 77 is (R)-8-Chloro-1-(2,6-dichlorophenyl)-5-(3,4-dihydroxybutyl)-2-(hydroxymethyl)-1,6-naphthyridin-4(1H)-one and the other is (S)-8-Chloro-1-(2,6-dichlorophenyl)-5-(3,4-dihydroxybutyl)-2-(hydroxymethyl)-1,6-naphthyridin-4(1H)-one 218 mg of 8-chloro-1-(2,6-dichlorophenyl)-5-(3,4-dihydroxybutyl)-2-(hydroxymethyl)-1,6-naphthyridin-4(1H)-one (example 75) was dissolved in 20 ml methanol and submitted in multiple injections of 1.6 ml each to chiral preparative SFC (ChiralPak AD column, 250×330 mm ID, 5 µm, flow rate of 50 ml/min at 38° C.) using 40% ethanol in carbon dioxide with 0.1% aq. ammonia as mobile phase. After chiral separation, the fractions were dried off via rotary evaporation at a bath temperature of 40° C. to give example 76 as the first eluting peak (82 mg, 100% ee) and example 77 as the second eluting peak (40 mg, 98.8% ee) as white solids. Retention times were obtained on a ChiralPak IA column, 4.6×100 mm, 5 µm column. A gradient of 5-55% 1:1 MeOH/2-propanol in carbon dioxide with 10 mM $NH_4OH$ as mobile phase was applied over 5.5 min, then held for 0.1 min (5.0 ml/min as solvent flow) at an oven temperature of 38° C. (Example 76: Rt=3.63 min; Example 77: Rt=4.24 min)

Example 78: 8-Chloro-1-(2,6-dichlorophenyl)-5-(2,3-dihydroxypropyl)-2-(hydroxymethyl)-1,6-naphthyridin-4(1H)-one

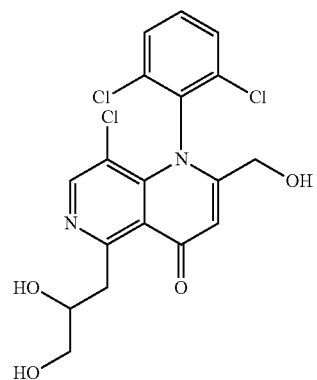 [SMILES: O=c1cc(CO)n(-c2c(Cl)cccc2Cl)c2c(Cl)cnc(CC(O)CO)c12]

Step 1: 5-Allyl-2-(((tert-butyldimethylsilyl)oxy)methyl)-8-chloro-1-(2,6-dichlorophenyl)-1,6-naphthyridin-4(1H)-one

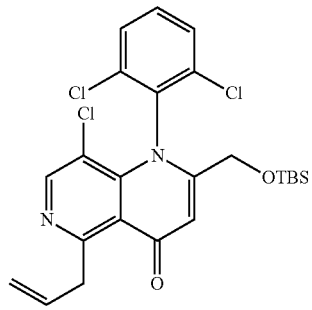 [SMILES: C=CCc1ncc(Cl)c2c1c(=O)cc(CO[Si](C)(C)C(C)(C)C)n2-c1c(Cl)cccc1Cl]

To a solution of intermediate 7 (0.65 g, 1.289 mmol) in toluene (10 ml) was added allyltri-n-butyltin (0.799 ml, 2.58 mmol) and $PdCl_2(dppf)*CH_2Cl_2$ adduct (0.105 g, 0.129 mmol) at room temperature under nitrogen atmosphere. The resulting solution was purged with nitrogen and heated at 80° C. for one hour. Purification by column chromatography (solid loading, 0-30% ethyl acetate in heptane) provided 5-allyl-2-(((tert-butyldimethylsilyl)oxy)methyl)-8-chloro-1-

(2,6-dichlorophenyl)-1,6-naphthyridin-4(1H)-one (0.6 g 1.18 mmol) as a pale yellow oil. ESI-MS m/z: 511.0 [M+H]+

Step 2: 2-(((tert-Butyldimethylsilyl)oxy)methyl)-8-chloro-1-(2,6-dichlorophenyl)-5-(2,3-dihydroxypropyl)-1,6-naphthyridin-4(1H)-one

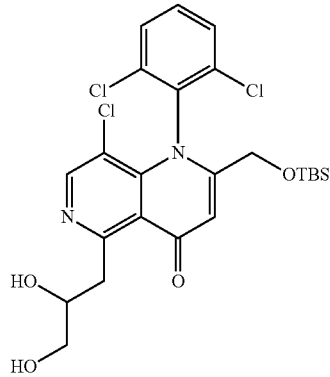 [SMILES: CC(C)(C)[Si](C)(C)OCc1cc(=O)c2c(CC(O)CO)ncc(Cl)c2n1-c1c(Cl)cccc1Cl]

To a solution of 5-Allyl-2-(((tert-butyldimethylsilyl)oxy)methyl)-8-chloro-1-(2,6-dichlorophenyl)-1,6-naphthyridin-4(1H)-one (0.6 g, 1.177 mmol) in 1,4-dioxane (8 ml) and water (1.6 ml) was treated with osmium tetroxide (2.991 g, 0.235 mmol) and NMO (0.414 g, 3.53 mmol). The reaction was stirred at room temperature for 2 hours. A solution of saturated sodium metabisulphite was added and the mixture was stirred for another 30 minutes. Water was added and the mixture was extracted with ethyl acetate. The combined organic extracts were dried (Na₂SO₄), filtered and concentrated in vacuo. Purification by column chromatography (0-100% ethyl acetate in heptane) provided 2-(((tert-butyldimethylsilyl)oxy)methyl)-8-chloro-1-(2,6-dichlorophenyl)-5-(2,3-dihydroxypropyl)-1,6-naphthyridin-4(1H)-one (0.5 g, 0.92 mmol) as white foam solid. ESI-MS m/z: 544.8 [M+H]+

Step 3: 8-Chloro-1-(2,6-dichlorophenyl)-5-(2,3-dihydroxypropyl)-2-(hydroxymethyl)-1,6-naphthyridin-4(1H)-one

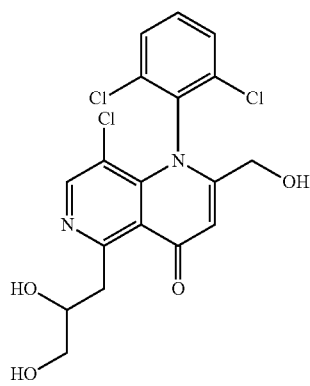 [SMILES: O=c1cc(CO)n(-c2c(Cl)cccc2Cl)c2c(Cl)cnc(CC(O)CO)c12]

To a solution of the above compound (0.5 g, 0.919 mmol) in acetic acid (5 ml) was added water (5 ml) at room temperature. The resulting solution was stirred at room temperature overnight. The reaction was concentrated, neutralized with conc. NH₃, and purified by basic preparative RP-HPLC (Waters X-bridge 30×50 mm 5 um column, ACN/H₂O with 10 mM NH₄OH, 75 mL/min, 1.5 mL injection, gradient: 25-50% ACN in 4.5 min) to afford the title compound (0.3 g, 0.66 mmol) as white powder.

78: HRMS: calc. 429.0176 [M+H]+, found 429.0169, ¹H NMR (400 MHz, chloroform-d3) δ ppm=8.45 (s, 1H), 7.49 (s, 3H), 6.94 (s, 1H), 4.92 (s, 1H), 4.26 (s, 1H), 4.05 (s, 2H), 3.66 (qd, J=15.8, 14.3, 6.0 Hz, 5H), 2.91 (s, 1H).

Chiral Separation of the Above Racemate

Examples 79 and 80: One of examples 79 and 80 is (R)-8-Chloro-1-(2,6-dichlorophenyl)-5-(2,3-dihydroxypropyl)-2-(hydroxymethyl)-1,6-naphthyridin-4(1H)-one and the other is (S)-8-Chloro-1-(2,6-dichlorophenyl)-5-(2,3-dihydroxpropyl)-2-(hydroxymethyl)-1,6-naphthyridin-4(1H)-one The racemate 78 was submitted in multiple injections of 1.6 ml each to chiral preparative SFC (Cellulose-2 column, 250×330 mm I.D., 5 µm, flow rate of 50 ml/min at 38° C.) using 40% ethanol in carbon dioxide with 0.1% aq. ammonia as mobile phase. After chiral separation, the fractions were dried off via rotary evaporation at a bath temperature of 40° C. to give example 79 as the first eluting peak (>98% ee) and example 80 as the second eluting peak (>98% ee) as white solids. Retention times were obtained on a Cellulose-2 column, 4.6×150 mm, 5 µm column. A mobile phase of 40% MeOH (with 0.05% DEA) in carbon dioxide was applied (2.4 ml/min as solvent flow) at an oven temperature of 35° C. (Example 79: Rt=6.93 min; Example 80: Rt=7.68 min)

79: HRMS: calc. 429.0176 [M+H]+, found 429.0171; 1H NMR (400 MHz, chloroform-d3) δ ppm=8.46 (s, 1H), 7.49 (d, J=4.8 Hz, 3H), 6.94 (s, 1H), 4.15 (m, 4H), 3.84-3.56 (m, 6H).

80: HRMS: calc. 429.0176 [M+H]+, found 429.0169; ¹H NMR (400 MHz, chloroform-d3) δ ppm=8.45 (s, 1H), 7.49 (d, J=4.6 Hz, 3H), 6.94 (s, 1H), 4.92 (s, 1H), 4.26 (s, 1H), 4.05 (s, 2H), 3.66 (qd, J=15.8, 14.3, 6.0 Hz, 5H), 2.91 (s, 1H).

The following compound was prepared using analogous methods to the above compound from intermediate 1.

Example 81: 8-Chloro-1-(2,6-dichlorophenyl)-5-(2,3-dihydroxpropyl)-2-methyl-1,6-naphthyridin-4(1H)-one

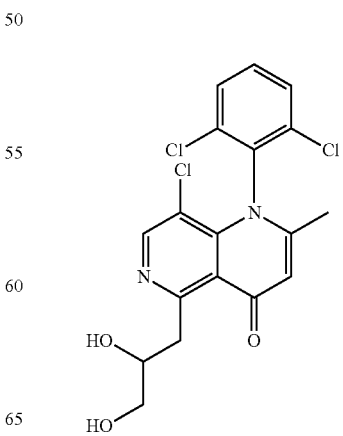

81: HRMS: calc. 413.0227 [M+H]+, found 413.0230; 1H NMR (400 MHz, chloroform-d3) δ ppm=8.45 (s, 1H), 7.49 (s, 3H), 4.98-4.81 (m, 1H), 4.27 (s, 1H), 3.82-3.53 (m, 4H), 2.96 (s, 1H), 1.98 (s, 3H).

Example 82: 8-Chloro-1-(2,6-dichlorophenyl)-5-(1,2-dihydroxyethyl)-2-(hydroxymethyl)-1,6-naphthyridin-4(1H)-one

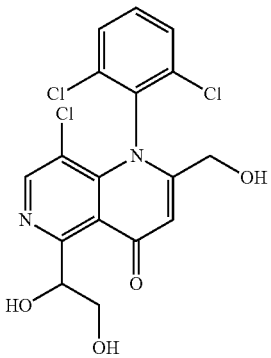 [SMILES: O=c1cc(CO)n(-c2c(Cl)cccc2Cl)c2c(Cl)cnc(C(O)CO)c12]

Step 1: 2-(((tert-Butyldimethylsilyl)oxy)methyl)-8-chloro-1-(2,6-dichlorophenyl)-5-vinyl-1,6-naphthyridin-4(1H)-one

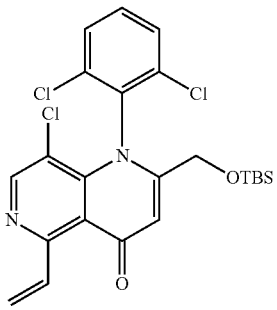 [SMILES: C=Cc1ncc(Cl)c2c1c(=O)cc(CO[Si](C)(C)C(C)(C)C)n2-c1c(Cl)cccc1Cl]

To a solution of intermediate 7 (0.47 g, 0.932 mmol) in acetonitrile (5 ml) and water (1 ml) was added vinylboronic anhydride pyridine complex (0.317 g, 1.864 mmol), Na2CO3 (0.198 g, 1.864 mmol), and PdCl2(dppf)*CH2Cl2 adduct (0.076 g, 0.093 mmol) at room temperature under nitrogen atmosphere. The resulting reaction mixture was purged with nitrogen and heated at 80° C. in the seal tube for one hour. Purification by column chromatography (solid loading, 0-40% ethyl acetate in heptane) provided 2-(((tert-butyldimethylsilyl)oxy)methyl)-8-chloro-1-(2,6-dichlorophenyl)-5-vinyl-1,6-naphthyridin-4(1H)-one (0.4 g, 0.81 mmol) as pale yellow oil. ESI-MS m/z: 497.0.0 [M+H]+)

Step 2 and 3 were done in the same way as described for the previous example to yield 8-chloro-1-(2,6-dichlorophenyl)-5-(1,2-dihydroxyethyl)-2-(hydroxymethyl)-1,6-naphthyridin-4(1H)-one as a white solid.

82: HRMS: calc. 415.0019 [M+H]+, found 415.0016; 1H NMR (400 MHz, chloroform-d3) δ ppm=8.50 (s, 1H), 7.50 (s, 3H), 6.93 (s, 1H), 5.80 (d, J=4.3 Hz, 1H), 5.30 (d, J=6.0 Hz, 1H), 4.17-3.82 (m, 5H), 3.40 (s, 1H), 2.97 (s, 1H).

Chiral Separation of the Racemate

Examples 83 and 84: One of Examples 83 and 84 is (R)-8-Chloro-1-(2,6-dichlorophenyl)-5-(1,2-dihydroxyethyl)-2-(hydroxymethyl)-1,6-naphthyridin-4(1H)-one and the other is (S)-8-Chloro-1-(2,6-dichlorophenyl)-5-(1,2-dihydroxyethyl)-2-(hydroxymethyl)-1,6-naphthyridin-4(1H)-one The racemate 82 was dissolved in methanol and submitted in multiple injections of 1.6 ml each to chiral preparative SFC (Cellulose-2 column, 250×330 mm I.D., 5 µm, flow rate of 50 ml/min at 38° C.) using 40% ethanol in carbon dioxide with 0.1% aq. ammonia as mobile phase. After chiral separation, the fractions were dried off via rotary evaporation at a bath temperature of 40° C. to give example 83 as the first eluting peak (>98% ee) and example 84 as the second eluting peak (>98% ee) as white solids. Retention times were obtained on a ChiralPak AY column, 4.6×150 mm, 3 µm column. A mobile phase of 50% 2-propanol (with 0.05% DEA) in carbon dioxide was applied (2 ml/min as solvent flow) at an oven temperature of 35° C. (Example 83: Rt=3.13 min; Example 84: Rt=4.32 min)

Example 85: 8-Chloro-1-(2,6-dichlorophenyl)-5-(1,2-dihydroxyethyl)-2-methyl-1,6-naphthyridin-4(1H)-one

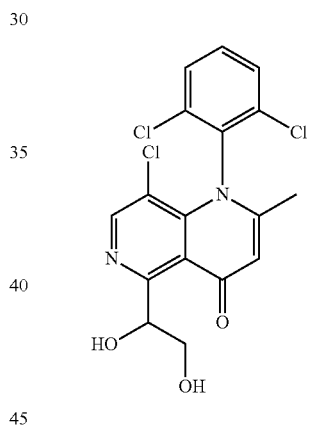

Step 1: 8-Chloro-1-(2,6-dichlorophenyl)-2-methyl-5-vinyl-1,6-naphthyridin-4(1H)-one

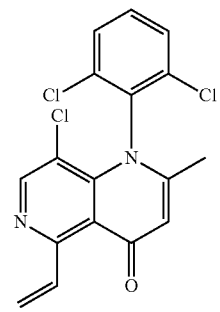 [SMILES: C=Cc1ncc(Cl)c2c1c(=O)cc(C)n2-c1c(Cl)cccc1Cl]

To a solution of intermediate 1 (1 g, 2.67 mmol) in acetonitrile (10 ml) was added vinylboronic anhydride pyridine complex (0.772 g, 3.21 mmol), 2.0 M aq.K3PO4 (2.67 ml, 5.35 mmol) solution. The reaction was degassed and put under nitrogen before PdCl$_2$(dppf).CH$_2$Cl$_2$ adduct (0.218 g, 0.267 mmol) was added. The mixture was purged with nitrogen again, heated at reflux at 80° C. in oil bath for 1.5 hours. The mixture was cooled to rt, solvent was removed. The residue was taken up into EtOAC. The organic phase was washed with brine, dried over anhydrous MgSO$_4$, filtered and concentrated in vacuo. The crude residue was purified by column chromatography eluting with 0-50% EtOAC/Heptane to provide 8-chloro-1-(2,6-dichlorophenyl)-2-methyl-5-vinyl-1,6-naphthyridin-4(1H)-one (0.85 g, 8.32 mmol) as yellow solid.

Step 2: 8-Chloro-1-(2,6-dichlorophenyl)-5-(1,2-dihydroxyethyl)-2-methyl-1,6-naphthyridin-4(1H)-one A solution of the product of step 1 (0.8 g, 2.188 mmol) in acetone (10 mL) and water (2 mL) was treated with NMO (0.769 g, 6.56 mmol) and osmium tetroxide (0.278 g, 0.044 mmol) at rt. The reaction was stirred under nitrogen at room temperature for 16 h to give two products. After this time, a solution of saturated Na$_2$S$_2$O$_3$ was added and stirring continued for 30 minutes. Water was added and the mixture was extracted with ethyl acetate (2×). The combined organic extracts were washed with brine, dried (Na$_2$SO$_4$), filtered and concentrated in vacuo. The crude residue was purified by column chromatography eluting with 0-100% EtOAC/heptane to provide two product the title compound (0.6 g, 1.43 mmol) and 8-chloro-1-(2,6-dichlorophenyl)-5-(2-hydroxyacetyl)-2-methyl-1,6-naphthyridin-4(1H)-on (0.05 g, 0.13 mmol).

85: HRMS: calc. 399.0070 [M+H]$^+$, found 399.0089; $^1$H NMR (400 MHz, chloroform-d3) δ ppm=8.50 (s, 1H), 7.50 (m, 3H), 6.60-6.40 (s, 1H), 5.82 (t, J=5.2 Hz, 1H), 4.14-3.92 (m, 2H), 2.01-1.91 (s, 3H).

Example 86: 8-Chloro-1-(2,6-dichlorophenyl)-5-(2-hydroxyacetyl)-2-methyl-1,6-naphthyridin-4(1H)-one

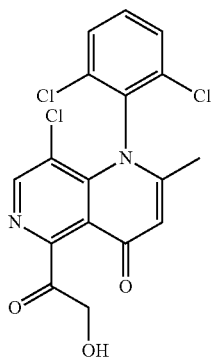 [SMILES: Cc1cc(=O)c2c(C(=O)CO)ncc(Cl)c2n1-c1c(Cl)cccc1Cl]

This compound was formed as a side product during the synthesis of example 85 described above.

86: HRMS: calc. 396.9915 [M+H]$^+$, found 396.9914; $^1$H NMR (400 MHz, chloroform-d3) δ ppm=8.58 (s, 1H), 7.53 (s, 3H), 6.49 (s, 1H), 4.68 (s, 2H), 2.04 (s, 3H).

Example 87: 8-Chloro-1-(2,6-dichlorophenyl)-5-((2,3-dihydroxypropoxy)methyl)-2-(hydroxymethyl)-1,6-naphthyridin-4(1H)-one

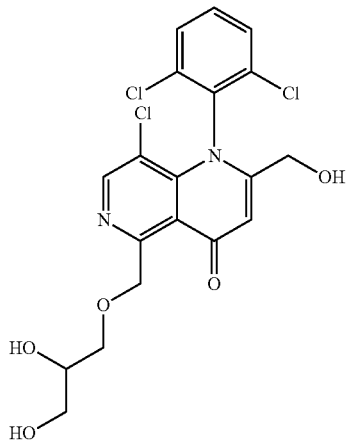 [SMILES: O=c1cc(CO)n(-c2c(Cl)cccc2Cl)c2c(Cl)cnc(COCC(O)CO)c12]

Preparation of the stannane required in step 1: tributyl(((2,2-dimethyl-1,3-dioxolan-4-yl)methoxy)methyl)stannane

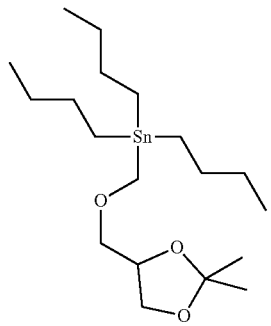 [SMILES: CCC[CH2][Sn]([CH2]CCC)([CH2]CCC)[CH2]OCC1COC(C)(C)O1]

To a solution of (2,2-dimethyl-1,3-dioxolan-4-yl)methanol (0.207 g, 1.566 mmol) in THF (2 ml) and DMSO (2 ml) was added NaH (0.046 g, 1.149 mmol) at 0° C. under nitrogen atmosphere. The resulting solution was stirred at room temperature for 30 min, and tributyl(iodomethyl)stannane (0.45 g, 1.044 mmol) was added. The resulting solution was stirred at rt overnight. The mixture was concentrated, taken up into heptane/EtOAC (7:1). The organic phase was washed with brine, dried over anhydrous MgSO$_4$, filtered and concentrated in vacuo. The crude residue (colorless oil) was used for the next step without further purification.

The Stille coupling between the above stannane and intermediate 7 and subsequent deprotection steps were performed in an analogous manner as for example 78 to yield the title compound.

87: HRMS: calc. 459.0281 [M+H]$^+$, found 459.0277; $^1$H NMR (400 MHz, chloroform-d3) δ ppm=8.48 (s, 1H), 7.60-7.40 (m, 3H), 6.93 (s, 1H), 5.37-5.18 (m, 2H), 4.80 (s, 1H), 4.42 (s, 1H), 4.04 (d, J=5.5 Hz, 2H), 3.93 (s, 1H), 3.77 (ddd, J=38.5, 9.8, 4.8 Hz, 4H), 3.54 (s, 1H).

Example 88: 8-Chloro-1-(2,6-dichlorophenyl)-5-(((1,3-dihydroxypropan-2-yl)oxy)methyl)-2-(hydroxymethyl)-1,6-naphthyridin-4(1H)-one

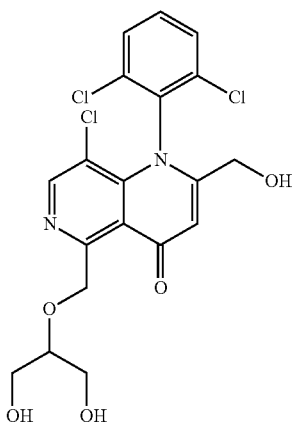 [SMILES: O=c1cc(CO)n(-c2c(Cl)cccc2Cl)c2c(Cl)cnc(COC(CO)CO)c12]

This compound was prepared analogous to the above example using 2,2-dimethyl-1,3-dioxan-5-ol in the preparation of the required stannane.

88: HRMS: calc. 459.0281 M+H]+, found 459.0280; $^1$H NMR (400 MHz, chloroform-d3) δ ppm=8.47 (s, 1H), 7.48 (d, J=1.3 Hz, 3H), 6.92 (s, 1H), 5.42 (s, 2H), 4.04 (s, 2H), 3.81-3.57 (m, 5H).

Example 89: 8-Chloro-1-(2,6-dichlorophenyl)-5-(2,4-dihydroxy-3-oxobutan-2-yl)-2-methyl-1,6-naphthyridin-4(1H)-one

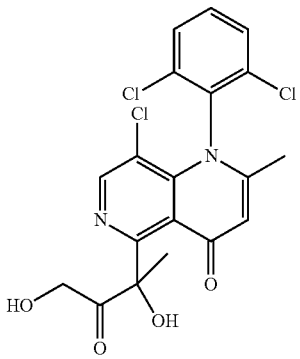 [SMILES: Cc1cc(=O)c2c(C(C)(O)C(=O)CO)ncc(Cl)c2n1-c1c(Cl)cccc1Cl]

Step 1: 5-Acetyl-8-chloro-1-(2,6-dichlorophenyl)-2-methyl-1,6-naphthyridin-4(1H)-one

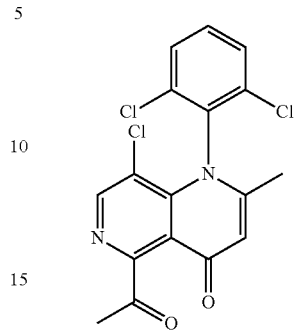

The mixture of intermediate 1 (0.5 g, 1.337 mmol), tributyl(1-ethoxyvinyl)tin (0.628 g, 1.738 mmol) and PdCl$_2$ (dppf).CH$_2$Cl$_2$ adduct (0.109 g, 0.134 mmol) in toluene (2 ml) was purged with nitrogen and heated at 80° C. overnight. After cooled to rt, the mixture was concentrated under reduced pressure. The residue was taken into EtOAc and filtered through a silica gel plug. The solvent was removed and the crude ethoxyvinyl intermediate (500 mg) was then dissolved in a solution of tetrahydrofuran (50 mL) and 1N HCl acid (20 mL). After stirring the mixture at room temperature for two hours, the tetrahydrofuran was removed in vacuo and the white solid (desired ketone product, 0.3 g) was collected by the filtration. The remaining aqueous phase was extracted with ethyl acetate. The organic layers were combined, dried (MgSO4, and concentrated. Purification by column chromatography (0-100% ethyl acetate in heptane) provided additional ketone product (yellow solid, 0.08 g). HRMS: calc. 380.0064 [M+H]+, found 380.9960; $^1$H NMR (400 MHz, chloroform-d3) δ ppm=8.53 (s, 1H), 7.52 (d, J=2.7 Hz, 3H), 6.46 (d, J=0.7 Hz, 1H), 2.64 (s, 3H).

Step 2: 8-Chloro-1-(2,6-dichlorophenyl)-5-(2-hydroxybut-3-en-2-yl)-2-methyl-1,6-naphthyridin-4(1H)-one

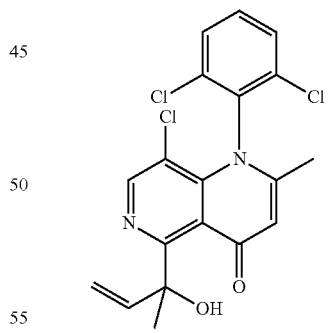

To an ice cold solution of ketone intermediate from step 1 (0.2 g, 0.524 mmol) in THF (1 ml) was added 1M vinylmagnesium bromide (0.681 ml, 0.681 mmol) in THF (3 ml) dropwise under nitrogen atmosphere. The reaction was stirred at 0° C. for 5 hours, then quenched with sat.NH$_4$Cl at 0° C. and extracted with EtOAC. The organic phase was washed with brine, dried over MgSO4, and concentrated. The crude product was purified by column chromatography eluting with 0-100% EtOAC/heptane to afford the desired product (0.048 g, 0.11 mmol) as a yellow solid, ESI-MS m/z: 411.1 [M+H]+

Step 3: 8-Chloro-1-(2,6-dichlorophenyl)-5-(2,4-dihydroxy-3-oxobutan-2-yl)-2-methyl-1,6-naphthyridin-4(1H)-one

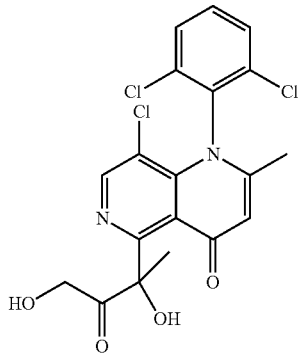 [SMILES: Cc1cc(=O)c2c(C(C)(O)C(=O)CO)ncc(Cl)c2n1-c1c(Cl)cccc1Cl]

To a solution of the product of step 2 (50 mg, 0.122 mmol) in dioxane (3 ml) and water (0.2 ml) was added osmium tetroxide (7.66 μl, 0.024 mmol) and NMO (42.9 mg, 0.366 mmol) at rt. The resulting solution was stirred at rt overnight. The reaction was concentrated and taken up into EtOAC. The organic phase was washed with water, brine, dried (over MgSO4), filtered and concentrated in vacuo. The crude residue was purified by basic preparative HPLC (Waters X-bridge 30×50 mm 5 um column, ACN/H$_2$O with 10 mM NH$_4$OH, 75 mL/min, 1.5 mL injection, gradient: 25-50% ACN in 4.5 min) to give 8-chloro-1-(2,6-dichlorophenyl)-5-(2,4-dihydroxy-3-oxobutan-2-yl)-2-methyl-1,6-naphthyridin-4(1H)-one (4.6 mg, 9.37 umol)

89: HRMS: calc. 441.0175 [M+H]$^+$, found 441.0191; $^1$H NMR (400 MHz, chloroform-d3) δ ppm=8.08 (s, 1H), 7.56-7.41 (m, 3H), 6.42 (s, 1H), 5.13 (s, 1H), 4.76 (dd, J=10.7, 4.1 Hz, 1H), 4.63 (dd, J=10.7, 4.6 Hz, 1H), 4.42 (s, 1H), 2.49 (s, 3H), 1.94 (s, 3H).

The examples below were prepared as described in Scheme D

Example 90: 1-(4-(3-Amino-3-methylbut-1-yn-1-yl)-2,6-dichlorophenyl)-8-chloro-5-(2,3-dihydroxypropoxy)-2-methyl-1,6-naphthyridin-4(1H)-one

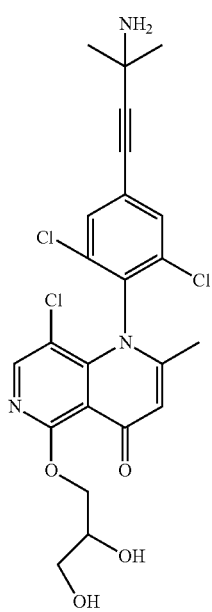 [SMILES: Cc1cc(=O)c2c(OCC(O)CO)ncc(Cl)c2n1-c1c(Cl)cc(C#CC(C)(C)N)cc1Cl]

Step 1: 1-(4-Bromo-2,6-dichlorophenyl)-8-chloro-5-((2,2-dimethyl-1,3-dioxolan-4-yl)methoxy)-2-methyl-1,6-naphthyridin-4(1H)-one

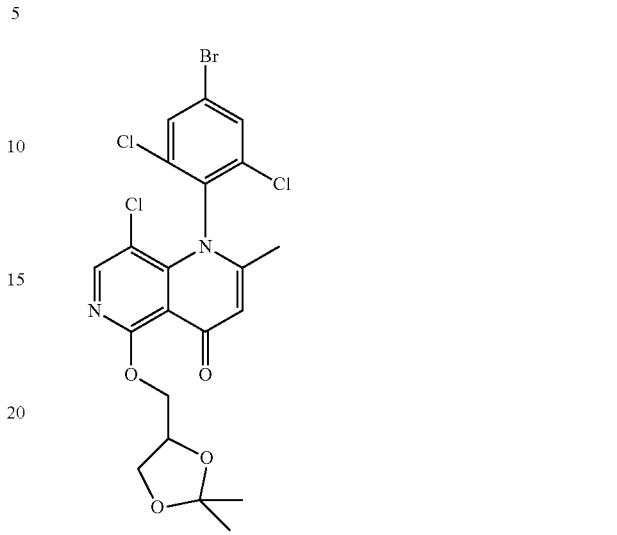

A mixture of 1-(4-bromo-2,6-dichlorophenyl)-5,8-dichloro-2-methyl-1,6-naphthyridin-4(1H)-one (intermediate 4, 0.2 g, 0.442 mmol), (2,2-dimethyl-1,3-dioxolan-4-yl)methanol (0.875 g, 6.62 mmol), K$_2$CO$_3$ (0.366 g, 2.65 mmol) and DMAP (11 mg, 0.088 mmol) in acetonitrile (24 mL) was stirred at 75° C. overnight. The solid was filtered out. Volatiles were removed under reduced pressure and the residue was purified with silica-gel chromatography (20-50% EtOAc/heptane) to afford the title compound (0.212 g, 88%). ESI-MS m/z: 548.9 [M+H]$^+$ (Rt=1.50 min, LC-method 3)

Step 2: 1-(4-(3-Amino-3-methylbut-1-yn-1-yl)-2,6-dichlorophenyl)-8-chloro-5-((2,2-dimethyl-1,3-dioxolan-4-yl)methoxy)-2-methyl-1,6-naphthyridin-4(1H)-one

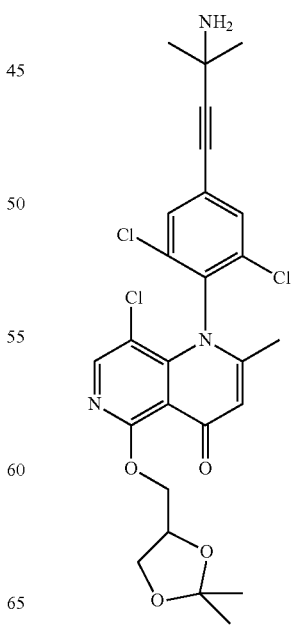

To a mixture of 1-(4-bromo-2,6-dichlorophenyl)-8-chloro-5-((2,2-dimethyl-1,3-dioxolan-4-yl)methoxy)-2-methyl-1,6-naphthyridin-4(1H)-one (46 mg, 0.084 mmol), 2-methylbut-3-yn-2-amine (21 mg, 0.252 mmol), Pd(PPh$_3$)$_4$ (19 mg, 0.017 mmol) and CuI (6.4 mg, 0.034 mmol) in DMF (pre-bubbled with N$_2$ for 30 min.) was added TEA (42 mg, 0.419 mmol). The reaction mixture was stirred at 70° C. under N$_2$ protection for 1 h. Volatiles were removed under reduced pressure and the residue was purified with silica-gel chromatography (1-5% MeOH/DCM) to afford the title compound. ESI-MS m/z: 552.0 [M+H]$^+$ (Rt=1.37 min, LC-method 3)

Step 3: 1-(4-(3-Amino-3-methylbut-1-yn-1-yl)-2,6-dichlorophenyl)-8-chloro-5-(2,3-dihydroxypropoxy)-2-methyl-1,6-naphthyridin-4(1H)-one

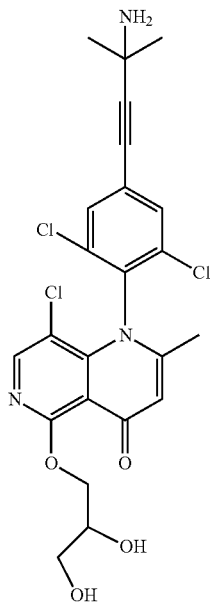 [SMILES: Cc1cc(=O)c2c(OCC(O)CO)ncc(Cl)c2n1-c1c(Cl)cc(C#CC(C)(C)N)cc1Cl]

A mixture of 1-(4-(3-amino-3-methylbut-1-yn-1-yl)-2,6-dichlorophenyl)-8-chloro-5-((2,2-dimethyl-1,3-dioxolan-4-yl)methoxy)-2-methyl-1,6-naphthyridin-4(1H)-one (46 mg, 0.084 mmol) and aq. HCl (1N, 1.0 mL, 1.0 mmol) in THF (2 mL) was stirred at room temperature overnight. The reaction mixture was then quenched with aq. NaOH (1N, 1 mL, 1.0 mmol). THF was then removed under reduced pressure and the residue was purified with reverse phase HPLC (Waters X-bridge 30×50 mm 5 um column, ACN/H$_2$O with 10 mM NH$_4$OH, 75 mL/min, 1.5 mL injection, gradient: 25-50% ACN in 4.5 min) to afford white solid as the title compound (26 mg, 58% yield). 90: HRMS: calc. 510.0749 [M+H]$^+$, found 510.0752; $^1$H NMR (400 MHz, DMSO-d6) δ ppm=8.25 (s, 1H), 7.75 (s, 2H), 6.47 (d, J=0.7 Hz, 1H), 4.87 (d, J=5.2 Hz, 1H), 4.76 (t, J=6.0 Hz, 1H), 4.37 (dd, J=10.7, 5.5 Hz, 1H), 4.28 (dd, J=10.7, 5.8 Hz, 1H), 3.86 (q, J=5.3 Hz, 1H), 3.64-3.49 (m, 2H), 1.90 (s, 3H), 1.40 (s, 6H)

Example 91: 8-Chloro-1-(2,6-dichloro-4-(3-morpholinoprop-1-yn-1-yl)phenyl)-5-(2-hydroxyethoxy)-2-methyl-1,6-naphthyridin-4(1H)-one

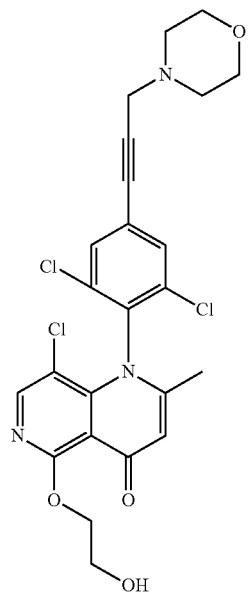 [SMILES: Cc1cc(=O)c2c(OCCO)ncc(Cl)c2n1-c1c(Cl)cc(C#CCN2CCOCC2)cc1Cl]

This compound was prepared analogous to the above example using unprotected ethane-1,2-diol in step 1 and omitting the unnecessary deprotection step 91: HRMS: calc. 522.0754 [M+H]$^+$, found 522.0751; $^1$H-NMR (400 MHz, DMSO-d6) δ ppm=8.23 (s, 1H), 7.88 (s, 2H), 6.45 (d, J=0.8 Hz, 1H), 4.76 (t, J=5.6 Hz, 1H), 4.41 (t, J=5.5 Hz, 2H), 3.75 (q, J=5.5 Hz, 2H), 3.65-3.60 (m, 4H), 3.59 (s, 2H), 2.58-2.53 (m, 4H), 1.95-1.82 (m, 3H)

Example 92: 8-Chloro-1-(2,6-dichloro-4-(3-(1,1-dioxidothiomorpholino)prop-1-yn-1-yl)phenyl)-5-(2-hydroxyethoxy)-2-methyl-1,6-naphthyridin-4(1H)-one

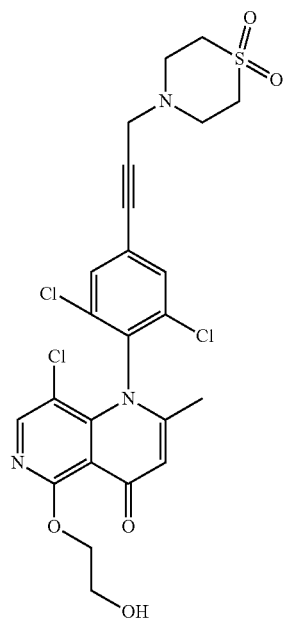 [SMILES: Cc1cc(=O)c2c(OCCO)ncc(Cl)c2n1-c1c(Cl)cc(C#CCN2CCS(=O)(=O)CC2)cc1Cl]

This compound was prepared analogous to the above example using unprotected ethane-1,2-diol in step 1 and omitting the unnecessary deprotection step 92: HRMS: calc. 570.0424 [M+H]$^+$, found 570.0422; $^1$H NMR (400 MHz, DMSO-d6) δ ppm=8.23 (s, 1H), 7.87 (s, 2H), 6.45 (d, J=0.7 Hz, 1H), 4.76 (t, J=5.4 Hz, 1H), 4.41 (t, J=5.5 Hz, 2H), 3.76 (d, J=10.0 Hz, 4H), 3.23-3.13 (m, 4H), 3.05 (dd, J=6.6, 3.5 Hz, 4H), 1.90 (s, 3H)

Example 93: 8-Chloro-1-(2,6-dichloro-4-(3-(dimethylamino)prop-1-yn-1-yl)phenyl)-5-((2,2-dimethyl-1,3-dioxolan-4-yl)methoxy)-2-methyl-1,6-naphthyridin-4(1H)-one

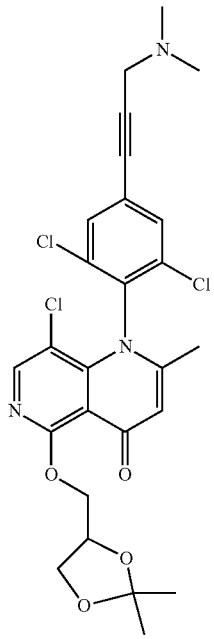 [SMILES: Cc1cc(=O)c2c(OCC3COC(C)(C)O3)ncc(Cl)c2n1-c1c(Cl)cc(C#CCN(C)C)cc1Cl]

This compound was prepared analogous to the above example using N,N-dimethylprop-2-yn-1-amine in step 2 and omitting the unnecessary deprotection step 3.

93: HRMS: calc. 550.1067 [M+H]$^+$, found 550.1076; $^1$H NMR (400 MHz, DMSO-d6) δ ppm=8.23 (s, 1H), 7.86 (s, 2H), 6.50-6.39 (m, 1H), 4.51-4.32 (m, 3H), 4.10 (td, J=6.0, 3.2 Hz, 1H), 4.03-3.94 (m, 1H), 3.53 (s, 2H), 2.27 (s, 6H), 1.90 (s, 3H), 1.35 (s, 3H), 1.31 (s, 3H)

Preparation of Phosphate Prodrugs

Examples with a free hydroxy group can be converted into phosphate prodrugs as demonstrated by example 3:

Prodrug of example 3: (8-Chloro-1-(2,6-dichlorophenyl)-5-(2,3-dihydroxypropoxy)-4-oxo-1,4-dihydro-1,6-naphthyridin-2-yl)methyl dihydrogen phosphate

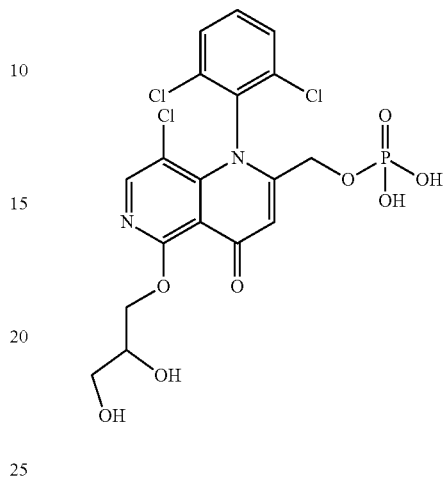

Step 1: 2-(((tert-Butyldimethylsilyl)oxy)methyl)-8-chloro-1-(2,6-dichlorophenyl)-5-((2,2-dimethyl-1,3-dioxolan-4-yl)methoxy)-1,6-naphthyridin-4(1H)-one A mixture of 2-(((tert-butyldimethylsilyl)oxy)methyl)-5,8-dichloro-1-(2,6-dichlorophenyl)-1,6-naphthyridin-4(1H)-one (3.5 g, 6.94 mmol), (2,2-dimethyl-1,3-dioxolan-4-yl)methanol (4.59 g, 34.7 mmol), K$_2$CO$_3$ (2.88 g, 20.82 mmol) and DMAP (0.848 g, 6.94 mmol) in ACN (40 mL) was heated at 80° C. overnight. The reaction mixture was filtered off and washed with ACN. The filtrate was concentrated in vacuo. The residue was purified by silica gel chromatography (10-50% EtOAc in heptane) to give the title compound (2.99 g, 72% yield). ESI-MS m/z: 601.1 [M+H]$^+$ (Rt=1.62 min, LC-method 1), $^1$H NMR (400 MHz, DCM-d2) δ ppm=8.03 (s, 1H), 7.47 (s, 3H), 6.67 (t, J=1.1 Hz, 1H), 4.60-4.40 (m, 3H), 4.22-3.92 (m, 4H), 1.40 (s, 3H), 1.36 (s, 3H), 0.85 (s, 9H), 0.0 (s, 6H).

Step 2: 8-Chloro-1-(2,6-dichlorophenyl)-5-((2,2-dimethyl-1,3-dioxolan-4-yl)methoxy)-2-(hydroxymethyl)-1,6-naphthyridin-4(1H)-one To a solution of 2-(((tert-butyldimethylsilyl)oxy)methyl)-8-chloro-1-(2,6-dichlorophenyl)-5-((2,2-dimethyl-1,3-dioxolan-4-yl)methoxy)-1,6-naphthyridin-4(1H)-one (2.9 g, 4.83 mmol) in THF (20 ml) was added a 1 M solution of TBAF in THF (7.25 ml, 7.25 mmol) at 0° C. The reaction was stirred at 0° C. for 1 hour. It was quenched with water and diluted in EtOAc. The aqueous layer was extracted with EtOAc. The combined organic layer was washed with brine, dried over Na$_2$SO$_4$, filtered, and concentrated under reduced pressure. The residue was purified by silica gel chromatography (10-100% EtOAc in heptane) to give the title compound (1.74 g, 74% yield). ESI-MS m/z: 487 [M+H]$^+$ (Rt=1.06 min, LC-method 1), $^1$H NMR (400 MHz, DCM-d2) δ ppm=8.14 (s, 1H), 7.54 (d, J=1.9 Hz, 3H), 6.99 (s, 1H), 4.66-4.46 (m, 3H), 4.28-4.17 (m, 1H), 4.15-3.96 (m, 3H), 1.47 (s, 3H), 1.41 (s, 3H).

Step 3: Dibenzyl ((8-chloro-1-(2,6-dichlorophenyl)-5-((2,2-dimethyl-1,3-dioxolan-4-yl)methoxy)-4-oxo-1,4-dihydro-1,6-naphthyridin-2-yl)methyl) phosphate Hünig's base (0.027 ml, 0.154 mmol) and tetrabenzyl pyrophosphate (0.078 g, 0.144 mmol) added to a solution of 8-chloro-1-(2,6-dichlorophenyl)-5-((2,2-dimethyl-1,3-dioxolan-4-yl)methoxy)-2-(hydroxymethyl)-1,6-naphthyridin-4(1H)-one (0.05 g, 0.103 mmol) in DCM (0.5 ml) at rt followed by MgCl$_2$ (9.80 mg, 0.103 mmol). The resulting mixture was stirred at room temperature overnight. The mixture was filtered through a 20:1 silica/MgSO4 plug and washed with EtOAc/ether. The filtrate was concentrated under reduced pressure and the residue was purified by silica gel chromatography (0-100% EtOAc in heptane) to give the title compound (0.061 g, 79% yield). ESI-MS m/z: 747.0 [M+H]$^+$ (Rt=1.43 min, LC-method 1), $^1$H NMR (400 MHz, DCM-d2) δ ppm=8.10 (s, 1H), 7.52-7.28 (m, 13H), 6.61-6.48 (m, 1H), 5.03 (d, J=8.6 Hz, 4H), 4.66-4.48 (m, 3H), 4.37 (dd, J=6.7, 0.8 Hz, 2H), 4.22 (dd, J=8.5, 6.1 Hz, 1H), 4.06 (dd, J=8.4, 6.2 Hz, 1H), 1.49 (s, 3H), 1.43 (s, 3H).

Step 4 and 5: (8-Chloro-1-(2,6-dichlorophenyl)-5-(2,3-dihydroxypropoxy)-4-oxo-1,4-dihydro-1,6-naphthyridin-2-yl)methyl dihydrogen phosphate To a solution of dibenzyl ((8-chloro-1-(2,6-dichlorophenyl)-5-((2,2-dimethyl-1,3-dioxolan-4-yl)methoxy)-4-oxo-1,4-dihydro-1,6-naphthyridin-2-yl)methyl) phosphate (40 mg, 0.054 mmol) and 1,4-cyclohexadiene (0.228 g, 2.84 mmol) in MeOH (5 ml) under nitrogen was added 10% Palladium on activated charcoal (amount) and the mixture was stirred at room temperature under nitrogen atmosphere for 4 hours. Then it was filtered through a filter (Nylon 0.45 um) and the filtrate was concentrated to dryness under reduced pressure. Diethylether was added to the solid, the mixture was stirred and organic layer was decanted. The residue was dried under vacuum to provide a mixture of two products. This mixture was dissolved in 0.5 ml of MeOH and TFA (0.044 ml, 0.566 mmol) was added at room temperature. The resulting solution was stirred for 2 hours and concentrated under reduced pressure. The residue was lyophilized from ACN and water to provide title product as a white solid (0.026 g, 87% yield). The title compound also contained some 3-((8-chloro-1-(2,6-dichlorophenyl)-4-oxo-2-((phosphonooxy)methyl)-1,4-dihydro-1,6-naphthyridin-5-yl)oxy)-2-hydroxypropyl 2,2,2-trifluoroacetate as observed by LC-Mass under acidic conditions.

Step 6: (8-Chloro-1-(2,6-dichlorophenyl)-5-(2,3-dihydroxpropoxy)-4-oxo-1,4-dihydro-1,6-naphthyridin-2-yl)methyl dihydrogen phosphate mono sodium salt The mixture (0.026 g) from the previous step was dissolved in MeOH (1 ml). The solution of NaHCO$_3$ (0.015 g, 0.183 mmol) in H$_2$O (1 ml) was added to the flask. The resulting solution was stirred at room temperature for 5 minutes, and concetrated under reduced pressure. The residue was lyophilized from ACN and water to provide the title compound (0.026 g, 99% yield). ESI-MS m/z: 524.9 [M+H]$^+$ (Rt=0.66 min, LC-method 2)$^1$H NMR (400 MHz, methanol-d4) δ ppm=8.16 (s, 1H), 7.60 (s, 3H), 7.14 (t, J=1.2 Hz, 1H), 4.61-4.47 (m, 2H), 4.35 (dd, J=4.4, 1.2 Hz, 2H), 4.06 (p, J=5.2 Hz, 1H), 3.81-3.66 (m, 2H).

The invention claimed is:

1. A method of treating a disease or disorder selected from cardiac arrhythmia, atrial fibrillation, primary hyperaldosteronism, hypertension, and sick sinus syndrome comprising administering to a subject in need thereof a therapeutically effective amount of a compound according to Formula I:

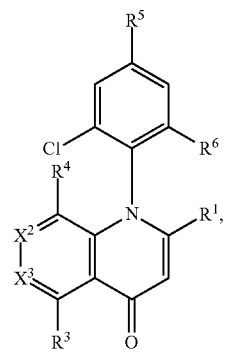

wherein:
 $X^2$ is $CR^2$ or N;
 $X^3$ is CH or N;
 $R^1$ is $C_{1-4}$alkyl, —CH$_2$CN, —CN, $C_{1-4}$alkoxy$C_{1-4}$alkyl, halo-$C_{1-4}$alkyl, —CH═N—OH, —CH═N—O—$C_{1-4}$alkyl, —CH═N—O-(hydroxy$C_{1-4}$alkyl), hydroxy-$C_{1-4}$alkyl, —CH$_2$OP(O)(OH)$_2$, or $C_{3-5}$cycloalkyl;
 $R^3$ is —OR$^a$; —NHR$^b$; —C(O)NH$_2$; —C(O)[hydroxyC$_{1-4}$alkyl]; 4- to 7-membered heterocyclyl containing at least one heteroatom selected from O, N, and S and optionally substituted with one or more substituents independently selected from OH and hydroxyC$_{1-4}$alkyl; and 5- or 6-membered heteroaryl containing 1 to 4 heteroatoms independently selected from O, N, and S and optionally substituted with one or more C$_{1-4}$alkyl; or
 $R^3$ is C$_{1-4}$alkyl substituted with one or more substituents independently selected from —C(O)[hydroxyC$_{1-4}$alkyl] and —OR$^c$;
 $R^a$ is —C$_{1-6}$alkyl substituted with one or more substituents independently selected from —OR$^c$, —SO$_2$C$_{1-4}$alkyl, —NHS(O)$_2$C$_{1-4}$alkyl, and 4- to 7-membered heterocyclyl containing at least one heteroatom selected from O, N, and S, which is further optionally substituted with one or more substituents independently selected from C$_{1-4}$alkyl and hydroxyC$_{1-4}$alkyl; or
 $R^a$ is H, —[CH$_2$—CH$_2$—O]$_m$—CH$_3$, or 5- or 6-membered heteroaryl containing 1 to 4 heteroatoms independently selected from O, N, and S and optionally substituted with one or more C$_{1-4}$alkyl; wherein n is 2-6 and m is 1-6;
 $R^b$ is —C$_{1-6}$alkyl substituted with one or more substituents independently selected from —OR$^c$, —C(O)NH—C$_{1-4}$alkyl, —C(O)NH-(hydroxyC$_{1-4}$alkyl), hydroxyC$_{1-4}$alkyl, 5- or 6-membered heteroaryl containing 1 to 4 heteroatoms independently selected from O, N and S, 4- to 7-membered heterocyclyl containing at least one heteroatom selected from O, N, and S, —SO$_2$C$_{1-4}$alkyl, and —NHS(O)$_2$C$_{1-4}$alkyl; or R$^b$ is —S(O)$_2$-(5- or 6-membered heteroaryl containing 1 to 4 heteroatoms independently selected from O, N, and S); or R$^b$ is 4- to 7-membered heterocyclyl containing at least one heteroatom selected from O, N, and S and optionally substituted with one or more hydroxy groups; or R$^b$ is H, —OR$^c$; —[CH$_2$—CH$_2$—O]$_m$—CH$_3$, or 5- or 6-membered heteroaryl containing 1 to 4 heteroatoms independently selected from O, N, and S and optionally substituted with one or more C$_{1-4}$alkyl; wherein n is 2-6 and m is 1-6;

R$^c$ is H or hydroxyC$_{1-4}$alkyl;

R$^2$ is H, C$_{1-4}$alkoxy, halo-C$_{1-4}$alkoxy, halo, C$_{1-4}$alkyl, —S—C$_{1-4}$alkyl, or —NH—C$_{1-4}$alkyl;

R$^4$ is H, halo, halo-C$_{1-4}$alkyl, C$_{1-4}$alkyl, or C$_{3-5}$cycloalkyl;

R$^5$ is H, halo, CN, C$_{1-4}$alkoxy, hydroxy-C$_{1-4}$alkoxy, C$_{1-4}$alkoxy-C$_{1-4}$alkoxy, —CH=NH—O—C$_{1-4}$alkyl, or —CH=NH—O(hydroxyC$_{1-4}$alkyl); or R$^5$ is C$_{2-6}$alkynyl optionally substituted with OH or NR$^g$R$^h$, wherein R$^g$ and R$^h$ are independently H or C$_{1-4}$alkyl; or R$^g$ and R$^h$ form together with the nitrogen to which they are attached a 4- to 7-membered heterocyclyl optionally containing an additional heteroatom selected from O, N, and S, wherein the heteroatom can be in its oxidized form; and wherein said heterocyclyl is optionally substituted with C$_{1-4}$alkyl; and R$^6$ is halo, C$_{1-4}$ alkyl, or CN;

or a pharmaceutically acceptable salt thereof.

2. The method of claim 1, wherein the disease or disorder is cardiac arrhythmia.

3. The method of claim 1, wherein the disease or disorder is atrial fibrillation.

4. The method of claim 1, wherein the disease or disorder is primary hyperaldosteronism.

5. The method of claim 1, wherein the disease or disorder is hypertension.

6. The method of claim 1, wherein the disease or disorder is sick sinus syndrome.

7. The method of claim 1, wherein the compound is selected from the group consisting of:

(S)-8-chloro-1-(2,6-dichlorophenyl)-5-(2,3-dihydroxypropoxy)-2-(hydroxymethyl)-1,6-naphthyridin-4(1H)-one;

(R)-8-chloro-1-(2,6-dichlorophenyl)-5-(2,3-dihydroxypropoxy)-2-(hydroxymethyl)-1,6-naphthyridin-4(1H)-one;

8-chloro-1-(2,6-dichlorophenyl)-5-(2,3-dihydroxypropoxy)-2-(hydroxymethyl)-1,6-naphthyridin-4(1H)-one;

(R)-8-chloro-1-(2,6-dichlorophenyl)-5-(3,4-dihydroxybutyl)-2-(hydroxymethyl)-1,6-naphthyridin-4(1H)-one;

(S)-8-chloro-1-(2,6-dichlorophenyl)-5-(3,4-dihydroxybutyl)-2-(hydroxymethyl)-1,6-naphthyridin-4(1H)-one; and 8-chloro-1-(2,6-dichlorophenyl)-5-(3,4-dihydroxybutyl)-2-(hydroxymethyl)-1,6-naphthyridin-4(1H)-one;

or a pharmaceutically acceptable salt thereof.

8. The method of claim 1, wherein the compound is (S)-8-chloro-1-(2,6-dichlorophenyl)-5-(2,3-dihydroxypropoxy)-2-(hydroxymethyl)-1,6-naphthyridin-4(1H)-one, or a pharmaceutically acceptable salt thereof.

9. A method of treating a disease or disorder selected from cardiac arrhythmia, atrial fibrillation, primary hyperaldosteronism, hypertension, and sick sinus syndrome comprising administering to a subject in need thereof a therapeutically effective amount of a compound according to Formula II or Formula III:

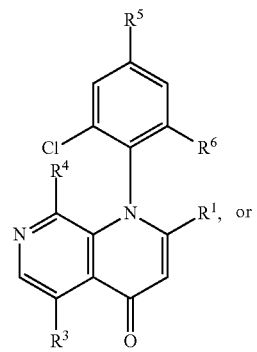

II

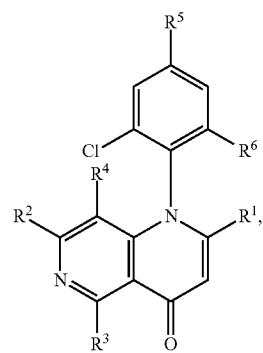

III wherein:

R$^1$ is C$_{1-4}$alkyl, —CH$_2$CN, —CN, C$_{1-4}$alkoxyC$_{1-4}$alkyl, halo-C$_{1-4}$alkyl, —CH=N—OH, —CH=N—O—C$_{1-4}$alkyl, —CH=N—O-(hydroxyC$_{1-4}$alkyl), hydroxy-C$_{1-4}$alkyl, —CH$_2$OP(O)(OH)$_2$, or C$_{3-5}$cycloalkyl;

R$^3$ is —OR$^a$; —NHR$^b$; —C(O)NH$_2$; —C(O)[hydroxyC$_{1-4}$alkyl]; 4- to 7-membered heterocyclyl containing at least one heteroatom selected from O, N, and S and optionally substituted with one or more substituents independently selected from OH and hydroxyC$_{1-4}$alkyl; and 5- or 6-membered heteroaryl containing 1 to 4 heteroatoms independently selected from O, N, and S and optionally substituted with one or more C$_{1-4}$alkyl; or R$^3$ is C$_{1-4}$alkyl substituted with one or more substituents independently selected from —C(O)[hydroxyC$_{1-4}$alkyl] and —OR$^c$;

R$^a$ is —C$_{1-6}$alkyl substituted with one or more substituents independently selected from —OR$^c$, —SO$_2$C$_{1-4}$alkyl, —NHS(O)$_2$C$_{1-4}$alkyl, and 4- to 7-membered heterocyclyl containing at least one heteroatom selected from O, N, and S, which is further optionally substituted with one or more substituents independently selected from C$_{1-4}$alkyl and hydroxyC$_{1-4}$alkyl; or R$^a$ is H, —[CH$_2$—CH$_2$—O]$_m$—CH$_3$, or 5- or 6-membered heteroaryl containing 1 to 4 heteroatoms independently selected from O, N, and S and optionally substituted with one or more C$_{1-4}$alkyl; wherein n is 2-6 and m is 1-6;

$R^b$ is —$C_{1-6}$alkyl substituted with one or more substituents independently selected from —$OR^c$, —C(O)NH—$C_{1-4}$alkyl, —C(O)NH-(hydroxy$C_{1-4}$alkyl), hydroxy$C_{1-4}$alkyl, 5- or 6-membered heteroaryl containing 1 to 4 heteroatoms independently selected from O, N and S, 4- to 7-membered heterocyclyl containing at least one heteroatom selected from O, N, and S, —$SO_2C_{1-4}$alkyl, and —$NHS(O)_2C_{1-4}$alkyl; or $R^b$ is —$S(O)_2$-(5- or 6-membered heteroaryl containing 1 to 4 heteroatoms independently selected from O, N, and S); or $R^b$ is 4- to 7-membered heterocyclyl containing at least one heteroatom selected from 0, N, and S and optionally substituted with one or more hydroxy groups; or $R^b$ is H, —$OR^c$; —$[CH_2—CH_2—O]_m$—$CH_3$, or 5- or 6-membered heteroaryl containing 1 to 4 heteroatoms independently selected from O, N, and S and optionally substituted with one or more $C_{1-4}$alkyl; wherein n is 2-6 and m is 1-6;

$R^c$ is H or hydroxy$C_{1-4}$alkyl;

$R^2$ is H, $C_{1-4}$alkoxy, halo-$C_{1-4}$alkoxy, halo, $C_{1-4}$alkyl, —S—$C_{1-4}$alkyl, or —NH—$C_{1-4}$alkyl;

$R^4$ is H, halo, halo-$C_{1-4}$alkyl, $C_{1-4}$alkyl, or $C_{3-5}$cycloalkyl;

$R^5$ is H, halo, CN, $C_{1-4}$alkoxy, hydroxy-$C_{1-4}$alkoxy, $C_{1-4}$alkoxy-$C_{1-4}$alkoxy, —CH=NH—O—$C_{1-4}$alkyl, or —CH=NH—O(hydroxy$C_{1-4}$alkyl); or $R^5$ is $C_{2-6}$alkynyl optionally substituted with OH or $NR^gR^h$, wherein $R^g$ and $R^h$ are independently H or $C_{1-4}$alkyl; or $R^g$ and $R^h$ form together with the nitrogen to which they are attached a 4- to 7-membered heterocyclyl optionally containing an additional heteroatom selected from O, N, and S, wherein the heteroatom can be in its oxidized form; and wherein said heterocyclyl is optionally substituted with $C_{1-4}$alkyl; and $R^6$ is halo, $C_{1-4}$ alkyl, or CN;

or a pharmaceutically acceptable salt thereof.

10. The method of claim 9, wherein the disease or disorder is cardiac arrhythmia.

11. The method of claim 9, wherein the disease or disorder is atrial fibrillation.

12. The method of claim 9, wherein the disease or disorder is primary hyperaldosteronism.

13. The method of claim 9, wherein the disease or disorder is hypertension.

14. The method of claim 9, wherein the disease or disorder is sick sinus syndrome.

15. The method of claim 9, wherein the compound is selected from the group consisting of:

(S)-8-chloro-1-(2,6-dichlorophenyl)-5-(2,3-dihydroxypropoxy)-2-(hydroxymethyl)-1,6-naphthyridin-4(1H)-one;

(R)-8-chloro-1-(2,6-dichlorophenyl)-5-(2,3-dihydroxypropoxy)-2-(hydroxymethyl)-1,6-naphthyridin-4(1H)-one;

8-chloro-1-(2,6-dichlorophenyl)-5-(2,3-dihydroxypropoxy)-2-(hydroxymethyl)-1,6-naphthyridin-4(1H)-one;

(R)-8-chloro-1-(2,6-dichlorophenyl)-5-(3,4-dihydroxybutyl)-2-(hydroxymethyl)-1,6-naphthyridin-4(1H)-one;

(S)-8-chloro-1-(2,6-dichlorophenyl)-5-(3,4-dihydroxybutyl)-2-(hydroxymethyl)-1,6-naphthyridin-4(1H)-one; and 8-chloro-1-(2,6-dichlorophenyl)-5-(3,4-dihydroxybutyl)-2-(hydroxymethyl)-1,6-naphthyridin-4(1H)-one;

or a pharmaceutically acceptable salt thereof.

16. The method of claim 9, wherein the compound is (S)-8-chloro-1-(2,6-dichlorophenyl)-5-(2,3-dihydroxypropoxy)-2-(hydroxymethyl)-1,6-naphthyridin-4 (1H)-one, or a pharmaceutically acceptable salt thereof.

* * * * *